United States Patent
Edmiston et al.

(10) Patent No.: US 12,419,643 B2
(45) Date of Patent: *Sep. 23, 2025

(54) MEDICAL DEVICE FOR MODIFICATION OF LEFT ATRIAL APPENDAGE AND RELATED SYSTEMS AND METHODS

(71) Applicant: Coherex Medical, Inc., Salt Lake City, UT (US)

(72) Inventors: Daryl R. Edmiston, Draper, UT (US); Clark C. Davis, Holladay, UT (US); Scott D. Miles, Sandy, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/596,258

(22) Filed: Mar. 5, 2024

(65) Prior Publication Data
US 2024/0206880 A1     Jun. 27, 2024

Related U.S. Application Data

(60) Division of application No. 16/859,282, filed on Apr. 27, 2020, now Pat. No. 11,918,227, which is a
(Continued)

(51) Int. Cl.
*A61B 17/12*     (2006.01)
*A61B 17/00*     (2006.01)
(Continued)

(52) U.S. Cl.
CPC .... *A61B 17/12122* (2013.01); *A61B 17/0057* (2013.01); *A61B 17/12022* (2013.01);
(Continued)

(58) Field of Classification Search
CPC .......... A61B 17/12122; A61B 17/0057; A61B 17/12022; A61B 17/12172;
(Continued)

(56) References Cited

U.S. PATENT DOCUMENTS 3,095,877 A   7/1963   Rowan
3,874,388 A   4/1975   King et al.
(Continued)

FOREIGN PATENT DOCUMENTS

CA   2659109   3/2008
CA   2627408   5/2008
(Continued)

OTHER PUBLICATIONS

Office Action and English Translation issued in JP 2018-027625 on Dec. 21, 2021.
(Continued)

*Primary Examiner* — Richard G Louis
(74) *Attorney, Agent, or Firm* — David L. Stott

(57) ABSTRACT

Devices, methods and systems are provided for occluding an opening within the tissue of a body, such as a left atrial appendage. In one embodiment, a medical device includes an occluder portion and an anchor portion. The occluder portion includes a hub that defines an axis, the occluder portion extending between a proximal end coupled to the hub and a distal end defining an occluder eyelet adjacent thereto. The anchor portion extends between a first end and a second end, the first end coupled to an anchor hub and the second end defining an anchor eyelet adjacent thereto and hingeably coupled to the occluder eyelet. With this arrangement, the anchor hub is moveable along the axis to move the anchor portion between a retracted position and a deployed position upon the occluder portion being in an expanded position.

20 Claims, 25 Drawing Sheets

Related U.S. Application Data continuation of application No. 15/438,650, filed on Feb. 21, 2017, now Pat. No. 10,631,969, which is a continuation-in-part of application No. 15/094,254, filed on Apr. 8, 2016, now Pat. No. 10,064,628, which is a continuation-in-part of application No. 14/308,695, filed on Jun. 18, 2014, now Pat. No. 9,649,115, which is a continuation-in-part of application No. 13/666,612, filed on Nov. 1, 2012, now Pat. No. 9,693,781, which is a continuation-in-part of application No. 12/818,046, filed on Jun. 17, 2010, now Pat. No. 8,636,764.

(60) Provisional application No. 62/148,317, filed on Apr. 16, 2015, provisional application No. 61/837,628, filed on Jun. 20, 2013, provisional application No. 61/661,799, filed on Jun. 19, 2012, provisional application No. 61/553,948, filed on Nov. 1, 2011, provisional application No. 61/345,514, filed on May 17, 2010, provisional application No. 61/325,230, filed on Apr. 16, 2010, provisional application No. 61/320,635, filed on Apr. 2, 2010, provisional application No. 61/294,058, filed on Jan. 11, 2010, provisional application No. 61/218,018, filed on Jun. 17, 2009.

(51) Int. Cl.
A61B 90/00 (2016.01)
A61F 2/01 (2006.01)
A61M 5/00 (2006.01)

(52) U.S. Cl.
CPC .. *A61B 17/12172* (2013.01); *A61B 17/12177* (2013.01); *A61B 2017/00575* (2013.01); *A61B 2017/00597* (2013.01); *A61B 2017/00893* (2013.01); *A61B 2017/00942* (2013.01); *A61B 2017/12004* (2013.01); *A61B 2017/1205* (2013.01); *A61B 2017/12054* (2013.01); *A61B 2017/12095* (2013.01); *A61B 2090/3966* (2016.02); *A61F 2/011* (2020.05); *A61F 2002/016* (2013.01); *A61F 2210/0014* (2013.01); *A61F 2220/0016* (2013.01); *A61F 2250/0067* (2013.01); *A61M 5/007* (2013.01)

(58) Field of Classification Search
CPC .... A61B 17/12177; A61B 2017/00575; A61B 2017/00597; A61B 2017/00893; A61B 2017/00942; A61B 2017/12004; A61B 2017/1205; A61B 2017/12054; A61B 2017/12095; A61B 2090/3966; A61F 2/011; A61F 2002/016; A61F 2210/0014; A61F 2220/0016; A61F 2250/0067; A61M 5/007
See application file for complete search history.

(56) References Cited

U.S. PATENT DOCUMENTS

| | | | |
|---|---|---|---|
| 5,171,259 A | 12/1992 | Inoue | |
| 5,192,301 A | 3/1993 | Kamiya et al. | |
| 5,284,488 A | 2/1994 | Sideris | |
| 5,334,217 A | 8/1994 | Das | |
| 5,425,733 A | 6/1995 | Schmieding | |
| 5,425,740 A | 6/1995 | Hutchinson, Jr. | |
| 5,433,727 A | 7/1995 | Sideris | |
| 5,792,165 A | 8/1998 | Klieman et al. | |
| 5,797,886 A | 8/1998 | Roth et al. | |
| 5,861,003 A | 1/1999 | Latson et al. | |
| 5,904,703 A | 5/1999 | Gilson | |
| 5,910,154 A | 6/1999 | Tsugita et al. | |
| 5,935,112 A | 8/1999 | Stevens et al. | |
| 5,992,158 A | 11/1999 | Goddard et al. | |
| 6,096,027 A | 8/2000 | Layne | |
| 6,152,144 A | 11/2000 | Lesh et al. | |
| 6,174,322 B1 | 1/2001 | Schneidt | |
| 6,231,561 B1 | 5/2001 | Frazier et al. | |
| 6,238,403 B1 | 5/2001 | Greene et al. | |
| 6,290,674 B1 | 9/2001 | Roue et al. | |
| 6,328,727 B1 | 12/2001 | Frazier et al. | |
| 6,355,051 B1 | 3/2002 | Sisskind et al. | |
| 6,371,971 B1 | 4/2002 | Tsugita et al. | |
| 6,398,760 B1 | 6/2002 | Danby | |
| 6,419,669 B1 | 7/2002 | Frazier et al. | |
| 6,436,088 B2 | 8/2002 | Frazier et al. | |
| 6,458,100 B2 | 10/2002 | Roue et al. | |
| 6,488,689 B1 | 12/2002 | Kaplan et al. | |
| 6,530,934 B1 | 3/2003 | Jacobsen et al. | |
| 6,551,303 B1 | 4/2003 | Van Tassel et al. | |
| 6,551,341 B2 | 4/2003 | Boylan et al. | |
| 6,561,969 B2 | 5/2003 | Frazier et al. | |
| 6,585,754 B2 | 7/2003 | Wallace et al. | |
| 6,650,923 B1 | 11/2003 | Lesh et al. | |
| 6,651,557 B1 | 11/2003 | Frazier et al. | |
| 6,652,555 B1 | 11/2003 | Tassel et al. | |
| 6,652,556 B1 | 11/2003 | Tassel et al. | |
| 6,666,861 B1 | 12/2003 | Grabek | |
| 6,689,150 B1 | 2/2004 | Tassel et al. | |
| 6,702,825 B2 | 3/2004 | Frazier et al. | |
| 6,706,065 B2 | 3/2004 | Langberg et al. | |
| 6,712,804 B2 | 3/2004 | Roue et al. | |
| 6,730,108 B2 | 5/2004 | Van Tassel et al. | |
| 6,746,472 B2 | 6/2004 | Frazier et al. | |
| 6,790,229 B1 | 9/2004 | Berreklouw | |
| 6,949,113 B2 | 9/2005 | Van Tassel et al. | |
| 6,979,344 B2 | 12/2005 | Jones et al. | |
| 6,994,092 B2 | 2/2006 | van der Burg et al. | |
| 7,011,671 B2 | 3/2006 | Welch | |
| 7,014,645 B2 | 3/2006 | Greene, Jr. et al. | |
| 7,025,756 B2 | 4/2006 | Frazier et al. | |
| 7,044,134 B2 | 5/2006 | Khairkhahan et al. | |
| 7,056,294 B2 | 6/2006 | Khairkhahan et al. | |
| 7,115,110 B2 | 10/2006 | Frazier et al. | |
| 7,128,073 B1 | 10/2006 | van der Burg et al. | |
| 7,152,605 B2 | 12/2006 | Khairkhahan et al. | |
| 7,169,164 B2 | 1/2007 | Borillo et al. | |
| 7,192,439 B2 | 3/2007 | Khairkhahan et al. | |
| 7,226,458 B2 | 6/2007 | Kaplan et al. | |
| 7,293,562 B2 | 11/2007 | Malecki et al. | |
| 7,597,704 B2 | 10/2009 | Frazier et al. | |
| 7,608,091 B2 | 10/2009 | Goldfarb et al. | |
| 7,717,937 B2 | 5/2010 | Wahr et al. | |
| 7,727,189 B2 | 6/2010 | Tassel et al. | |
| 7,780,645 B2 | 8/2010 | Jones | |
| 7,842,054 B2 | 11/2010 | Greene, Jr. et al. | |
| 8,142,470 B2 | 3/2012 | Quinn et al. | |
| 8,636,764 B2 | 1/2014 | Miles et al. | |
| 8,690,911 B2 | 4/2014 | Miles et al. | |
| 8,715,318 B2 | 5/2014 | Miles et al. | |
| 8,740,934 B2 | 6/2014 | McGuckin, Jr. | |
| 8,795,328 B2 | 8/2014 | Miles et al. | |
| 8,840,641 B2 | 9/2014 | Miles et al. | |
| 8,845,711 B2 | 9/2014 | Miles et al. | |
| 9,351,716 B2 | 5/2016 | Miles et al. | |
| 9,649,115 B2 | 5/2017 | Edmiston et al. | |
| 9,693,780 B2 | 7/2017 | Miles et al. | |
| 9,693,781 B2 | 7/2017 | Miles et al. | |
| 9,883,864 B2 | 2/2018 | Miles et al. | |
| 10,631,969 B2* | 4/2020 | Edmiston | A61B 17/12172 |
| 2001/0003161 A1 | 6/2001 | Vardi et al. | |
| 2001/0037129 A1 | 11/2001 | Thill | |
| 2001/0037141 A1 | 11/2001 | Yee et al. | |
| 2002/0022860 A1 | 2/2002 | Borillo et al. | |
| 2002/0026094 A1 | 2/2002 | Roth | |
| 2002/0026217 A1 | 2/2002 | Baker et al. | |
| 2002/0035374 A1 | 3/2002 | Borillo et al. | |
| 2002/0062130 A1 | 5/2002 | Jugenheimer et al. | |
| 2002/0111647 A1 | 8/2002 | Khairkhahan et al. | |
| 2002/0177855 A1 | 11/2002 | Greene, Jr. et al. | |

(56) References Cited

U.S. PATENT DOCUMENTS

| | | |
|---|---|---|
| 2002/0183787 A1 | 12/2002 | Wahr et al. |
| 2002/0183826 A1 | 12/2002 | Dorn et al. |
| 2003/0014075 A1 | 1/2003 | Rosehbluth et al. |
| 2003/0023266 A1 | 1/2003 | Borillo et al. |
| 2003/0028213 A1 | 2/2003 | Thill et al. |
| 2003/0050658 A1 | 3/2003 | Trask et al. |
| 2003/0055455 A1 | 3/2003 | Yang et al. |
| 2003/0057156 A1 | 3/2003 | Peterson et al. |
| 2003/0120337 A1 | 6/2003 | Van Tassel et al. |
| 2003/0125790 A1 | 7/2003 | Fastovsky et al. |
| 2003/0153935 A1 | 8/2003 | Mialhe |
| 2003/0171739 A1 | 9/2003 | Murphy et al. |
| 2003/0181942 A1 | 9/2003 | Sutton et al. |
| 2003/0187474 A1 | 10/2003 | Keegan et al. |
| 2003/0191526 A1 | 10/2003 | Van Tassel et al. |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0208227 A1 | 11/2003 | Thomas |
| 2003/0212432 A1 | 11/2003 | Khairkhahan et al. |
| 2003/0220667 A1 | 11/2003 | van der Burg et al. |
| 2004/0034366 A1 | 2/2004 | van der Burg et al. |
| 2004/0049224 A1 | 3/2004 | Buehlmann et al. |
| 2004/0098028 A1 | 5/2004 | Martinez |
| 2004/0098031 A1 | 5/2004 | van der Burg et al. |
| 2004/0117004 A1 | 6/2004 | Osborne et al. |
| 2004/0122467 A1 | 6/2004 | Tassel et al. |
| 2004/0127935 A1 | 7/2004 | Tassel et al. |
| 2004/0153120 A1 | 8/2004 | Seifert et al. |
| 2004/0181237 A1 | 9/2004 | Forde et al. |
| 2004/0215230 A1 | 10/2004 | Frazier et al. |
| 2004/0254594 A1 | 12/2004 | Alfaro |
| 2004/0260317 A1 | 12/2004 | Bloom et al. |
| 2004/0267191 A1 | 12/2004 | Gifford, III et al. |
| 2005/0004652 A1 | 1/2005 | van der Burg et al. |
| 2005/0033409 A1 | 2/2005 | Burke et al. |
| 2005/0038470 A1 | 2/2005 | van der Burg et al. |
| 2005/0043759 A1 | 2/2005 | Chanduszko |
| 2005/0049573 A1 | 3/2005 | Van Tassel et al. |
| 2005/0049681 A1 | 3/2005 | Greenhalgh et al. |
| 2005/0060017 A1 | 3/2005 | Fishell et al. |
| 2005/0065589 A1 | 3/2005 | Schneider et al. |
| 2005/0075665 A1 | 4/2005 | Brenzel et al. |
| 2005/0085843 A1 | 4/2005 | Opolski et al. |
| 2005/0090860 A1 | 4/2005 | Paprocki |
| 2005/0113861 A1 | 5/2005 | Corcoran et al. |
| 2005/0149173 A1 | 7/2005 | Hunter et al. |
| 2005/0177182 A1 | 8/2005 | van der Burg et al. |
| 2005/0192616 A1 | 9/2005 | Callister et al. |
| 2005/0192627 A1 | 9/2005 | Whisenant et al. |
| 2005/0222533 A1 | 10/2005 | Chanduszko et al. |
| 2005/0234540 A1 | 10/2005 | Peavey et al. |
| 2005/0234543 A1 | 10/2005 | Glaser et al. |
| 2005/0246008 A1 | 11/2005 | Hogendijk et al. |
| 2005/0251144 A1 | 11/2005 | Wilson et al. |
| 2005/0256532 A1 | 11/2005 | Nayak et al. |
| 2005/0267524 A1 | 12/2005 | Chanduszko |
| 2005/0288706 A1 | 12/2005 | Widomski et al. |
| 2006/0000443 A1 | 1/2006 | Kado et al. |
| 2006/0004433 A1 | 1/2006 | Greenberg et al. |
| 2006/0009798 A1 | 1/2006 | Callister |
| 2006/0009800 A1 | 1/2006 | Christianson et al. |
| 2006/0020327 A1 | 1/2006 | Lashinski et al. |
| 2006/0036282 A1 | 2/2006 | Wahr et al. |
| 2006/0052816 A1 | 3/2006 | Bates et al. |
| 2006/0122646 A1 | 6/2006 | Corcoran et al. |
| 2006/0149299 A1 | 7/2006 | Greene et al. |
| 2006/0149307 A1 | 7/2006 | Durgin |
| 2006/0149314 A1 | 7/2006 | Borillo et al. |
| 2006/0155323 A1 | 7/2006 | Porter et al. |
| 2006/0173529 A1 | 8/2006 | Blank |
| 2006/0206148 A1 | 9/2006 | Khairkhahan et al. |
| 2006/0210816 A1 | 9/2006 | Finley |
| 2006/0217761 A1 | 9/2006 | Opolski |
| 2006/0229668 A1 | 10/2006 | Prestezog et al. |
| 2006/0276839 A1 | 12/2006 | McGuckin |
| 2007/0027456 A1 | 2/2007 | Gartner et al. |
| 2007/0066993 A1 | 3/2007 | Kreidler |
| 2007/0073247 A1 | 3/2007 | Ewaschuk |
| 2007/0083230 A1 | 4/2007 | Javois |
| 2007/0083232 A1 | 4/2007 | Lee |
| 2007/0088388 A1 | 4/2007 | Opolski et al. |
| 2007/0112382 A1 | 5/2007 | Thill et al. |
| 2007/0123934 A1 | 5/2007 | Whisenant et al. |
| 2007/0129753 A1 | 6/2007 | Quinn et al. |
| 2007/0129757 A1 | 6/2007 | Armstrong |
| 2007/0135826 A1 | 6/2007 | Zaver et al. |
| 2007/0149995 A1 | 6/2007 | Quinn et al. |
| 2007/0167981 A1 | 7/2007 | Opolski et al. |
| 2007/0173885 A1 | 7/2007 | Cartier et al. |
| 2007/0179527 A1 | 8/2007 | Eskuri et al. |
| 2007/0179583 A1 | 8/2007 | Goetzinger et al. |
| 2007/0191884 A1 | 8/2007 | Eskridge et al. |
| 2007/0198059 A1 | 8/2007 | Patel et al. |
| 2007/0213766 A1 | 9/2007 | Ravikumar |
| 2007/0237720 A1 | 10/2007 | Padilla et al. |
| 2007/0270891 A1 | 11/2007 | McGuckin |
| 2007/0276415 A1 | 11/2007 | Kladakis et al. |
| 2008/0039743 A1 | 2/2008 | Fox et al. |
| 2008/0039922 A1 | 2/2008 | Miles et al. |
| 2008/0039929 A1 | 2/2008 | Davis et al. |
| 2008/0119891 A1 | 5/2008 | Miles et al. |
| 2008/0215086 A1 | 9/2008 | Olsen et al. |
| 2008/0249562 A1 | 10/2008 | Cahill |
| 2008/0288042 A1 | 11/2008 | Purdy et al. |
| 2009/0025820 A1 | 1/2009 | Adams |
| 2009/0069840 A1 | 3/2009 | Hallisey |
| 2009/0099596 A1 | 4/2009 | McGuckin, Jr. et al. |
| 2009/0105747 A1 | 4/2009 | Chanduszko et al. |
| 2009/0112050 A1 | 4/2009 | Farnan et al. |
| 2009/0112249 A1 | 4/2009 | Miles et al. |
| 2009/0171386 A1 | 7/2009 | Amplatz et al. |
| 2009/0177163 A1 | 7/2009 | King et al. |
| 2009/0182405 A1 | 7/2009 | Arnault De La Menardiere et al. |
| 2009/0192518 A1 | 7/2009 | Golden et al. |
| 2009/0228038 A1 | 9/2009 | Amin |
| 2009/0299338 A1 | 12/2009 | Di Palma |
| 2009/0318948 A1 | 12/2009 | Linder et al. |
| 2010/0191279 A1 | 7/2010 | Kassab et al. |
| 2010/0228279 A1 | 9/2010 | Miles et al. |
| 2010/0228285 A1 | 9/2010 | Miles et al. |
| 2010/0234878 A1 | 9/2010 | Hruska et al. |
| 2010/0262225 A1 | 10/2010 | Schneider et al. |
| 2010/0324585 A1 | 12/2010 | Miles et al. |
| 2010/0324586 A1 | 12/2010 | Mlles et al. |
| 2010/0324587 A1 | 12/2010 | Miles et al. |
| 2010/0324588 A1 | 12/2010 | Miles et al. |
| 2011/0022079 A1 | 1/2011 | Miles et al. |
| 2011/0046658 A1 | 2/2011 | Connor et al. |
| 2011/0054515 A1 | 3/2011 | Bridgeman et al. |
| 2011/0208233 A1 | 8/2011 | McGuckin, Jr. et al. |
| 2012/0316584 A1 | 12/2012 | Miles et al. |
| 2013/0138138 A1 | 5/2013 | Clark et al. |
| 2013/0178889 A1 | 7/2013 | Miles et al. |
| 2014/0135817 A1 | 5/2014 | Tischler et al. |
| 2014/0142617 A1 | 5/2014 | Larsen et al. |
| 2014/0364941 A1 | 12/2014 | Edmiston et al. |
| 2016/0262767 A1 | 9/2016 | Miles et al. |
| 2016/0278784 A1 | 9/2016 | Edmiston et al. |
| 2017/0156840 A1 | 6/2017 | Edmiston et al. |

FOREIGN PATENT DOCUMENTS

| | | |
|---|---|---|
| CN | 102612345 | 7/2012 |
| CN | 106037852 | 10/2016 |
| DE | 102006056283 | 6/2008 |
| EP | 1266630 | 12/2002 |
| EP | 1358850 | 11/2003 |
| EP | 1523957 | 4/2005 |
| EP | 1741393 | 1/2007 |
| EP | 1768604 | 4/2007 |
| EP | 1659988 | 2/2010 |
| JP | 2007532174 | 11/2007 |
| JP | 2008536620 | 9/2008 |

(56) References Cited

FOREIGN PATENT DOCUMENTS

| JP | 2010500917 | 1/2010 |
|---|---|---|
| JP | 2016-202905 | 12/2016 |
| JP | 2017-502788 | 1/2017 |
| WO | 1999/33402 | 7/1999 |
| WO | 00/27292 | 5/2000 |
| WO | WO 0130266 | 5/2001 |
| WO | 2001/93920 | 12/2001 |
| WO | 2002/071977 | 9/2002 |
| WO | 2003/028802 | 4/2003 |
| WO | 2004045393 | 6/2004 |
| WO | 2004/100803 | 11/2004 |
| WO | 2005053547 | 6/2005 |
| WO | 2005099365 | 10/2005 |
| WO | 2006/033641 | 3/2006 |
| WO | 2006047748 | 5/2006 |
| WO | WO 2006126979 | 11/2006 |
| WO | 2007/054116 | 5/2007 |
| WO | 2007/147145 | 12/2007 |
| WO | WO 2008150346 | 12/2008 |
| WO | 2010/081033 | 7/2010 |
| WO | 2010/148246 | 12/2010 |
| WO | WO 20140708078 | 5/2014 |

OTHER PUBLICATIONS

European Examination Report dated Mar. 2, 2022 for EP App. No. 18185279.9 (4 pages).
European Search Report dated Mar. 4, 2022 for EP App. No. 21214845.6 (7 pages).
Chinese Office Action and Search Report with English Translations dated Jun. 1, 2022 for Chinese App. No. 201810153281.2 (19 pages).
Examiner's Decision of Refusal (Translation) issued in JP 2018-027625 on Jul. 26, 2022.
Abstract of JPH04129549A with English Translation Published Apr. 30, 1992.
Chinese Office Action (English Translation) issued Oct. 24, 2022 for Chinese App. No. 201810153281.2 (3 pages).
Extended European Search Report dated Aug. 17, 2020 for EP App. No. 20162101.8 (7 pages).
Office Action and English Translation issued in CN Patent App. No. 201610236526.9 on Sep. 3, 2020 (9 Pages).
Extended European Search Report dated Jun. 16, 2020 for EP App. No. 20160043.4 (10 pages).
European Search Report dated May 19, 2020 for EP App. No. 20159409 (8 Pages).
English Abstract and English machine translation of the Specification and Claims of DE 102006056283 dated 2008-06-05.
Office Action and English Translation issued in JP2012-516313 on Mar. 25, 2014.
International Search Report dated Feb. 7, 2013 for International Application No. PCT/US2012/063074 (5 pages).
International Search Report dated Apr. 26, 2010 for International Application No. PCT/US2010/020549 (7 pages).
International Search Report dated May 7, 2010 for International Application No. PCT/US2010/020547 (4 pages).
International Search Report dated May 6, 2010 for International Application No. PCT/US2010/020539 (5 pages).
International Search Report dated Jun. 15, 2009 for International Application No. PCT/US2008/080374 (7 pages).
European Search Report dated Aug. 6, 2018 for EP App. No. 18157669.5 (15 pages).
Supplemental European Search Report dated Jan. 3, 2019 for EP App. No. 18185291.4 (6 pages).

\* cited by examiner

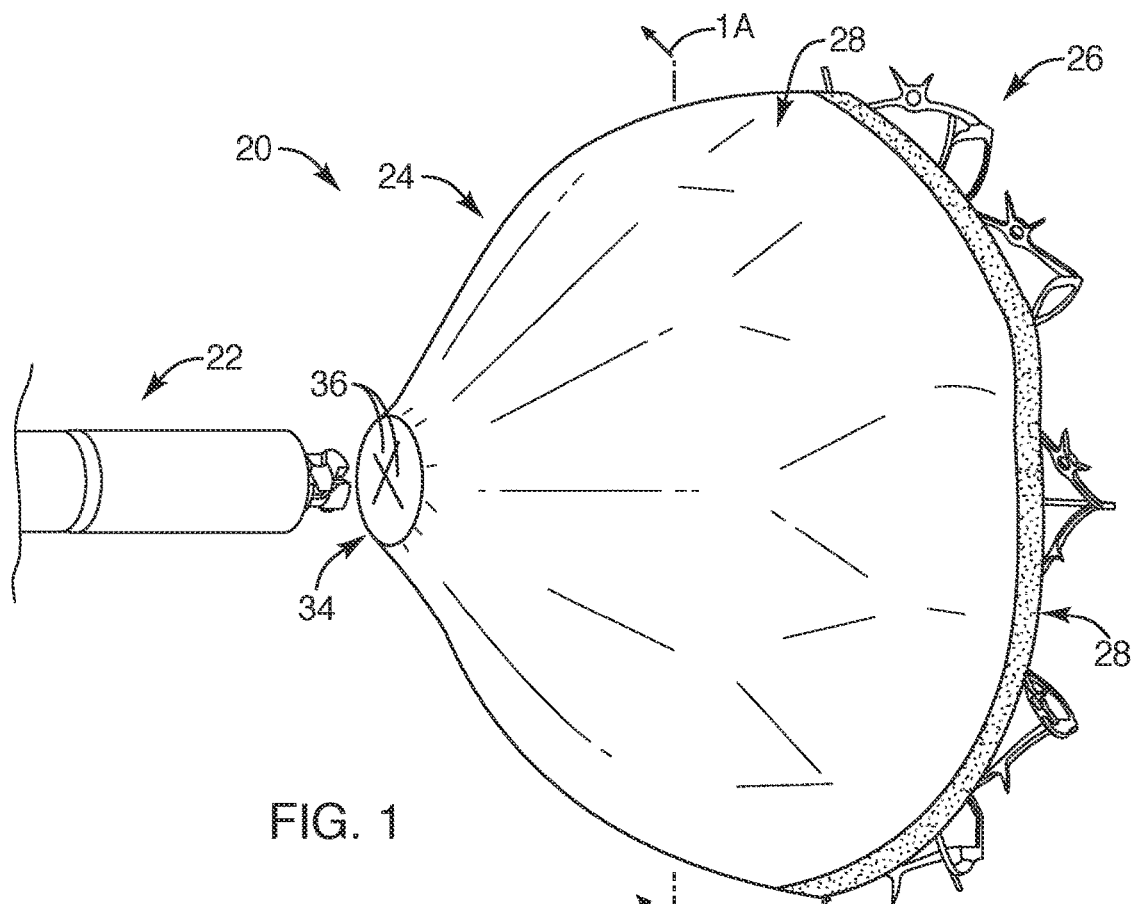
FIG. 1
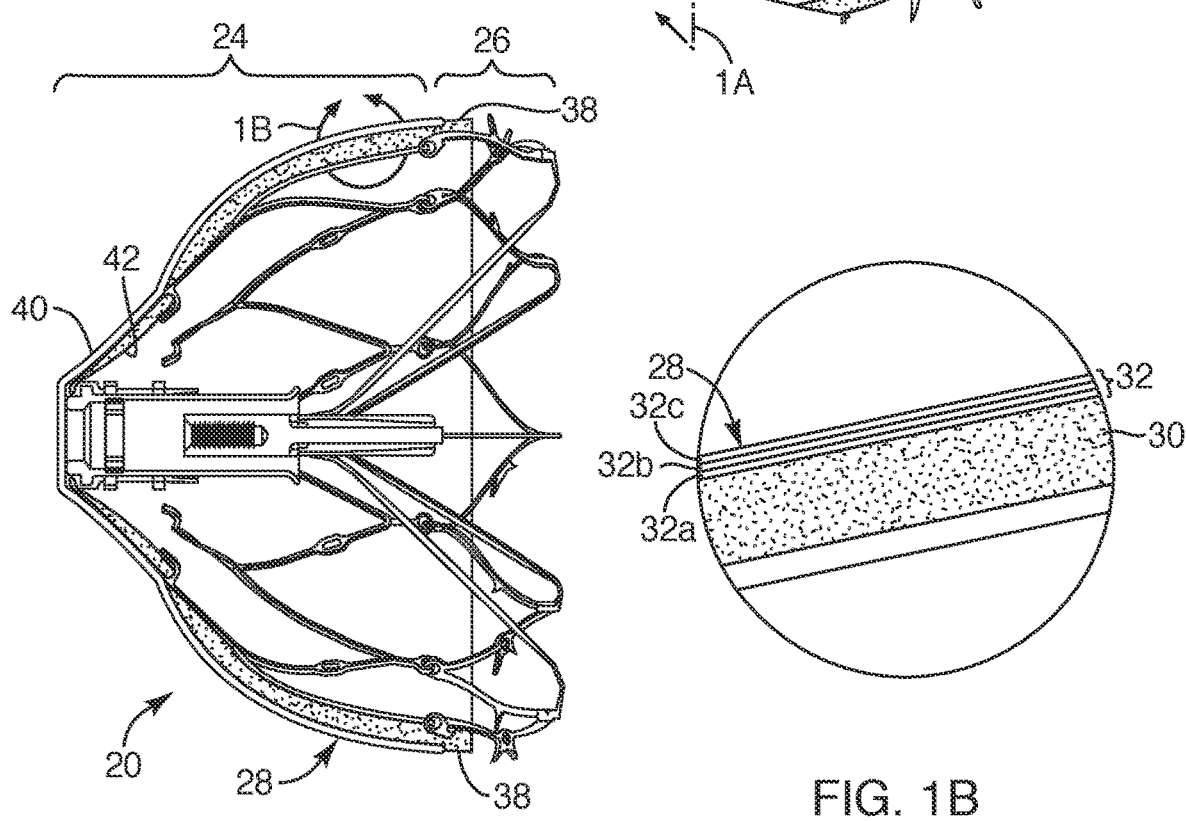
FIG. 1A
FIG. 1B

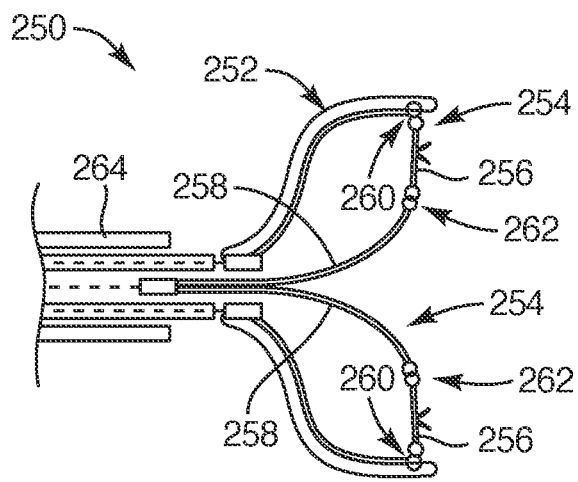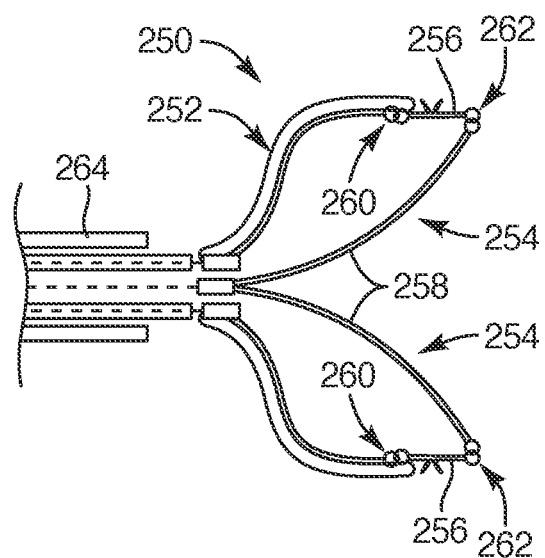
FIG. 16A  FIG. 16B
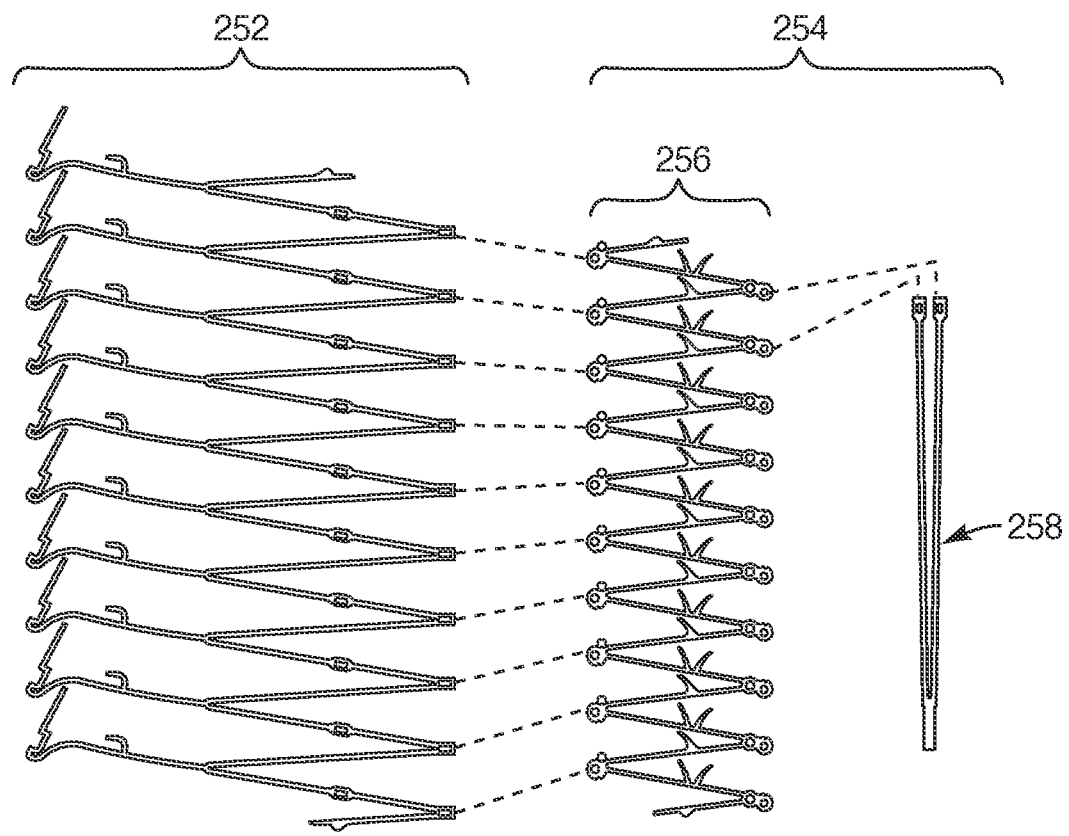
FIG. 17

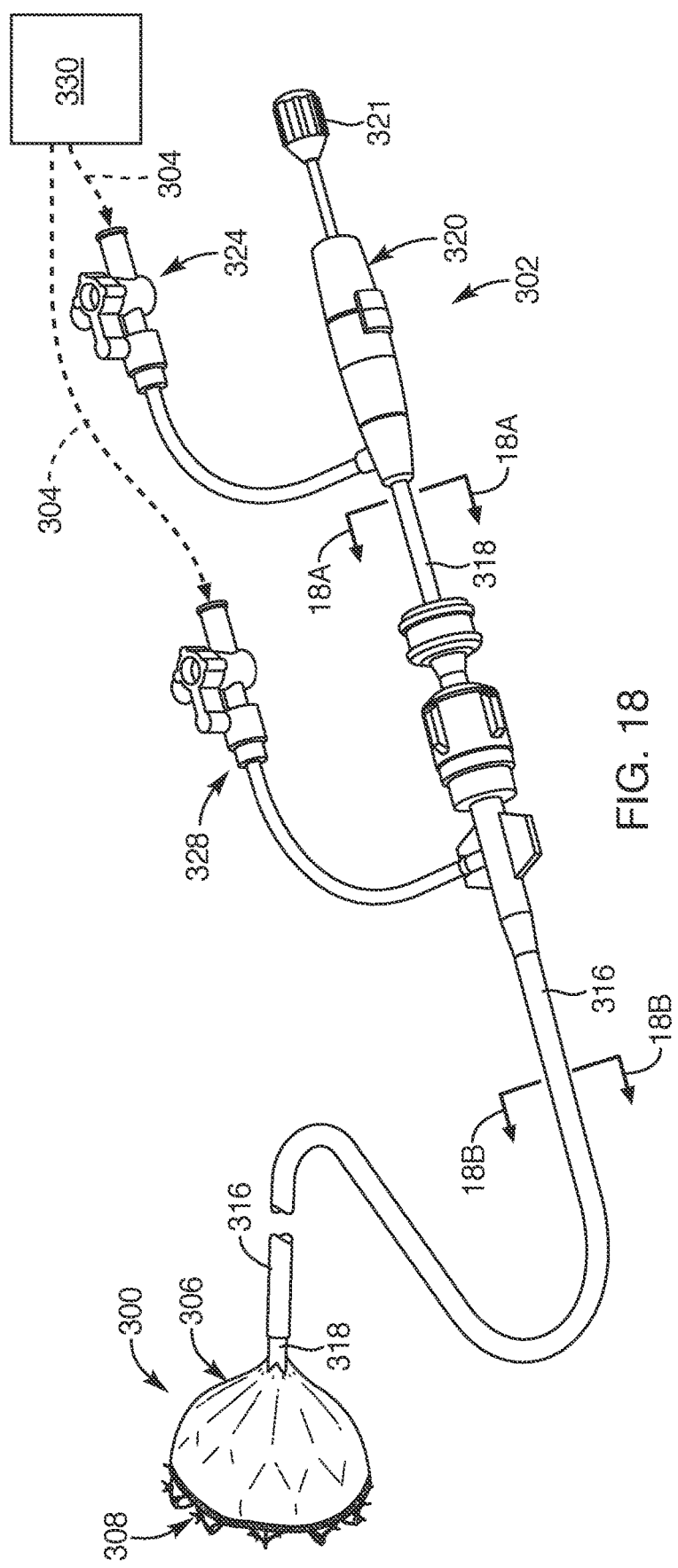
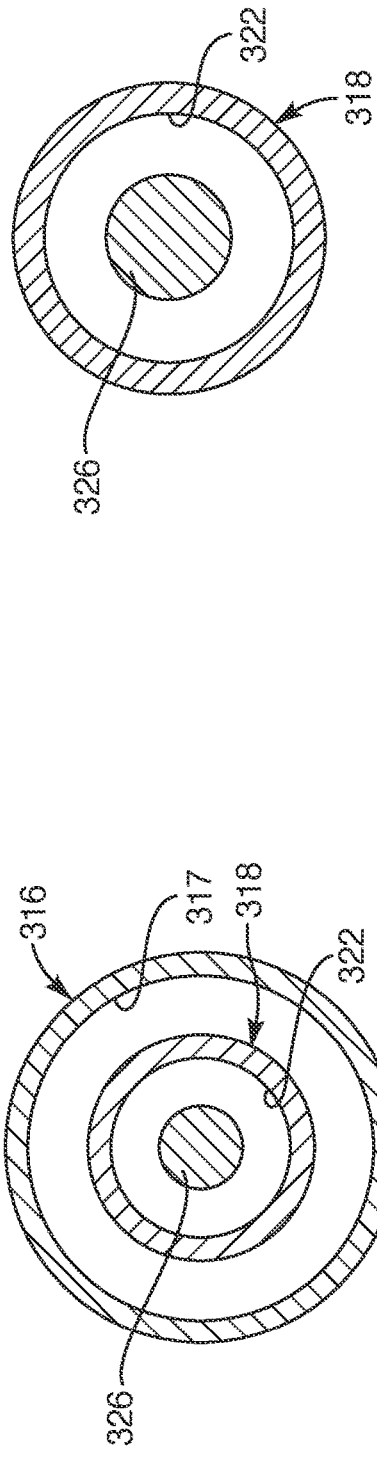
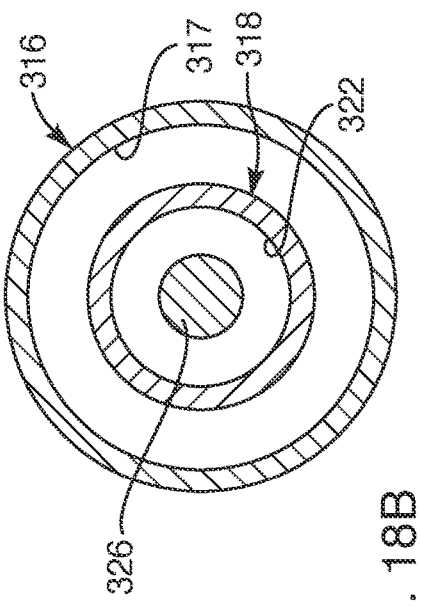
FIG. 18
FIG. 18A
FIG. 18B

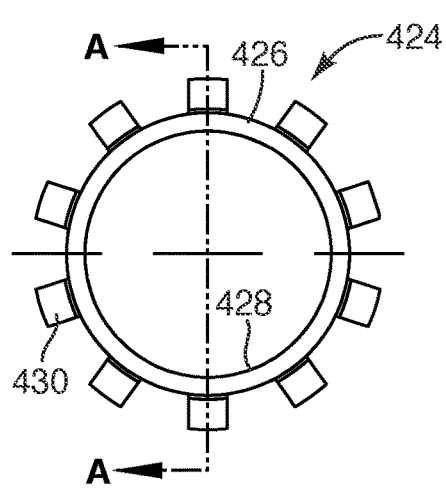
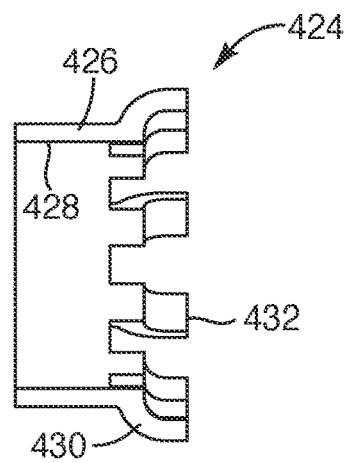
FIG. 25　　　　FIG. 25A
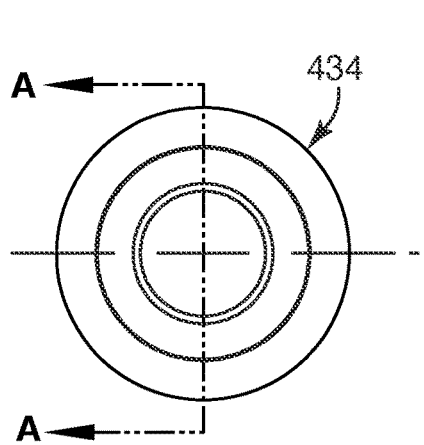
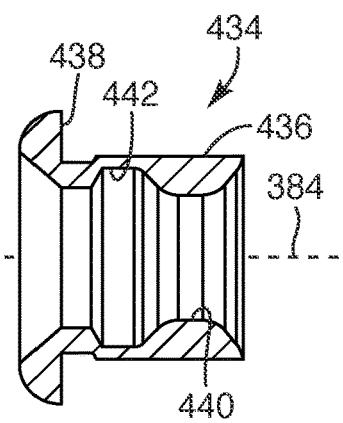
FIG. 26　　　　FIG. 26A
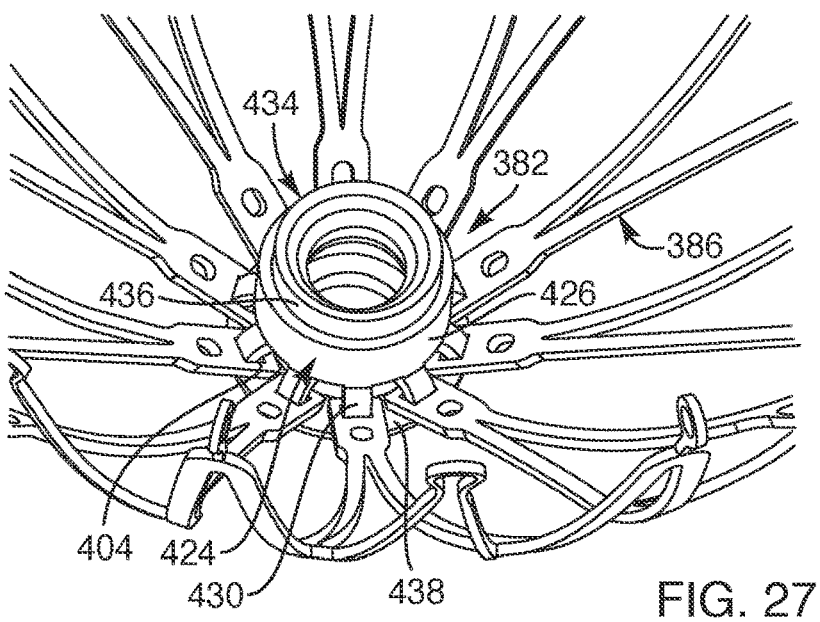
FIG. 27

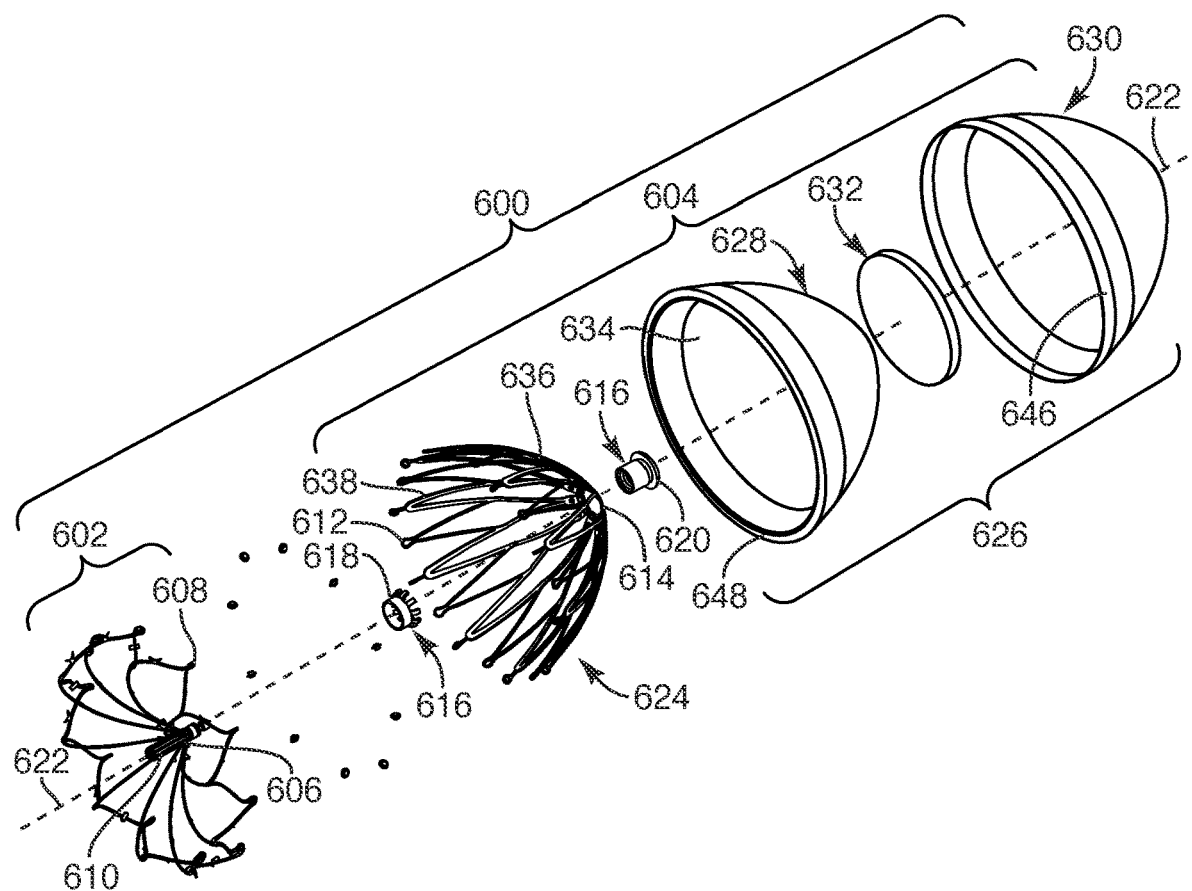
FIG. 36
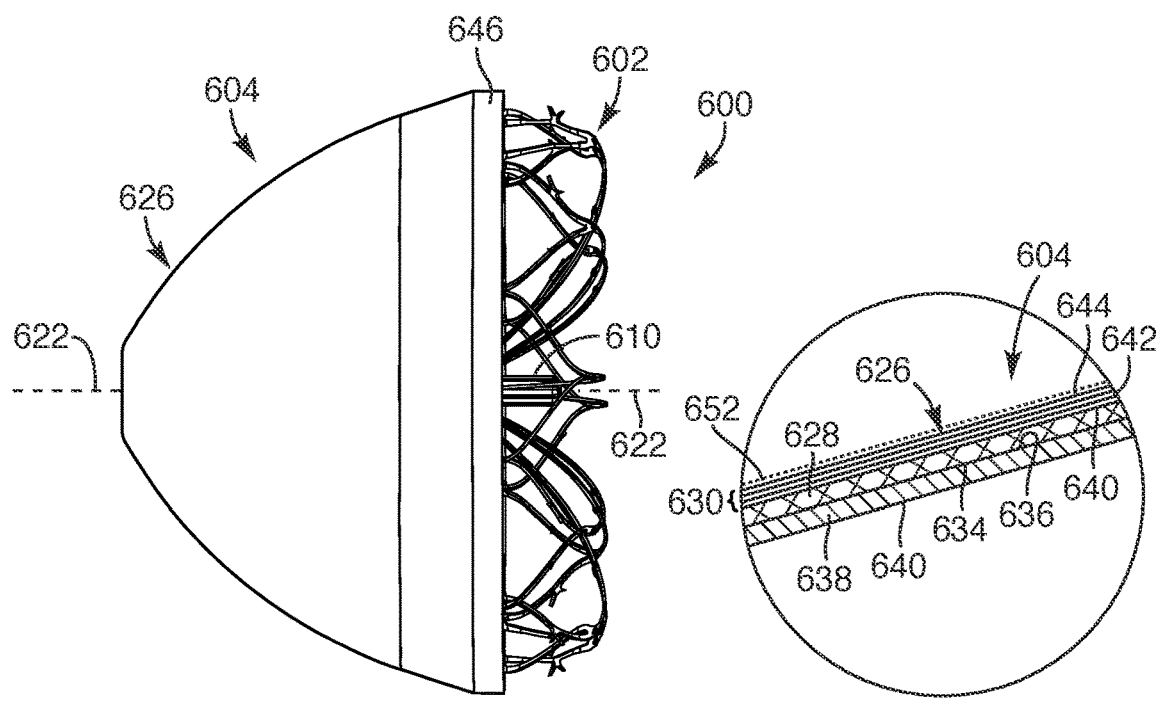
FIG. 37
FIG. 37A

MEDICAL DEVICE FOR MODIFICATION OF LEFT ATRIAL APPENDAGE AND RELATED SYSTEMS AND METHODS

CROSS-REFERENCE TO RELATED APPLICATIONS

The present application is a divisional of U.S. patent application Ser. No. 16/859,282, filed on Apr. 27, 2020, which is a continuation of U.S. patent application Ser. No. 15/438,650, filed on Feb. 21, 2017, now issued as U.S. Pat. No. 10,631,969, which is a continuation-in-part of U.S. patent application Ser. No. 15/094,254, filed Apr. 8, 2016, now issued as U.S. Pat. No. 10,064,628, which claims the benefit of U.S. Provisional No. 62/148,317, filed on Apr. 16, 2015. Further, U.S. patent application Ser. No. 15/094,254 also claims benefit to, and is a continuation-in-part of, U.S. patent application Ser. No. 14/308,695, filed Jun. 18, 2014, now issued as U.S. Pat. No. 9,649,115, which in turn claims benefit to U.S. Provisional Application No. 61/837,628, filed on Jun. 20, 2013. Further, U.S. patent application Ser. No. 14/308,695 claims benefit to, and is a continuation-in-part of, U.S. patent application Ser. No. 13/666,612, filed Nov. 1, 2012, now issued as U.S. Pat. No. 9,693,781, which in turn claims benefit to U.S. Provisional Application No. 61/553,948, filed on Nov. 1, 2011, and U.S. Provisional Application No. 61/661,799, filed on Jun. 19, 2012. Further, the above-listed U.S. patent application Ser. No. 13/666,612 claims benefit to, and is a continuation-in-part of, U.S. patent application Ser. No. 12/818,046, filed on Jun. 17, 2010, now issued as U.S. Pat. No. 8,636,764, which in turn claims benefit to the following U.S. Provisional Patent Applications: U.S. Provisional Application No. 61/345,514, filed on May 17, 2010; U.S. Provisional Application No. 61/325,230, filed on Apr. 16, 2010; U.S. Provisional Application No. 61/320,635, filed on Apr. 2, 2010; U.S. Provisional Application No. 61/294,058, filed on Jan. 11, 2010; and U.S. Provisional Application No. 61/218,018, filed on Jun. 17, 2009. The disclosures of each application listed above are incorporated by reference herein in their entireties.

TECHNICAL FIELD

The present invention relates generally to the occlusion or modification of tissue openings or appendages and, more specifically, to devices, systems and methods for occluding or otherwise structurally altering such openings and appendages including, for example, left atrial appendages.

BACKGROUND

The upper chambers of the heart, the atria, have appendages attached to each of them. For example, the left atrial appendage is a feature of all human hearts. The physiologic function of such appendages is not completely understood, but they do act as a filling reservoir during the normal pumping of the heart. The appendages typically protrude from the atria and cover an external portion of the atria. Atrial appendages differ substantially from one to another. For example, one atrial appendage may be configured as a tapered protrusion while another atrial appendage may be configured as a re-entrant, sock-like hole. The inner surface of an appendage is conventionally trabeculated with cords of muscular cardiac tissue traversing its surface with one or multiple lobes.

The atrial appendages appear to be inert while blood is being pumped through them during normal heart function. In other words, the appendages don't appear to have a noticeable effect on blood pumped through them during normal heart function. However, in cases of atrial fibrillation, when the atria go into arrhythmia, blood may pool and thrombose inside of the appendages. Among other things, this can pose a stroke risk when it occurs in the left appendage since the thrombus may be pumped out of the heart and into the cranial circulation once normal sinus rhythm is restored following arrhythmia events.

Historically, appendages have sometimes been modified surgically to reduce the risk imposed by atrial fibrillation. In recent years devices which may be delivered percutaneously into the left atrial appendage have been introduced. The basic function of these devices is to exclude the volume within the appendage with an implant which then allows blood within the appendage to safely thrombose and then to be gradually incorporated into cardiac tissue. This process, coupled with the growth of endothelium over the face of the device, can leave a smooth, endothelialized surface where the appendage is located. In comparison to surgical procedures, devices implanted percutaneously are a less invasive means for addressing the problems associated with the left atrial appendage.

However, due to the wide variability of the ostium size and volume of the left atrial appendage, current implantable devices conventionally include a structure that cannot meet such variability, resulting in inadequate devices for many left atrial appendage anatomies. Further, such implantable devices are substantially limited by the orientation by which they can successfully be deployed. As such, it would be advantageous to provide a percutaneous system, method and/or device that addresses, for example, the issues of implant orientation, the variability in sizes and shapes of the left atrial appendage, or all of these, in order to provide high success in left atrial appendage modification. It would also be desirable to provide a device, system and method that enables easy positioning and repositioning of the device relative to the structure being modified or occluded including the positioning (or repositioning) of an occluder portion independent of other components or features of the device.

A variety of features and advantages will be apparent to those of ordinary skill in the art upon reading the description of various embodiments set forth below.

BRIEF SUMMARY OF THE INVENTION

Embodiments of the present invention are directed to various devices, systems and methods of occluding an opening in the tissue of a body. For example, in one embodiment, a medical device for implantation in a left atrial appendage of a heart is provided. The medical device includes an occluder portion and an anchor portion. The occluder portion includes a hub that defines an axis, the occluder portion extending between a proximal end coupled to the hub and a distal end defining an occluder eyelet adjacent thereto. The anchor portion extends between a first end and a second end, the first end coupled to an anchor hub and the second end defining an anchor eyelet adjacent thereto and hingeably coupled to the occluder eyelet. With this arrangement, the anchor hub is moveable along the axis to move the anchor portion between a retracted position and a deployed position upon the occluder portion being in an expanded position.

In another embodiment, the anchor portion extends with anchor frame segments, the anchor frame segments including anchoring tines extending therefrom. In a further embodiment, the anchoring tines extend with an acute angle relative to the anchor frame segments, the acute angle having a range between about 25 degrees and about 60 degrees. In still a further embodiment, the anchoring tines extend with a height relative to the anchor frame segments, the height having a range between about 0.020 inches and about 0.050 inches. In another embodiment, the anchoring tines extending from a single strut are spaced a distance from adjacent tines within a range between about 0.060 inches and 0.015 inches. In yet another embodiment, the anchor frame segments include anchoring tines aligned with and extending from struts defining the anchor frame segments, the struts being non-aligned relative to the axis.

In accordance with another embodiment of the present invention, a medical device for implantation in a left atrial appendage of a heart is provided. In this embodiment, the medical device includes a framework having a proximal end and a distal end and defining an axis. The framework extends between a primary hub and a secondary hub, the primary hub and the secondary hub aligned along the axis of the framework such that the proximal end of the framework is coupled to the primary hub. The framework extends radially outward and distally from the primary hub and extends radially inward and proximally toward the secondary hub such that the secondary hub is positioned proximal the distal end of the framework.

In another embodiment, the framework includes anchoring tines extending therefrom. In a further embodiment, the anchoring tines extend with an acute angle relative to struts of the framework, the acute angle having a range between about 25 degrees and about 60 degrees. In still another further embodiment, the anchoring tines extend with a height relative to struts of the framework, the height having a range between about 0.020 inches and about 0.050 inches. In another embodiment, the anchoring tines extending from a given strut of the framework are spaced a distance from adjacent tines within a range between about 0.060 inches and 0.015 inches.

In another embodiment, the framework includes anchoring tines aligned with and extending from struts of the framework, the struts being non-aligned relative to the axis. In another embodiment, the framework includes occluder frame segments and anchor frame segments, the anchor frame segments hingeably coupled to the occluder frame segments. In a further embodiment, the anchor frame segments are moveable between a retracted position and a deployed position upon the occluder frame segments being in an expanded position.

In another embodiment, the framework includes a tissue growth member positioned over at least a proximal side of the framework. In still another embodiment, the framework includes a tissue growth member including at least one of a fabric material and ePTFE. In a further embodiment, the tissue growth member includes a hydrophilic coating.

In accordance with another embodiment of the present invention, a method for occluding a left atrial appendage is provided. The method includes the step of positioning a framework within the left atrial appendage, the framework having a proximal end and a distal end and defining an axis, the framework extending between a primary hub and a secondary hub, the primary hub and the secondary hub aligned along the axis of the framework, the proximal end of the framework coupled to the primary hub, the framework extending radially outward and distally from the primary hub and extending radially inward and proximally toward the secondary hub such that the secondary hub is positioned proximal the distal end of the framework.

In another embodiment, the method further includes the step of securing the framework to tissue within the left atrial appendage with anchoring tines extending from anchor frame segments of the framework. In another embodiment, the method further includes the step of pivoting anchor frame segments of the framework between a retracted position and a deployed position.

BRIEF DESCRIPTION OF THE SEVERAL VIEWS OF THE DRAWINGS

The foregoing and other advantages of the invention will become apparent upon reading the following detailed description and upon reference to the drawings in which:

FIG. 1 is a perspective view of a medical device and a distal portion of a delivery system, according to one embodiment of the present invention;

FIG. 1A is a partial cross-sectional view of the medical device, taken along section line 1A of FIG. 1, according to another embodiment of the present invention;

FIG. 1B is an enlarged section view of an occluder portion, taken from detail 1B of FIG. 1A, according to another embodiment of the present invention;

FIGS. 16A and 16B are simplistic side profile views of another embodiment of a medical device, depicting the medical device in an anchor non-deployed position and an anchor deployed position, respectively, according to the present invention;

FIG. 17 is a top view of the occluder portion and the anchor portion of the medical device of FIGS. 15A and 15B, depicting frame components cut from a flat sheet, according to another embodiment of the present invention;

FIG. 18 is a perspective view of a medical device delivery system, depicting a medical device attached and deployed at a distal end of the delivery system, according to another embodiment of the present invention;

FIG. 18A is a cross-sectional view of section 18A of FIG. 18, depicting a lumen defined in a proximal portion of a catheter of the delivery system, according to another embodiment of the present invention;

FIG. 18B is a cross-sectional view of section 18B of FIG. 18, depicting a sheath lumen of a sheath with the catheter of the delivery system therein, according to another embodiment of the present invention;

FIG. 25 is a front view of an occluder hub retainer, according to another embodiment of the present invention;

FIG. 25A is a cross-sectional view taken along section A-A of FIG. 25, according to another embodiment of the present invention;

FIG. 26 is a front view of an occluder hub portion, according to another embodiment of the present invention;

FIG. 26A is a cross-sectional view taken along section A-A of FIG. 26, according to another embodiment of the present invention;

FIG. 27 is an enlarged perspective view of an occluder hub, depicting the occluder frame coupled to the occluder hub, according to another embodiment of the present invention;

FIG. 36 is an exploded view of a medical device, according to another embodiment of the present invention;

FIG. 37 is a side view of the assembled medical device of FIG. 36, according to another embodiment of the present invention; and FIG. 37A is an enlarged cross-sectional view of an occluder portion, depicting layers of an occluder material positioned over the occluder frame portion, according to another embodiment of the present invention.

DETAILED DESCRIPTION OF THE INVENTION

Figure 2:
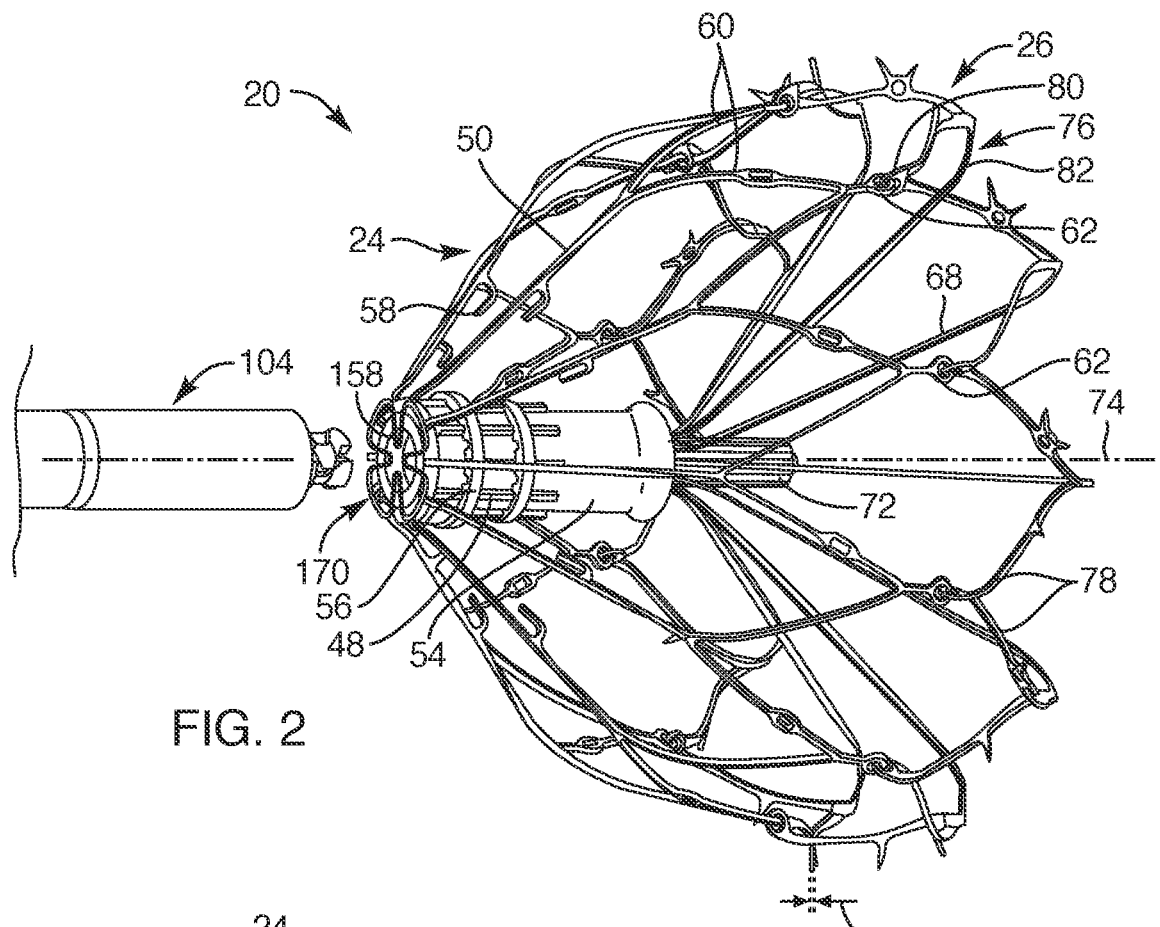
FIG. 2 is a perspective view of the medical device of FIG. 1, depicting the frame without its tissue growth member, according to another embodiment of the present invention.

Referring first to FIGS. 1 and 1A, a medical device 20 and a distal end portion of a delivery system 22 is provided. The medical device 20 and delivery system 22 may be employed in interventional procedures for percutaneously closing and modifying an opening or cavity such as, for example, a left atrial appendage ("LAA") within a heart (not shown). The medical device 20 may include frame components of an occluder portion 24 and an anchor portion 26, the occluder portion 24 also including a tissue growth member 28 attached thereto. Further, the anchor portion 26 may be hingably coupled to the occluder portion 24 such that the anchor portion 26 may be actuated, upon deployment of the occluder portion 24, between a deployed position and a non-deployed position (not shown) via an actuation mechanism at a handle (not shown) of the delivery system 22. With this arrangement, the medical device 20 and delivery system 22 may provide functionality of separating the steps of deploying the occluder portion 24 and the anchor portion 26, thereby, providing additional and enhanced functionality to the physician to properly position and implant the medical device 20 in the LAA.

As set forth, the occluder portion 24 may include an occluder material or a tissue growth member 28 attached thereto. The tissue growth member 28 may be a porous material, or other cell attaching material or substrate, configured to promote endothelization and tissue growth thereover. The tissue growth member 28 may extend over a proximal side of the medical device 20 and, particularly, over the occluder portion 24 and may extend over a portion of the anchor portion 26 and hinges coupling the anchor portion 26 to the occluder portion 24. As such, due to the shape of the frame components of the occluder portion 24, the tissue growth member 28 may include a proximal face that is generally convex to form an outer surface 40. The tissue growth member 28 may also include an inner surface 42 on its distal side that is generally concave shaped. In one embodiment, the tissue growth member 28 may extend primarily over an outside surface of frame components of the occluder portion 24 with a portion of the tissue growth member 28 extending on both the outside surface and the inside surface of the frame components of the occluder portion 24. In another embodiment, the tissue growth member 28 may extend primarily over both the outside surface and the inside surface of the frame components of the occluder portion 24 of the medical device 20. In another embodiment, the tissue growth member 28 may extend solely over the outside surface of the frame components of the occluder portion 24.

With respect to FIGS. 1A and 1B, the tissue growth member 28 may include one or more types of materials and/or layers. In one embodiment, the tissue growth member 28 may include a first material layer 30 and a second material layer 32. The first material layer 30 may primarily be an underside layer or base layer of the tissue growth member 28. The first material layer 30 may include porous and conformable structural characteristics. For example, the first material layer 30 may include a foam type material, such as, a polyurethane foam or any other suitable polymeric material, such as a polymer fabric, woven or knitted. The second material layer 32 may include one or more layers of, for example, an expanded polytetrafluoroethylene (ePTFE) material. The second material layer 32 may be attached to an outer surface of the first material layer 30 with, for example, an adhesive. In one embodiment, the second material layer 32 may include a first layer 32A, a second layer 32B, and a third layer 32C such that the first layer 32A may be directly attached to the first material layer 30 and the third layer 32C may be an outer-most layer covering the proximal side of the medial device 20 with the second layer 32B extending therebetween. The various layers of the second material layer 32 may be bonded together by adhesives and/or by a thermal bonding heat process or other appropriate processes known in the art. In one particular example, the outer-most layers, such as the second and third layers 32B, 32C, may be formed of an ePTFE material having an internodal distance (sometimes referred to as pore size) of approximately 70 μm to approximately 90 μm. The first layer 32A of the second material layer 32, adjacent the first material layer 30, may be formed of an ePTFE material having a reduced internodal distance relative to the second and third layers 32B, 32C. For example, the internodal distance of the first layer 32A may be approximately 10 μm. This first layer 32A may be bonded or adhered to the first material layer 30 using an adhesive material. Any other suitable sized layers of ePTFE may be employed, such as ePTFE having an internodal distance up to about 250 μm. Further, there may be one or more additional layers, similarly sized to the first layer 32A, extending over a hub end 34 with flaps 36 (outlined with an "X" configuration) where the delivery system 22 interconnects with the medical device 20 (see FIG. 1).

The second material layer 32 made of ePTFE effectively prevents the passage of blood, due to the small internodal distance and pore size of the first layer 32A, while the larger internodal distance of other layers (e.g., 32B and 32C) enable tissue in-growth and endothelization to occur. Additionally, the first material layer 30, being formed of a polyurethane foam, enables aggressive growth of tissue from the LAA wall into the tissue growth member 28 at the inside or concave side of the medical device 20. Further, the first material layer 30 provides an exposed shelf 38 on the outer surface 40 around the periphery and distal end portion of the tissue growth member 28, which promotes aggressive fibroblast and tissue growth to further initiate endothelization over the outer surface 40 of the second material layer 32. It is noted that the use of appropriate adhesive materials between the first material layer 30 and the next adjacent layer 32A may also serve to fill in the pores of the next adjacent layer 32A and further inhibit possible flow of blood through the tissue growth member 28. Additional layers of ePTFE may also be included to the second material layer 32 of the tissue growth member 28.

Figure 3:
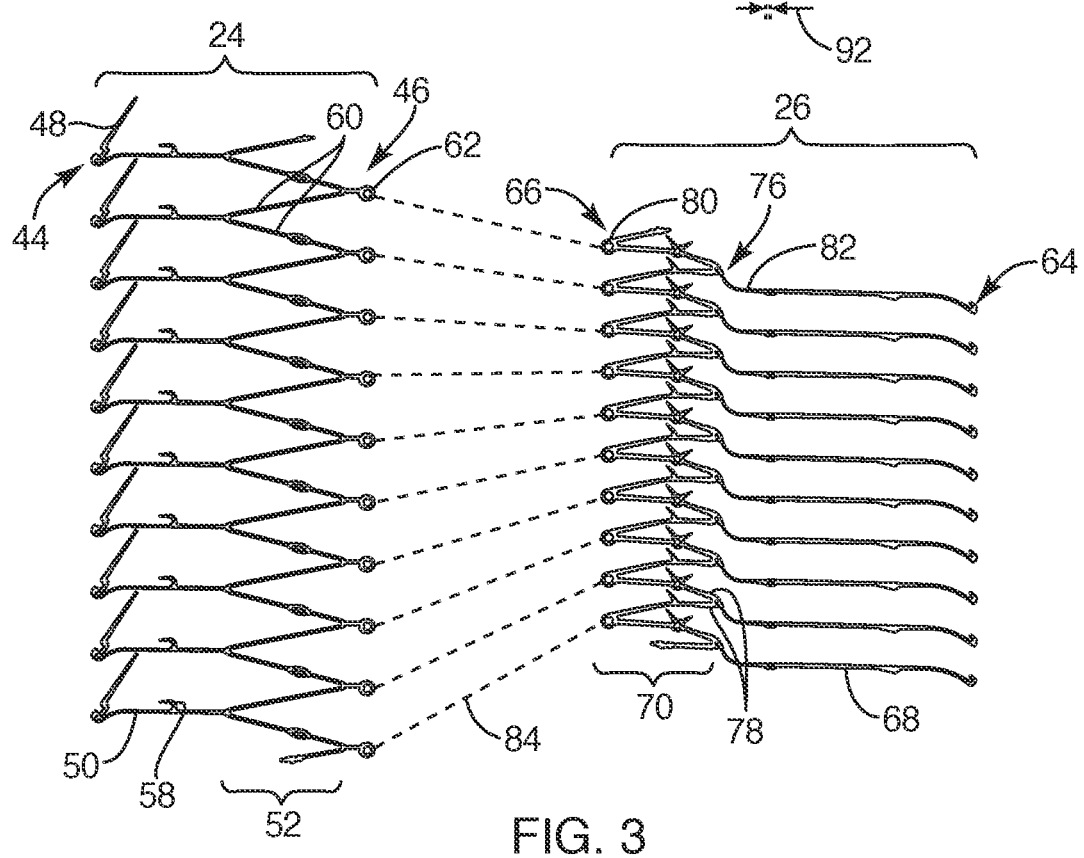
FIG. 3 is a top view of frame components of the occluder portion and the anchor portion of the medical device of FIG. 2, depicting frame components laser cut from a flat sheet prior to being assembled, according to another embodiment of the present invention.

With reference to FIGS. 2 and 3, description of the medical device 20 and its frame components will now be provided. FIG. 2 depicts the frame components in an assembled and fully deployed state and FIG. 3 depicts the frame components as cut from a flat sheet. As previously set forth, the medical device 20 includes an occluder portion 24 and an anchor portion 26. The occluder portion 24 may include multiple occluder frame segments that may be interconnected to form the occluder portion 24. The occluder portion 24 may extend between a first end 44 and a second end 46 with face struts 50 and an occluder zig-zag portion 52 therebetween. Further, the occluder portion 24 includes base extensions 48 extending from the first end 44. The base extensions 48 may be coupled to a hub 54 via rings 56 with notches defined at an inner diameter in the rings 56. Each base extension 48 may extend from a proximal most portion of the occluder portion 24 or first end 44, the first end 44 being one end of each base extension 48 and face strut 50. Each base extension 48 may be sized and configured to be positioned around the hub 54 and held by one or more rings 56. Each base extension 48, at the first end 44, may extend to one face strut 50 of the occluder portion 24, the face strut 50 extending radially and distally from the first end 44. Each face strut 50 may include an extension 58 on a back side thereof, the extension 58 having a hook configuration sized and configured to hold a portion of the tissue growth member (not shown). Further, each face strut 50 extends to a v-extension 60 of the occluder zig-zag portion 52 such that distal ends of each v-extension 60 may be coupled to distal ends of adjacent v-extensions 60 (side-by-side) to define the occluder zig-zag portion 52. The occluder zig-zag portion 52 may enlarge radially and distally from the face struts 50 to a distal end or the second end 46 of the occluder portion 24. At the second end 46, the occluder portion 24 may include an occluder eyelet 62 sized configured to hingably couple to the anchor portion 26.

The anchor portion 26 may include multiple anchor frame segments that may be interconnected to form the anchor portion 26. The anchor portion 26 may extend between a first end 64 and a second end 66 with anchor actuator arms 68 and an anchor zig-zag portion 70 therebetween. The anchor actuator arms 68 may extend between the first end 64 and the anchor zig-zag portion 70. Each anchor actuator arm 68 may be configured to couple to a collar arrangement or splined sleeve 72 at the first end 64 of the anchor portion 26 such that the anchor actuator arms 68 are coupled as a unit or together via the splined sleeve 72. The splined sleeve 72 may be configured to actuate along an axis 74 of the medical device 20 to move the anchor portion 26 between the anchor deployed position and anchor non-deployed position (not shown), discussed in more detail hereafter.

Figure 3A:
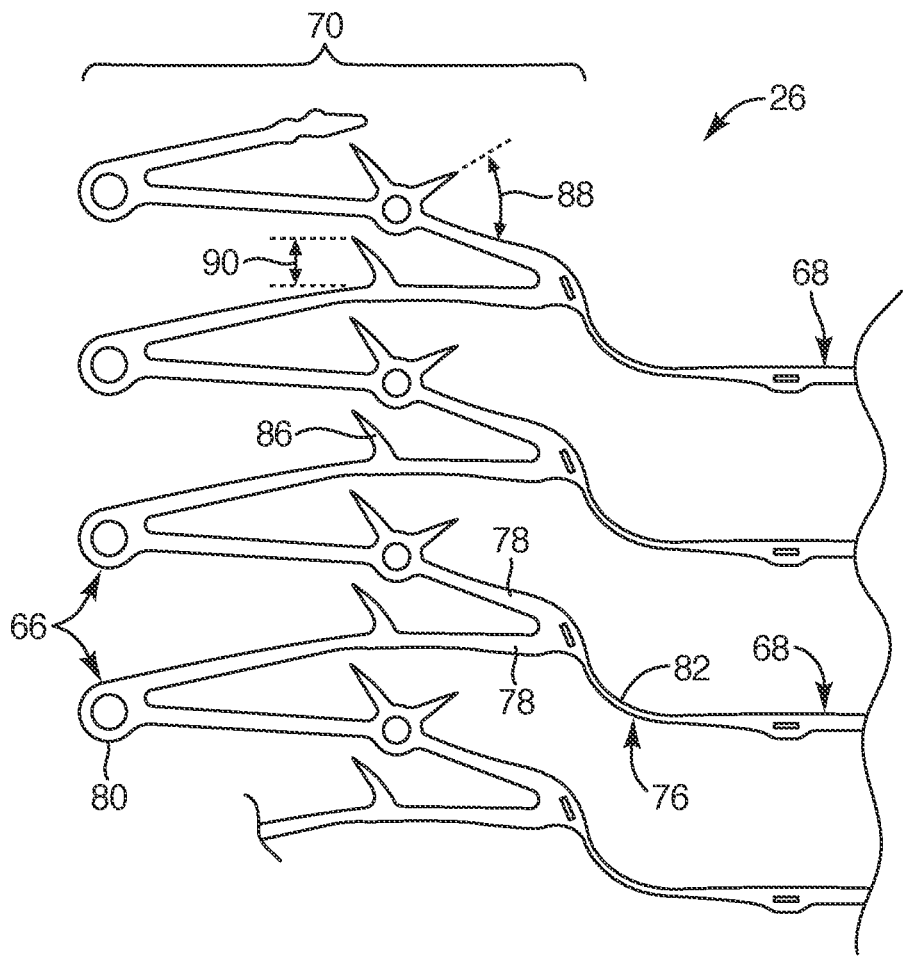
FIG. 3A is a partial enlarged view of the anchor portion depicted in FIG. 3, according to another embodiment of the present invention.

With reference now to FIGS. 2, 3, and 3A, the anchor actuator arms 68 may also include a flexure portion 76. The flexure portion 76 defines a taper 82 and radius extending along the radial length of the flexure portion 76 toward the anchor zig-zag portion 70 and then widens again at the anchor zig-zag portion 70. Such taper 82 along the radial length in the flexure portion 76 facilitates repetitious movement of the anchor portion 26 between the deployed position and the non-deployed position while also maintaining structural integrity of the anchor portion 26, and minimizing the stress and strain in the flexure portion 76 while facilitating a tight radius or loop. In one embodiment, the anchor actuator arms 68 may each include a coil (not shown) that may be wound around a portion of the actuator arm and over the flexure portion 76 with the ends of the coil secured to the anchor actuator arm 68. Such coil may substantially capture the anchor actuator arm 68 from extending in undesirable locations in the LAA should there be a facture or break in the anchor actuator arm 68.

Each flexure portion 76 of the anchor actuator arms 68 may extend to anchor v-extensions 78 such that the proximal ends of each anchor v-extension 78 may be coupled to proximal ends of adjacent anchor v-extensions 78 (similar to the occluder zig-zag portion 52) to form the anchor zig-zag portion 70. At the interconnection of the proximal ends of the anchor v-extensions 78 or the second end 66 of the anchor portion 26, such proximal ends define an anchor eyelet 80. The anchor eyelet 80 may be sized and configured to hingably couple to a corresponding occluder eyelet 62 of the occluder portion 24, as shown by dotted lines 84 (see FIG. 3).

With respect to FIG. 3A, the anchor struts or anchor v-extensions 78 of the anchor zig-zag portion 70 may include one or more hooks 86 or barbs that may extend at an acute angle 88 from the anchor portion 26 or anchor v-extensions and remote from the occluder portion 24. Such acute angle 88 may range between about forty-five degrees and about sixty degrees. Further, the hooks 86 may extend from the anchor v-extensions 78 with a predetermined height 90 so as to provide effective engagement with a tissue wall within the LAA, but not to the extent of piercing all the way through the tissue wall to cause effusions in the LAA. The hooks also include a thickness 92 (see FIG. 2). Such thickness 92 may be similar to the thickness of sheet material from which the fame components (i.e., occluder portion 24 and anchor portion 26) of the medical device 20 are cut.

With respect to FIG. 3, the occluder portion 24 and the anchor portion 26 are depicted in a pre-formed state subsequent to being laser cut from a flat sheet or sheet material of, for example, super elastic material, such as Nitinol. As such, the occluder portion 24 and the anchor portion 26, in the pre-formed state, may be substantially planar and flat, after which, the frame components of the occluder portion 24 and/or the anchor portion 26 may then be heat-set to a desired shape and configuration, as known to one of ordinary skill in the art, similar to the fully deployed configuration (see FIG. 2). Further, as known to one of ordinary skill in the art, other processes may be employed, such as chemical etching and electro-polishing of the frame components. The occluder portion 24 may include ten face struts 50 and ten base extensions 48 with ten occluder eyelets 62 extending from the occluder zig-zag portion 52. Similarly, the anchor portion 26 may include ten anchor actuator arms 68 with ten anchor eyelets 80 extending from the anchor zig-zag portion 70. It should be noted that the occluder portion 24 and anchor portion 26 may include more or less frame components, such as the respective face struts 50 and anchor actuator arms 68, as known to one of ordinary skill in the art. As shown by dotted line 84, occluder eyelets 62 may be configured to couple to corresponding anchor eyelets 80 with a hinge-like coupling arrangement. Such may be employed by directly interlocking the occluder eyelets 62 with the anchor eyelets 80, as depicted in FIG. 2.

In another embodiment, the fame components of the occluder portion 24 and the anchor portion 26 may be laser cut from tubular material, rather than a flat sheet. In this embodiment, the frame components may be laser cut, and then heat set to the desired configuration, similar to that shown in FIG. 2. Various frame components of the occluder portion 24 and the anchor portion 26 may need to be modified as readily understood by one of ordinary skill in the art.

Figure 3B:
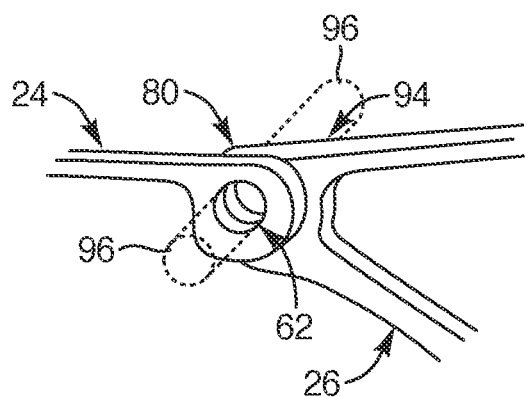
FIG. 3B is an enlarged view of a hinged coupling between the occluder portion and the anchor portion of the medical device, according to another embodiment of the present invention.

With reference to FIG. 3B, in another embodiment, the occluder portion 24 and the anchor portion 26 may be hingably coupled together by aligning the occluder eyelets 62 with the anchor eyelets 80 and positioning an individual interlocking piece 94 (shown in outline) within and through each of the respective aligned eyelets 62, 80. Such an interlocking piece 94 may be a polymeric filament or the like. Ends 96 of the interlocking piece 94 may be heated to form a bulbous shape (not shown) at the ends 96 that, upon cooling, harden and maintain the bulbous shape so as to prevent the respective aligned eyelets from de-coupling. In this manner, the occluder and anchor eyelets 62, 80 may be interlocked via the interlocking piece 94 to provide a hinged coupling arrangement for the anchor portion 26 to pivot relative to the occluder portion 24 and, more particularly, for the anchor portion 26 to pivot about the occluder eyelets 62. In another embodiment, the interlocking piece 94 may be a metallic rivet press fitted through aligned eyelets to provide a hinged coupling arrangement.

Figure 4:
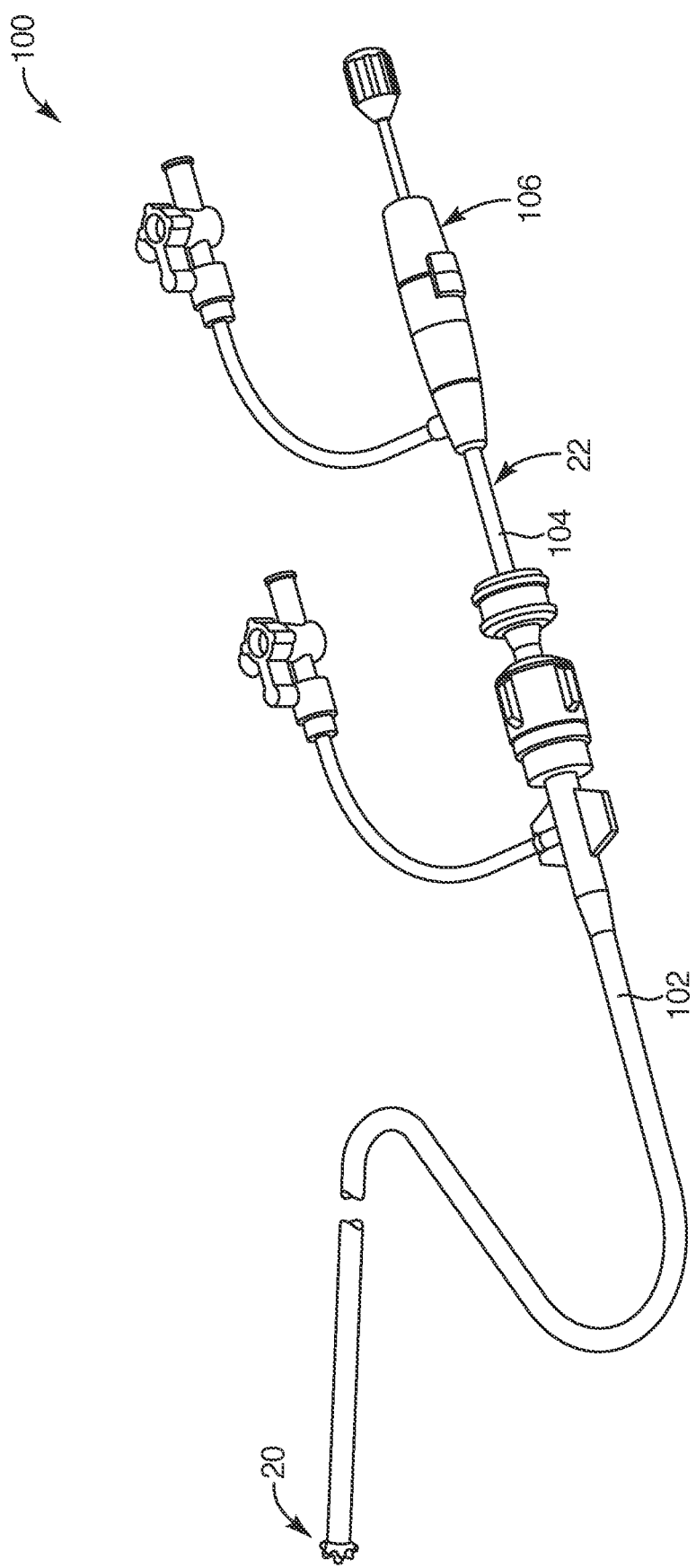
FIG. 4 is a perspective views of a medical device delivery system, according to another embodiment of the present invention.

Now with reference to FIG. 4, a medical device delivery system 100 for delivering the medical device 20 to, for example, the LAA is provided. The medical device delivery system 100 may include the before-mentioned delivery system 22, the medical device 20, and a sheath 102. The delivery system 22 may include a delivery catheter 104 coupled to a handle 106 with the medical device 20 operatively coupled to the handle 106 at a distal end of the delivery catheter 104. The delivery catheter 104 may be sized and configured to be inserted through the sheath 102 such that the medical device 20 may be pushed through the sheath 102 to the distal end thereof. The medical device 20 may be partially exposed, at certain stages of delivery, as depicted. The functionality and detail of the various components of the medical device delivery system 100 will be described in detail hereafter.

Figure 5:
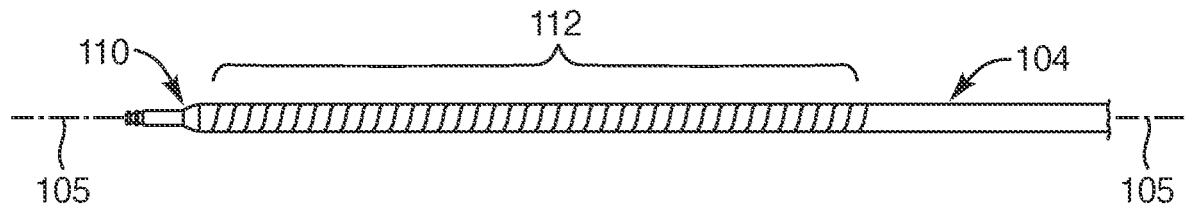
FIG. 5 is a side view of an end portion of a delivery catheter, according to another embodiment of the present invention.
Figure 5A:
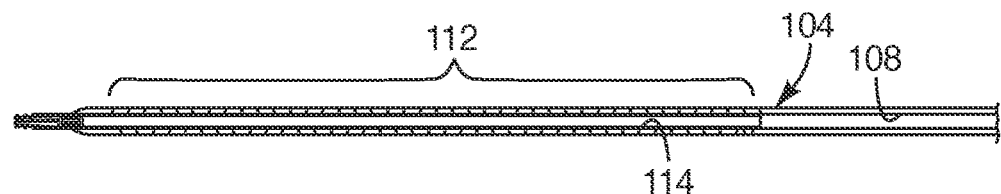
FIG. 5A is a cross-sectional view of the end portion of the delivery catheter, taken along a longitudinal axis of the delivery catheter of FIG. 5, according to another embodiment of the present invention.
Figure 5B:
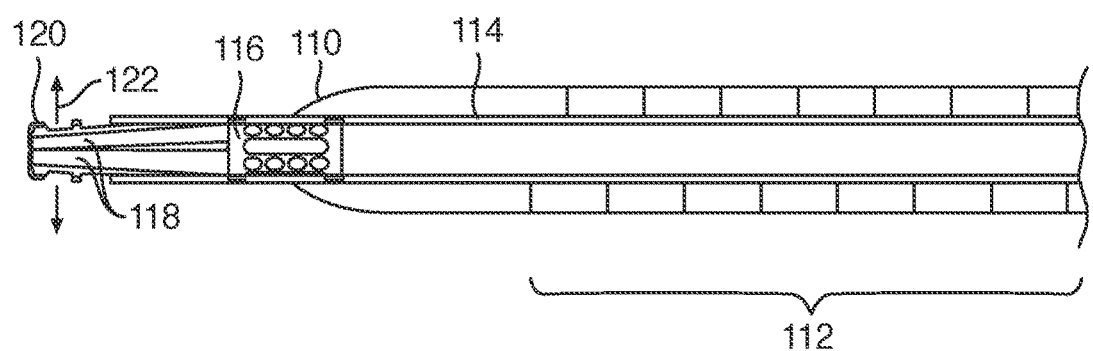
FIG. 5B is an enlarged view of the end portion of the delivery catheter, according to another embodiment of the present invention.

With reference now to FIGS. 5, 5A, and 5B, a distal portion of the delivery catheter 104 will now be described, FIG. 5A being a cross-sectional view of the distal portion of the delivery catheter 104 along an axis 106 thereof depicted in FIG. 5 and FIG. 5B being an enlarged cross-sectional view of a portion of the same. The delivery catheter 104 may define a lumen 108 extending longitudinally therethrough between a proximal end (not shown) and a distal end 110 of the delivery catheter 104. In one embodiment, the delivery catheter 104 may include a shaft (not shown), a spiral cut portion 112, an inner distal tube 114, and a collet 116. Such distal portion of the delivery catheter 104 may include enhanced lateral flexibility along the region of the spiral cut portion 112. That is, the distal portion of the delivery catheter 104 may be more flexible than portions of the delivery catheter 104 more proximal than the spiral cut portion 112. The spiral cut portion 112 may be formed by spirally or helically cutting a slit into the peripheral structure of the distal portion of the delivery catheter 104, as depicted. The inner distal tube 114 may be coupled to the delivery catheter 104 and within the lumen 108 of the distal portion of the delivery catheter 104. The collet 116 may be positioned and thermally coupled to the distal end 110 of the delivery catheter 104 and within the inner distal tube 114 with collet fingers 118 extending distally therefrom. The collet fingers 118 may be sized and configured to latch to the hub of the medical device (not shown) with nubs 120 or protrusions extending from free ends of the collet fingers 118. The collet fingers 118 are moveable outward, as indicated by arrows 122, and are biased to an inward position as shown. The collet 116 and collet fingers 118 may be made from a metallic material, such as stainless steel or Nitinol, or any other suitable metallic material that can maintain a biasing force. Such inward biasing of the collet fingers 118 will be discussed in further detail hereafter. With respect to the enhanced flexibility of the delivery catheter 104 along the spiral cut portion 112, such enhanced flexibility facilitates the medical device to self-center upon being deployed in the LAA. In other words, the radial strength of the medical device (not shown) may be greater than the lateral forces of the delivery catheter 104 along the spiral cut portion 112 to, thereby, allow the medical device to self-center in the LAA in instances where the axis 106 of delivery catheter cannot be made concentric to the ostium of the LAA during delivery and deployment of the medical device.

Figure 6A:
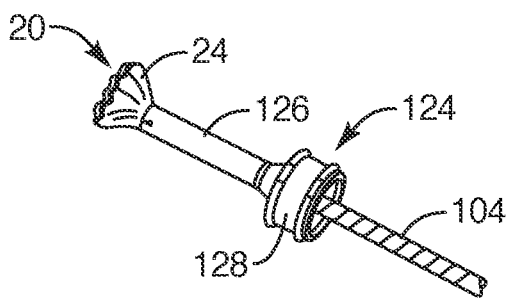
FIGS. 6A-6C are perspective views of a loader, depicting the loader being pushed over an occluder portion of the medical device, the medical device inserted into a sheath, and pushed to a distal end of the sheath, respectively, according to another embodiment of the present invention.
Figure 6B:
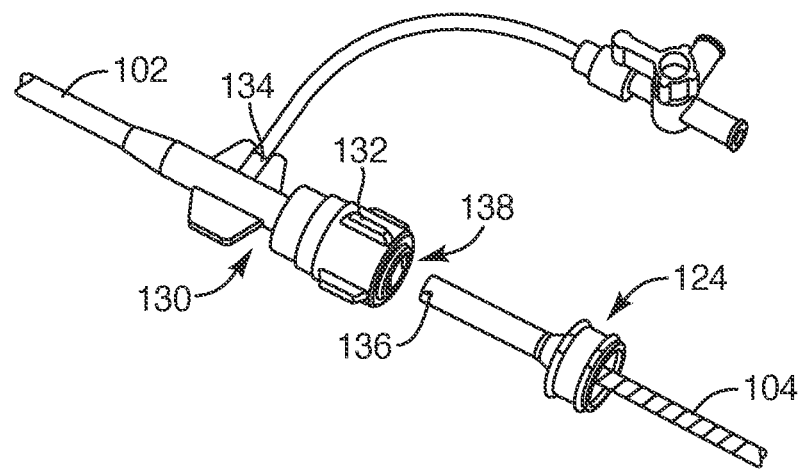
Figure 6C:
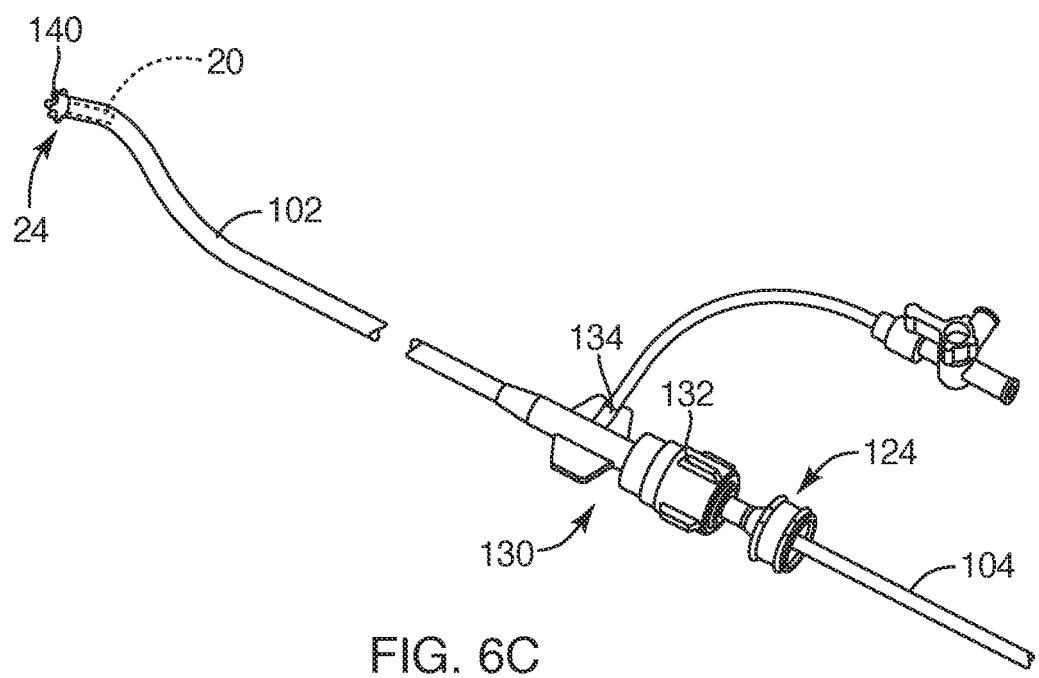
Figure 8:
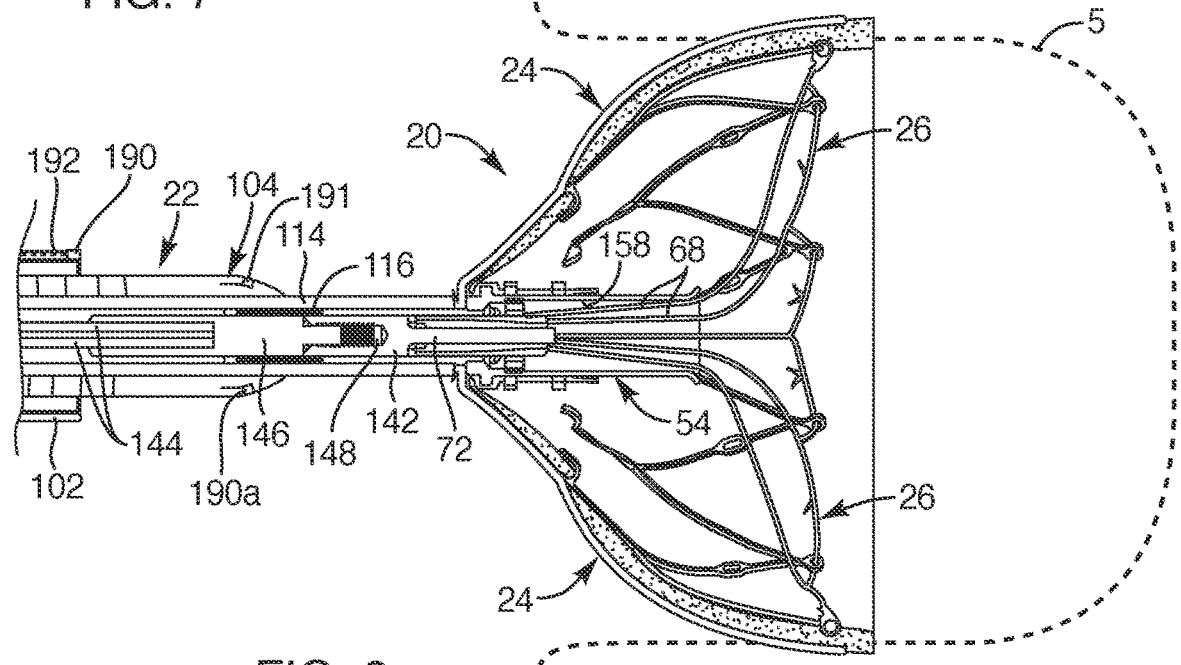
FIG. 8 is a cross-sectional side view of the distal portion of the delivery system and the medical device, depicting a sheath withdrawn to deploy the occluder portion of the medical device in the LAA and depicting the anchor portion in an anchor non-deployed position, according to another embodiment of the present invention.
Figure 8A:
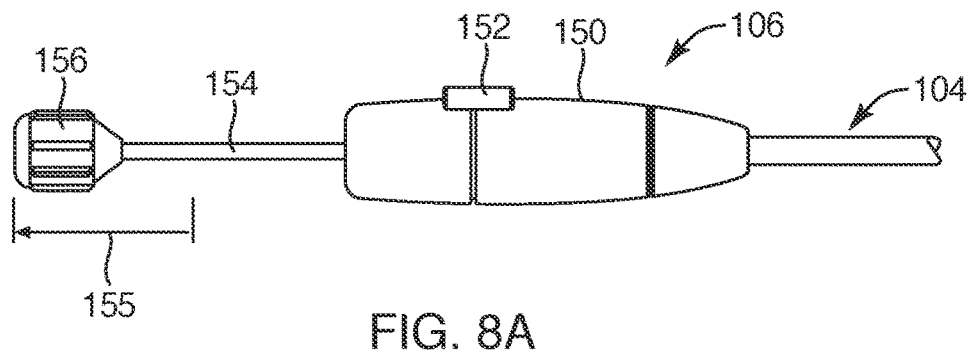
FIG. 8A is a side view of a handle, depicting the handle in a first position corresponding to the anchor non-deployed position, according to another embodiment of the present invention.

Now with reference to FIGS. 6A, 6B, and 6C, description of steps that may be employed for loading the medical device 20 into the sheath 102 will now be provided. For example, the delivery catheter 104 may include a loader 124 sized and configured to facilitate loading the occluder portion 24 of the medical device 20 into the sheath 102 so that the delivery catheter 104 can push the occluder portion 24 through the sheath 102 to a distal portion thereof. With reference to FIG. 6A, the loader 124 may include a tube portion 126 and a handle portion 128. The loader 124 may be slideably positioned over the delivery catheter 104 such that the delivery catheter 104 extends through a bore defined through the loader 124. The loader 124 may be moved over the distal end of the delivery catheter 104 and manually moved or forced over the occluder portion 24 of the medical device 20 so that occluder portion 24 moves to a constricted position enclosed within the tube portion 126. However, prior to moving the loader 124 over the occluder portion 24, the anchor portion should be in a non-deployed position such that an actuator knob and plunger shaft of the handle 106 should be moved to a proximal position, as depicted in FIGS. 8 and 8A. Referring back to FIG. 6A, once the loader 124 is moved completely over the occluder portion 24, the medical device 20 may then be advanced through the sheath 102. The sheath 102, at this point, has already been advanced through the circulatory system to the heart with a distal portion of the sheath 102 positioned in the LAA (not shown), employing typical techniques known in the art.

As depicted in FIGS. 6B and 6C, the loader 124 may be inserted into the sheath 102 and, more particularly, a sheath hub 130. The sheath hub 130 may be coupled at a proximal end of the sheath 102. The components of the sheath hub 130 may include a valve 132 and a sheath fluid port 134. The valve 132 may be a rotating hemostasis valve, such as a Touhy Borst valve or the like, configured to constrict or limit back-flow of blood from the sheath 102 upon rotation of the valve 132. The sheath fluid port 134 may extend from the sheath hub 130 and may be sized and configured to flush or aspirate air from the sheath 102 that may become trapped upon loading the medical device 20 into the sheath 102. In another embodiment, the loader 124 may also include a valve positioned around the delivery catheter 104 to maintain hemostasis while inserted into the sheath hub 130.

As set forth, the loader 124 may be mated or inserted into the sheath hub 130 with a snap or click fit via nubs 136 at the distal end of the tube portion 126 and a rib (not shown) within a bore 138 defined in the sheath hub 130. Once the loader 124 is positioned within the sheath hub 130, the delivery catheter 104 may be advanced through a lumen defined longitudinally in the sheath 102 such that the distal end of the delivery catheter 104 moves to a distal portion of the sheath 102 to expose a distal tip of the occluder portion 24 of the medical device 20 from the distal end of the sheath 102. With this arrangement, the distal tip of the occluder portion 24 may be exposed at the distal end of the sheath 102 and provides, due to the occluder material, a cushioned tip 140, without any exposed metal frame members, facilitating an atraumatic entry into the LAA, thereby, reducing the potential of effusions in the LAA.

Referring to FIGS. 7 through 11, deployment and detachment of the medical device 20 in an LAA 5 (shown in outline) relative to the delivery system 22 will now be described. With respect to FIGS. 7 and 8, upon the physician positioning the distal portion of the sheath 102 in the LAA 5 with the medical device 20 positioned at the distal portion of the sheath 102 with the cushioned tip 140 of the occluder portion 24 exposed at the distal end of the sheath 102, the physician may atraumatically position the distal portion of the sheath 102 to a desired location in the LAA 5. Once the desired location is determined, the physician can deploy the occluder portion 24 of the medical device 20. Such may be employed by simply withdrawing the sheath 102 or manually moving the sheath 102 in a proximal direction. As the sheath 102 is withdrawn, the occluder portion 24 self-expands to an occluder deployed position with the anchor portion 26 maintained in an anchor non-deployed position, as depicted in FIG. 8.

With respect to FIG. 8, a distal portion of the delivery catheter 104 coupled to the medical device 20 is shown. The delivery catheter 104 of this embodiment is coupled to the medical device 20 with an occluder hub nut 142 and collet 116 arrangement. For example, the distal portion of the delivery catheter 104 includes the inner distal tube 114 and an actuator shaft 144. The actuator shaft 144 may include a layered coil, such as a speedometer cable, at a distal end portion thereof, which may be coupled to an inner distal connector 146 moveable within the collet 116. As previously set forth, the collet 116 may include collet fingers 118 extending distally from the collet 116. The inner distal connector 146 may include threads sized and configured to couple to the occluder hub nut 142 and, more particularly, to a threaded screw hole 148 defined in the occluder hub nut 142. The occluder hub nut 142, at a distal end thereof, may include the splined sleeve 72. As previously set forth, the splined sleeve 72 may be sized and configured to couple end portions of each of the anchor actuator arms 68. In another embodiment, the inner distal connector 146 and occluder hub nut 142 may be reversed such that the inner distal connector 146 includes a nut configuration and the occluder hub nut 142 includes a screw configuration. In either case, the medical device 20 may be threadably coupled to the delivery catheter 104.

With reference to FIG. 8A, one embodiment of the handle 106 is depicted. The handle 106 may include a handle housing 150, an anchor actuator release button 152, a plunger shaft 154, and an actuator knob 156. The handle housing 150 may be coupled to a proximal portion of the delivery catheter 104. The plunger shaft 154 and actuator knob 156 is shown in a first position that correlates to the anchor portion 26 being in a non-deployed position (see FIG. 8). The plunger shaft 154 and actuator knob 156 may be moved bi-linearly between a first position and a second position while depressing the anchor actuator release button 152. The functions and various components of the handle 106 will become apparent to one of ordinary skill in the art as discussed in further detail hereafter.

As depicted in FIGS. 8 and 8A, the anchor portion 26 of the medical device 20 is in an anchor non-deployed position. The actuator knob 156 and plunger shaft 154 are moved to the first position, as indicated by arrow 155 that corresponds to the anchor non-deployed position prior to loading the medical device 20 into the loader 124 and then into the sheath 102 (see FIGS. 6A and 6B). In the anchor non-deployed position, the inner distal connector 146 is threadably coupled to the occluder hub nut 142 and is positioned proximal the hub 54 with the anchor portion 26 in a first position or an anchors non-deployed position or, otherwise said, an anchors-in position with a portion of the anchor actuator arms 68 proximal the hub 54 and within a bore 158 defined in the hub 54. Further, in the anchor non-deployed position, the plunger shaft 154 and knob 156 of the handle 106 may be in a proximal or first position as well. With this arrangement, a physician may determine the most favorable position of the medical device 20 within the LAA 5 with the occluder portion 24 in the deployed position prior to deploying the anchor portion 26.

Figure 9:
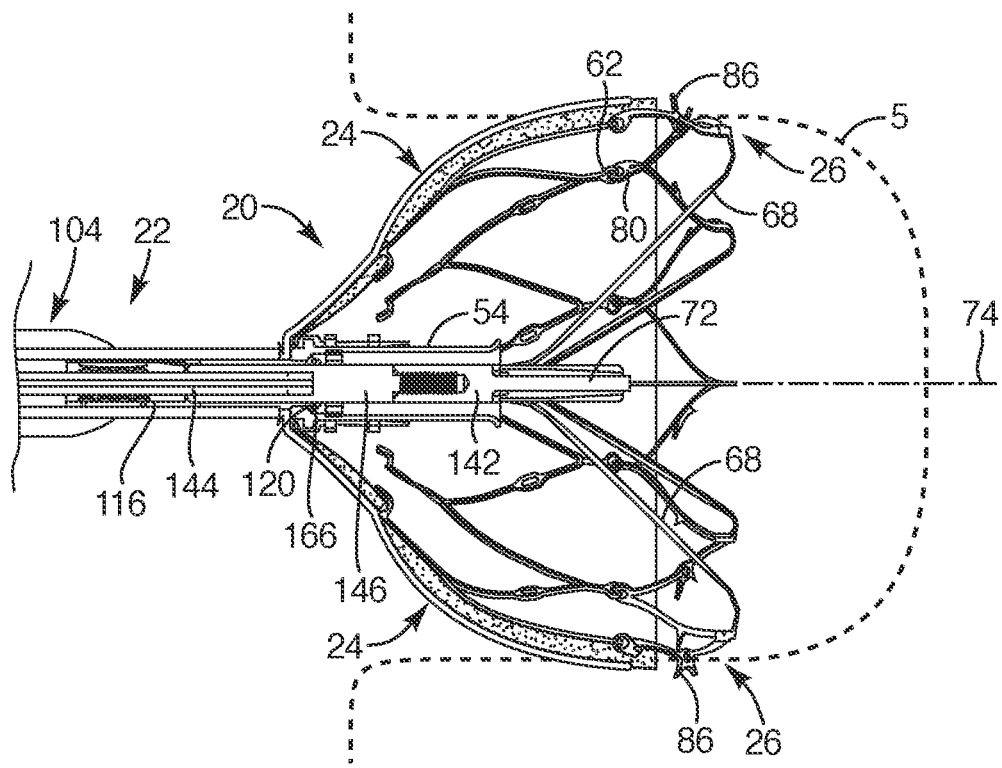
FIG. 9 is a cross-sectional side view of the distal portion of the delivery system and the medical device, depicting both the occluder portion and the anchor portion in an anchor deployed position in the LAA, according to another embodiment of the present invention.
Figure 9A:
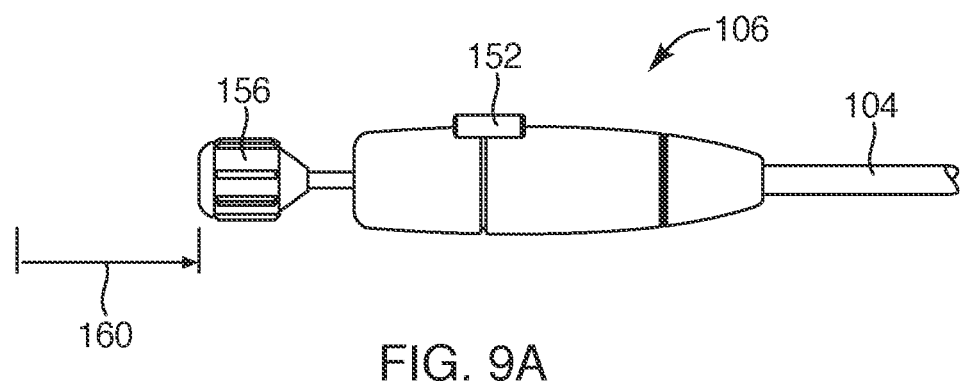
FIG. 9A is a side view of the handle, depicting the handle in a second position corresponding to the anchor deployed position, according to another embodiment of the present invention.

Now turning to FIGS. 9 and 9A, the anchor portion 26 of the medical device 20 may be moved to an anchor deployed position or anchor-out or anchor second position once the physician determines the deployed occluder portion 24 is positioned in the LAA 5 as desired. Such anchor deployed position may be employed by manually moving the actuator knob 156 distally, as indicated by arrow 160, while also depressing the release button 152. In the anchor deployed position, the inner distal connector 146 and occluder hub nut 142 are also moved distally from the collet 116 and into the hub 54 or through the hub 54. Such linear distal movement also moves the anchor actuator arms 68, coupled to the splined sleeve 72, from a distal portion of the delivery catheter 104, through and out of the hub 54 to an everted, deployed position or an expanded position such that the anchor portion 26 unfolds and expands radially by pivoting or rotating at the hinged connection (i.e., at occluder and anchor eyelets 62, 80) between the occluder portion 24 and anchor portion 26. At the anchor deployed position, hooks 86 or tines of the anchor portion 26 are sized and configured to grab tissue and prevent movement so as to effectively anchor the medical device 20 within the LAA 5. Once the anchor portion 26 is deployed, the physician may view the medical device 20 through imaging techniques to ensure proper positioning of the medical device 20 in the LAA 5 while also performing stability tests by pulling proximally on the handle 106 to ensure the medical device 20 is effectively engaging the LAA 5. Such imaging techniques may be enhanced by markers strategically located on the medical device 20 and delivery catheter 104 to provide imaging information to the physician. Such markers may be made from a radiopaque material, such as platinum, gold, tantalum, or alloys thereof, or any other suitable radiopaque materials that are biocompatible.

The hooks 86 of the anchor portion 26 may extend both distally and proximally so as to substantially prevent movement of the medical device 20 in both the proximal and distal directions relative to the LAA 5. In one embodiment, the hooks 86 may include an acute angle 88 (FIG. 3A) relative to the axis 74 of the medical device 20 or the struts of the anchor zig-zag portion 70. The hooks 86 are configured to grab and may dig at the tissue of the LAA 5. Such hooks 86 may be sized, oriented, and configured to prevent puncture or piercing of the hooks 86 all the way through the tissue of the LAA 5, but provide effective and even aggressive engagement with the tissue to provide safe anchoring of the medical device 20 in the LAA 5.

If the physician is dissatisfied with the location or engagement of the medical device in the LAA, the physician may readily disengage the anchor portion 26 from the tissue of the LAA by simply moving the actuator knob 156 in the proximal direction to the first position (FIG. 8A), which simultaneously moves the actuator shaft 144 proximally and, thus, pivots the anchor portion 26 to a disengaged or anchor non-deployed position. The physician may then re-position the occluder portion 24 within the LAA 5 and, once satisfied with the location of the occluder portion 24 in the LAA 5, the physician may readily move the actuator knob 156 forward or a distal direction to pivot and re-engage the anchor portion 26 with the tissue of the LAA 5. The physician may then determine again through imaging and stability tests if the medical device 20 is positioned in the LAA 5 in an effective and safe manner that satisfies the physician. As can be readily understood, the steps of re-positioning the occluder portion 24 and re-engaging the anchor portion 26 of the medical device 20 can be repeated until the physician is satisfied.

Figure 10:
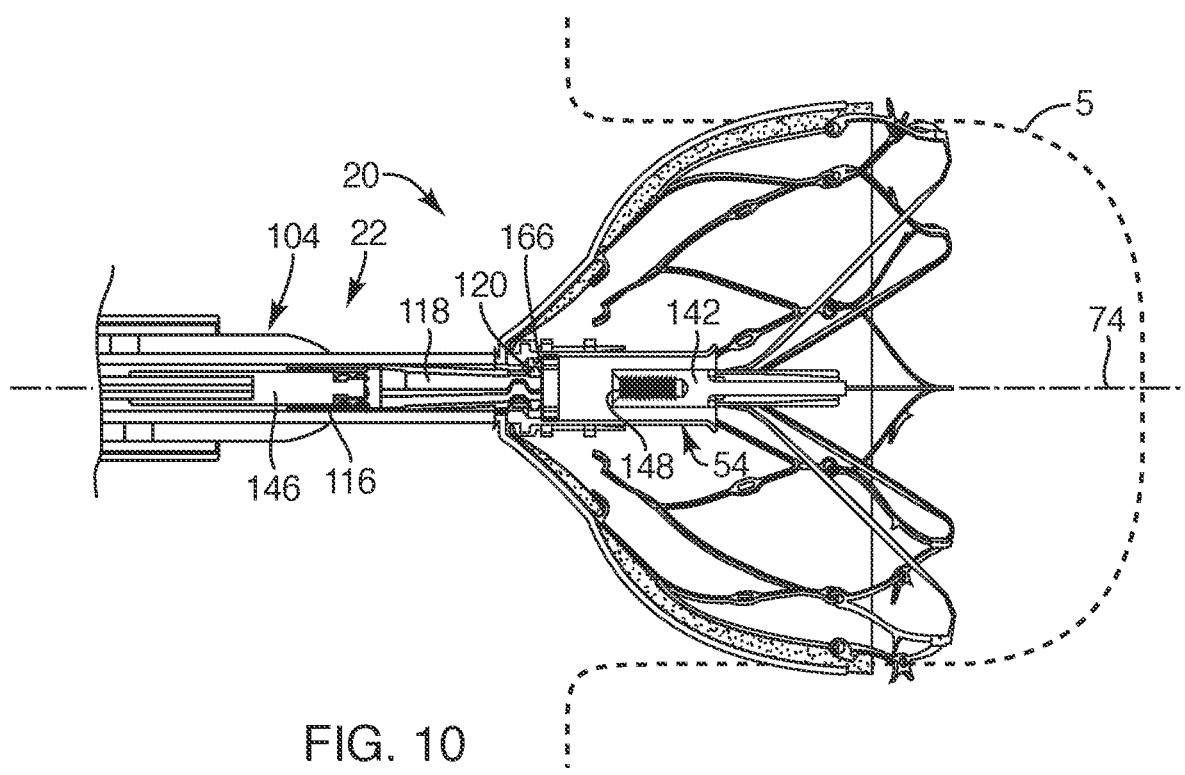
FIG. 10 is a cross-sectional side view of the distal portion of the delivery system and the medical device, depicting the delivery system in the process of being released from the medical device in the LAA, according to another embodiment of the present invention.
Figure 10A:
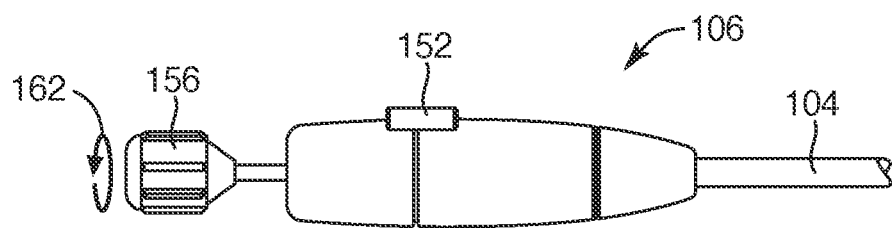
FIG. 10A is a side view of the handle, depicting a portion of the handle being rotated for releasing the medical device, according to an embodiment of the present invention.
Figure 10B:
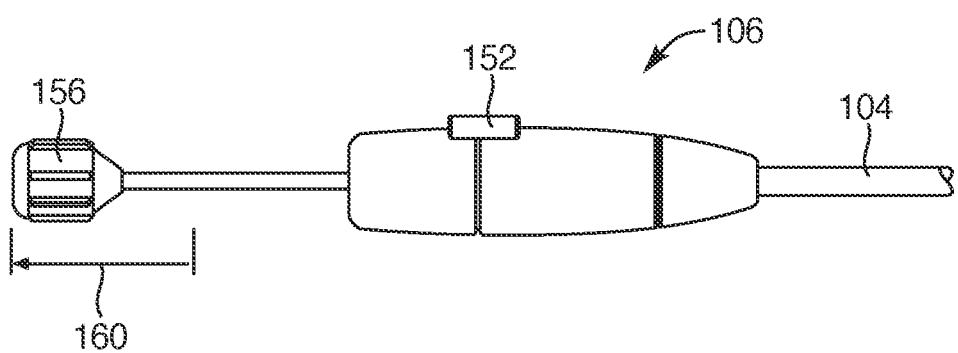
FIG. 10B is a side view of the handle, depicting a portion of the handle actuated from the second position to the first position, according to an embodiment of the present invention.
Figure 11:
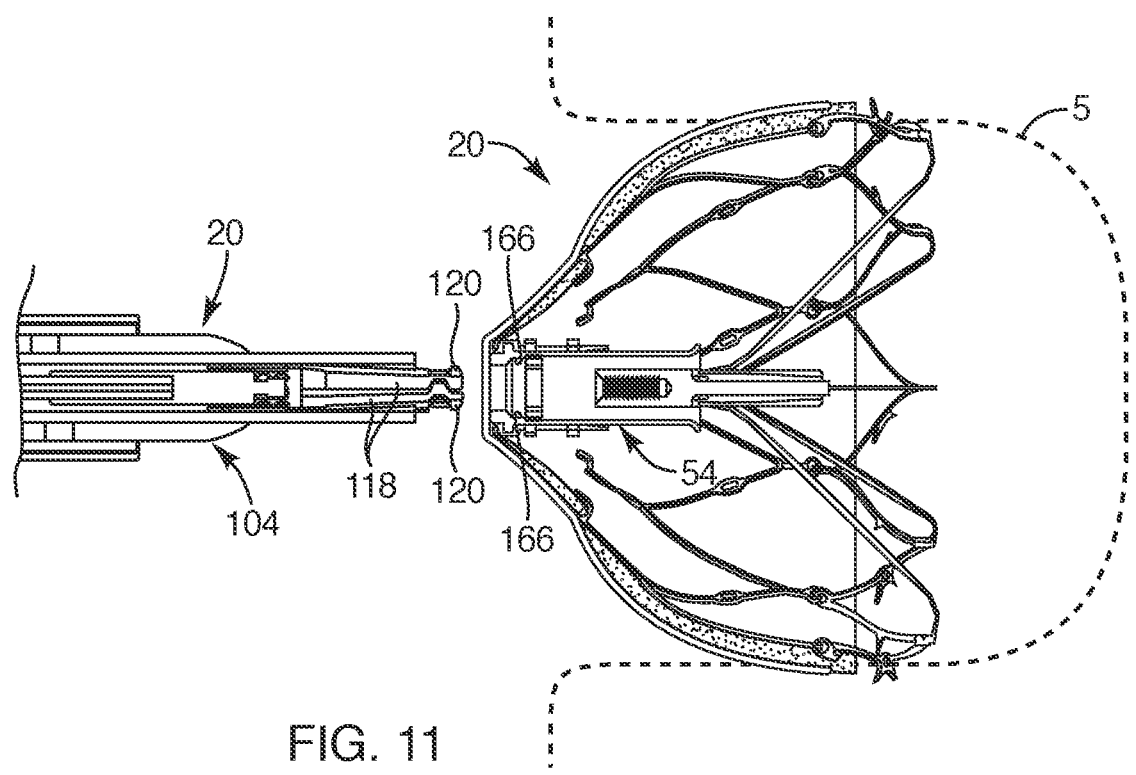
FIG. 11 is a cross-sectional side view of the distal portion of the delivery system and the medical device, depicting the delivery catheter fully released from the medical device, according to another embodiment of the present invention.

Now referring to FIGS. 10, 10A, and 10B, the functions of releasing the medical device 20 will now be described. The medical device 20 may be detached or released by unscrewing the inner distal connector 146 from the screw hole 148 defined in the occluder hub nut 142. Such releasing may be employed by rotating the actuator knob 156 of the handle 106 counter-clockwise several turns, as indicated by arrow 162, until the inner distal connector 146 unwinds from the screw hole 148 of the occluder hub nut 142. The actuator knob 156 may then be pulled proximally back to the first position, as indicated by arrow 164, while depressing the release button 152, which facilitates movement of the inner distal connector 146 in the proximal direction. As the inner distal connector 146 is moved proximally through or into the collet 116, the collet fingers 118 extending distally from the collet 116 collapse inward since the collet fingers 118 may be biased toward an inward position. In other words, prior to the inner distal connector 146 being unwound, the collet fingers 118 may be held in an outer position substantially concentric with the axis 74 of the medical device 20, which maintains the delivery catheter 104 locked to the medical device 20. The collet fingers 118 include outward extending nubs 120 that are held against an abutment 166 within the hub 54 (also shown in FIG. 9). In this manner, once the inner distal connector 146 is unscrewed from the occluder hub nut 142 and moved to a proximal position away from the collet fingers 118, the collet fingers 118 flexibly collapse with a bias to an inward position to move the nubs 120 away from the abutment 166 in the hub 54, thereby, unlocking or unlatching the delivery catheter 104 from the medical device 20. The delivery catheter 104 may then be removed from the medical device 20 with the collet fingers 118 collapsed and the nubs 120 moved proximally from the abutment 166 within the hub 54 as depicted in FIG. 11.

Figure 12:
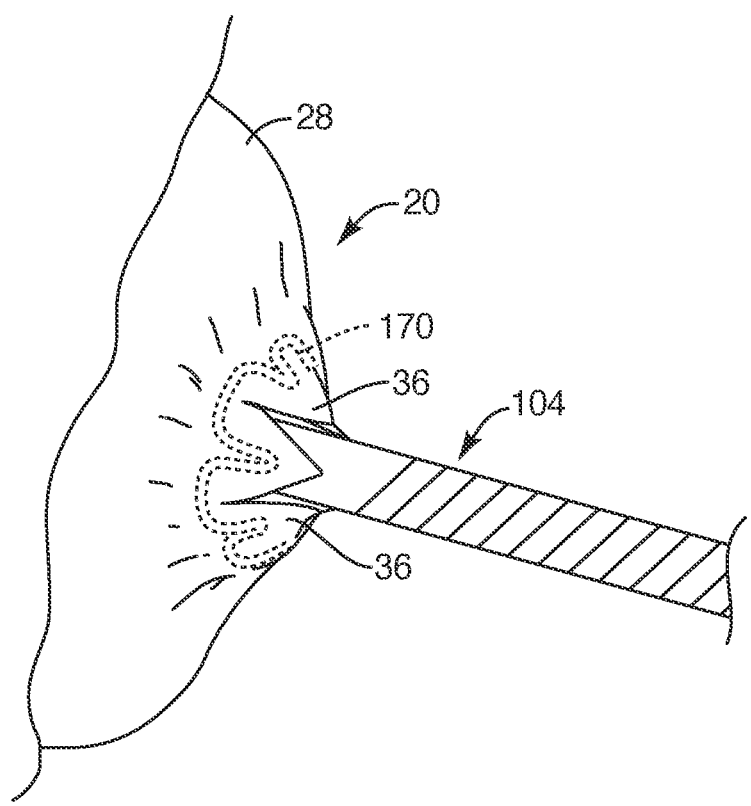
FIG. 12 is a partial perspective view of the proximal side of the medical device coupled to the delivery system, according to another embodiment of the present invention.

With respect to FIGS. 2 and 12, a moveable portion that may include a spring 170 is depicted. In one embodiment, the moveable portion may include a spring 170 with a polymeric covering in the form of polymeric flaps or occluder flaps 36. Such moveable portion having the spring 170 may be sized and configured to close-off the bore 158 of the hub 54 once the delivery catheter 104 is released from the medical device 20. The spring 170 may include a clover configuration or any other suitable configuration to effectively close-off the hub 54. The spring 170 may move between a first biased position (or open first position) and a second relaxed position (or closed second position). The first biased position of the spring 170 (shown in outline form) is depicted in FIG. 12, which is the position of the spring 170 with the delivery catheter 104 coupled to the hub 54. In one embodiment, the position of the delivery catheter 104 attached to the hub 54 holds the spring 170 in the biased or open first position. Once the delivery catheter 104 is removed from the hub 54, the spring 170 may automatically move to the closed, second relaxed position (see FIG. 2) with the occluder flaps 36 (see also FIG. 1) substantially minimizing or eliminating any through hole on the proximal face and adjacent the hub 54. In the second relaxed position of the spring 170, the bore 158 defined in the hub 54 is substantially closed-off with occluder flaps 36, leaving only a cross-like slit (as depicted by adjacently extending occluder flaps 36 in FIG. 1) and substantially eliminating any metal exposed at the hub 54. In this manner, the occluder flaps 36, in the closed second position, advantageously provides a surface at the proximal face of the device without exposed metal at the hub 54 and, further, provides a contiguous surface with the polymeric material of the occluder portion that closes-off the hub 54.

As previously set forth, the spring 170 may be embedded in the occluder material or tissue growth member 28 or attached to an inner occluder material surface such that the spring 170 may include various layers and/or folds of, for example, ePTFE, with one or more slits defining the flaps 36 that facilitates interconnection of the delivery catheter 104 to the hub 54 when the spring 170 is in the first biased position but then may substantially close-off the bore 158 defined in the hub 54 when in the second relaxed position. Such arrangement is advantageous to substantially prevent blood flow through the hub 54 or to substantially prevent the potential of migrating emboli or thrombus from the hub 54 itself once the medical device 20 is positioned in the LAA. In this manner, the spring 170 facilitates closing-off the through hole of the hub 54 and/or covers any exposed metal at the hub so that emboli or thrombus that may collect on the metal is prevented from escaping from the hub. In other words, the flaps 36 provide a substantially impassible barrier relative to otherwise potential migrating emboli or thrombus at the hub 54.

Figure 13A:
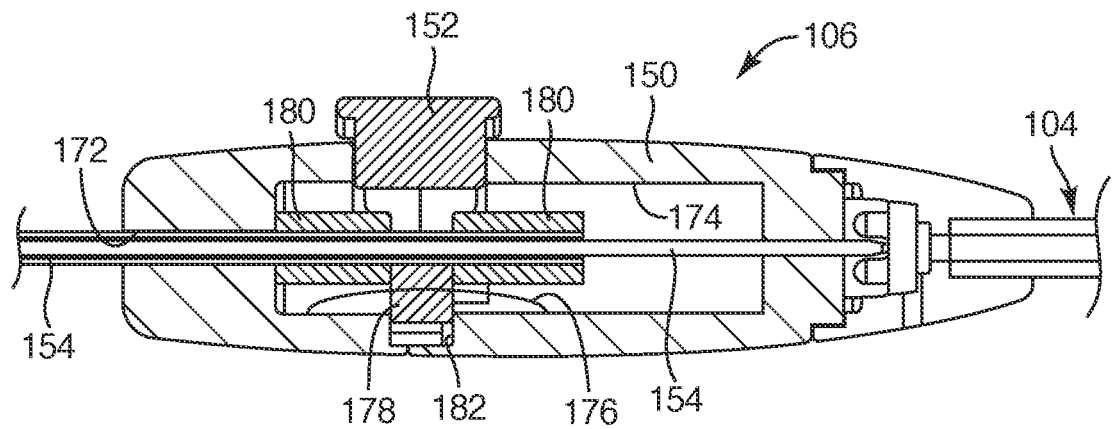
FIGS. 13A and 13B are cross-sectional side views of the handle, depicting a release button in a first and second position, respectively, to facilitate actuation of a plunger shaft, according to another embodiment of the present invention.
Figure 13B:
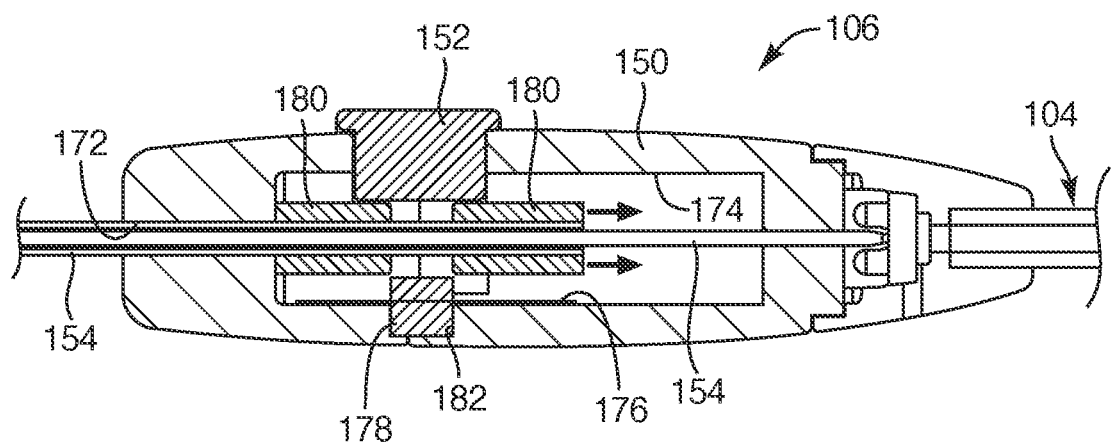

Now referring to FIGS. 13A and 13B, actuation of the release button 152 of the handle 106 is depicted. The handle housing 150 defines a hole 172 that may extend along a longitudinal axis of the handle housing 150 and may be sized to hold the plunger shaft 154 to move bi-linearly therethrough. The handle housing 150 may also define a hollow portion 174 therein. The plunger shaft 154 may extend through the handle housing 150 and be coupled to components coupled to actuator shaft 144 and the inner distal connector 146 at the distal portion of the delivery catheter 104 (see FIG. 9). The handle 106 also may include a leaf spring 176 configured to bias against the release button 152. The release button 152 may include a button post 178. The leaf spring 176 may be coupled to the button post 178 to bias the release button 152 to a non-depressed position or first position. The plunger shaft 154 may also include two travel stops 180 fixed thereto. By depressing the release button 152 to a depressed position or second position, the button post 178 depresses the leaf spring 176 and moves within a cavity 182. Once the button post 178 is moved within the cavity 182, the travel stops 180 coupled to the plunger shaft 154 may then freely move distally (and then back proximally) past the button post 178 a predetermined distance gauged by the travel stops 180 within the hollow portion 174 defined by the handle housing 150. In this manner, the plunger shaft 154 may move the predetermined distance which directly corresponds with the distance or length moved by the actuator shaft 144 and actuation of the anchor portion of the medical device 20 between the anchor non-deployed position and anchor deployed position (see FIGS. 8 and 9).

Referring back to FIG. 8, in another embodiment, the sheath 102 may include an imaging device 190. The imaging device 190 may be sized and configured to be positioned at a distal end of the sheath 102 and may include one or more lines 192 extending from the imaging device 190 and proximally toward the sheath hub 130 (FIG. 5C) for transferring imaging information from the imaging device 190 to a computer and a display (not shown), as known to one of ordinary skill in the art, and viewable by the physician in real-time. The sheath 102, upon being withdrawn from the occluder portion 24, being positioned substantially concentric or proximal of the medical device 20, may be at a vantage point and location in the left atrium adjacent the LAA to provide detailed imaging information otherwise not readily available to the physician. The imaging device 190 may be an ultrasound imaging device or any other suitable imaging device known in the art. In another embodiment, an imaging device 190a may be positioned proximal a distal end of the delivery catheter 104 in a similar manner to that described above. In still another embodiment, the distal end of the delivery catheter 104 and/or sheath 102 may include one or more sensor devices 191. The sensor devices 191 may be configured to sense pressure, flow, and any other cardiac dynamics that may be useful to the physician. In this manner, the sensor devices 191 and/or imaging device 190, 190a may provide additional information to assist the physician to accurately position the medical device 20 in the LAA 5.

Figure 14A:
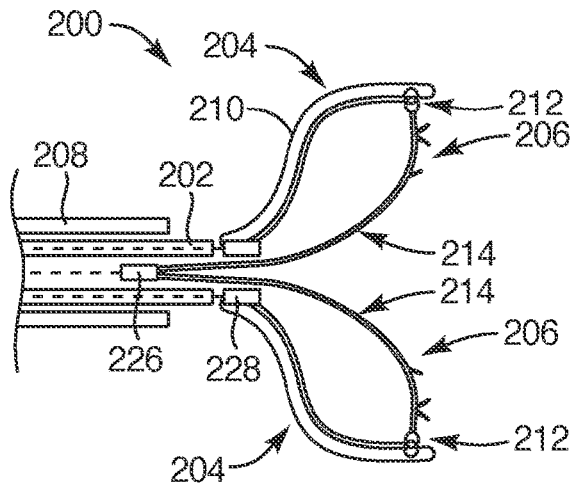
FIGS. 14A and 14B are simplistic side profile views of another embodiment of a medical device, depicting the medical device in an anchor non-deployed position and an anchor deployed position, respectively, according to the present invention.
Figure 14B:
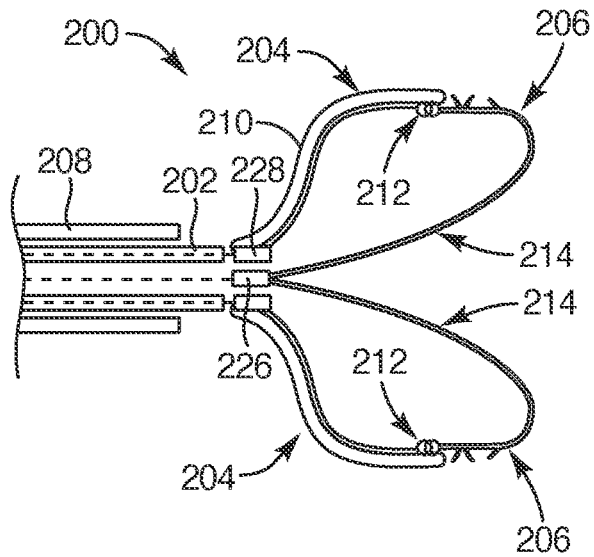

Now with reference to FIGS. 14A and 14B, another embodiment of a medical device 200 coupled to a distal portion of a delivery catheter 202, the medical device 200 (depicted in a simplistic profile view) in a partially deployed position and fully deployed position, respectively, is provided. As in previous embodiments, the medical device 200 may include an occluder portion 204 and an anchor portion 206 that may be separately deployed. For example, once a sheath 208 is positioned in the LAA (not shown) with the medical device 200 at a distal end portion thereof, the sheath 208 is withdrawn to deploy an occluder portion 204 of the medical device 200 or to partially deploy the medical device 200. Once the occluder portion 204 is deployed, then the anchor portion 206 may be deployed, to fully deploy the medical device 200.

In this embodiment, the occluder portion 204 is substantially similar to the previous embodiment, except the tissue growth member 210 is attached to an outer surface of the frame components of the occluder portion 204. The tissue growth member 210 of this embodiment may include similar layering of one or more materials as set forth for the tissue growth member described in detail relative to FIG. 1B. Further, although the anchor portion 206 may be hingably coupled to the occluder portion 204 with a hinge arrangement 212 and, in many respects functions similar to the previous embodiment, the anchor portion 206 of this embodiment includes multiple separate and distinct anchor frame segments 214, best shown in FIG. 15.

Figure 15:
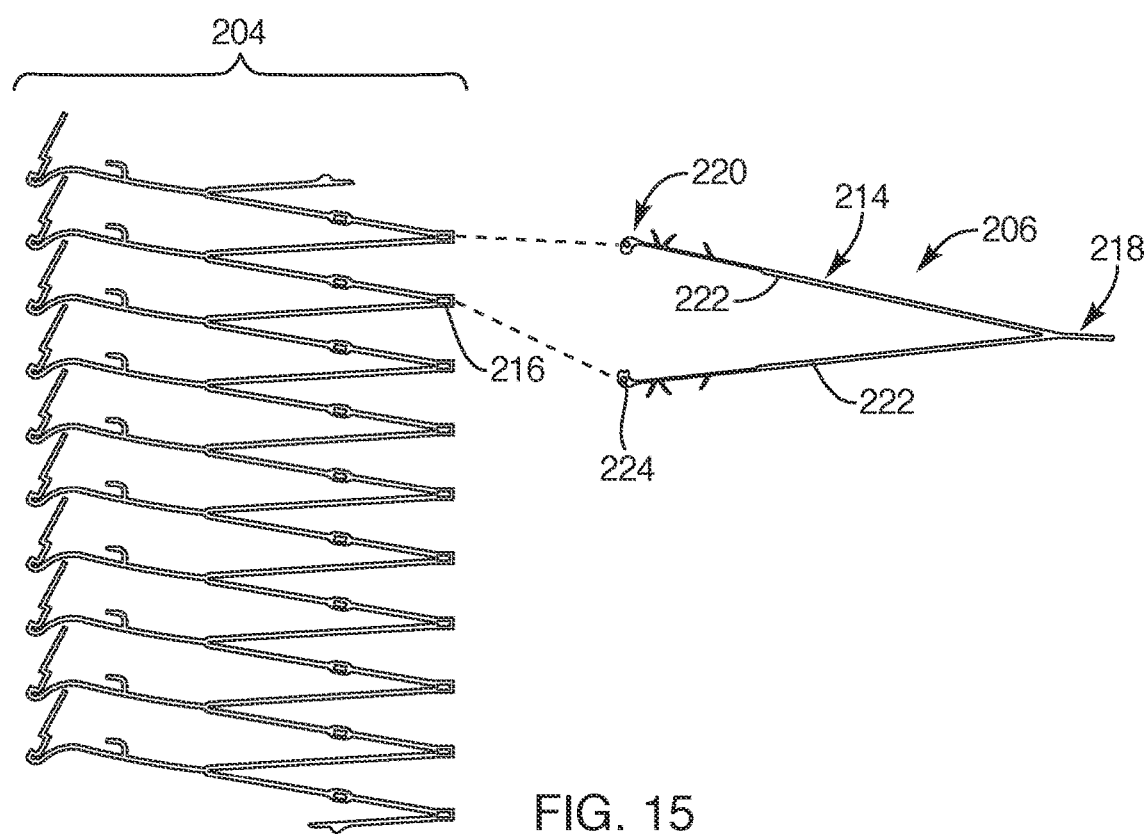
FIG. 15 is a top view of the occluder portion and the anchor portion of the medical device of FIGS. 14A and 14B, depicting fame components cut from a flat sheet, according to another embodiment of the present invention.

With reference to FIG. 15, the frame components of the occluder portion 204 and the anchor portion 206 are depicted in, for example, a preformed state subsequent to being laser cut from a flat sheet of super elastic material, such as Nitinol. For simplicity purposes, there is only one anchor frame segment 214 shown, but in this embodiment, there may be five anchor frame segments 214 to correspond and couple to, for example, occluder frame apertures 216 of the occluder portion 204. As shown, the frame components of the occluder portion 204 may be substantially similar to the frame components of the occluder portion 204 described in the previous embodiment relative to FIG. 3.

With respect to the anchor frame segments 214, each anchor frame segment 214 may extend between a first end 218 and second end 220 with two actuator arms 222 extending therebetween such that each anchor frame segment 214 may exhibit a "Y" or "V" configuration in the pre-formed state. Each actuator arm 222 may include an anchor hinge aperture 224 at the second end 220 and, at the first end 218, the actuator arm 222 may be coupled to a collar arrangement 226 or splined sleeve, similar to that of the previous embodiment. With this arrangement, the actuator arms 222, as depicted in FIGS. 14A and 14B, may pivot about the occluder portion 204 at the hinge arrangement 212. Further, the actuator arms 222 may form a loop configuration or loop extension in the anchor deployed position with the first end 218 of the actuator arms 222 moveable or actuatable through the hub 228 of the medical device 200.

Figure 7:
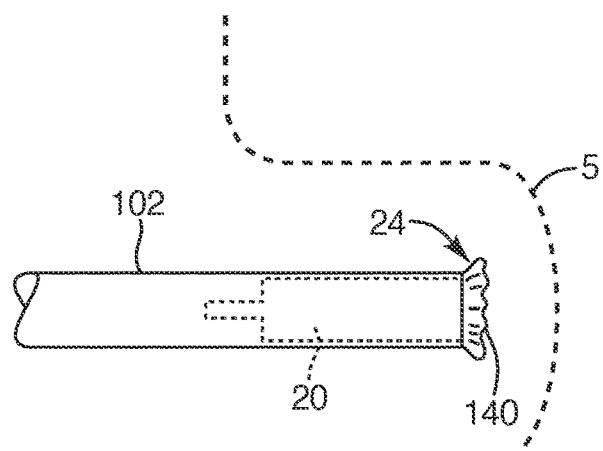
FIG. 7 is a side view of a distal portion of the sheath, depicting a portion of the medical device exposed at a distal end of the sheath in the LAA, according to another embodiment of the present invention.

Now with reference to FIGS. 16A, 16B, and 17, another embodiment of a medical device 250 depicted in a partially deployed position (FIG. 16A) and a fully deployed position (FIG. 16B), similar to previous embodiments, is depicted. In this embodiment, the occluder portion 252 can be similar to the previous embodiments, but the anchor portion 254 may include an anchor zig-zag portion 256 and loop extensions 258 or actuator arms as separate anchor frame components. In this embodiment, the medical device 250 may include a dual hinge arrangement. For example, the occluder portion 252 may be hingably coupled to an anchor zig-zag portion 256 with a first hinge arrangement 260 and the anchor zig-zag portion 256 may be hingably coupled to the loop extensions 258 with a second hinge arrangement 262. The profile and functionality of the medical device 250 may be similar to the previous embodiments, except the loop extensions 258 may take a more direct inward angle from the anchor zig-zag portion 256 due to the second hinge arrangement 262 therebetween. Similar to the embodiment of FIG. 15, this embodiment may include ten loop extensions 258 or actuator arms, though for simplicity purposes only two loop extensions 258 (as a single loop extension segment) are shown in FIG. 17. It should be noted that the embodiments of FIGS. 14 and 16 also provide the feature to facilitate a cushion tip (not shown) as depicted in FIG. 7 when constricted in the sheath 264. Further, it should be noted the embodiments depicted and described relative to FIGS. 1, 14 and 16 include similar features and structure and, therefore, the descriptions provided in one embodiment may also be applicable to the other described embodiments.

Figure 19:
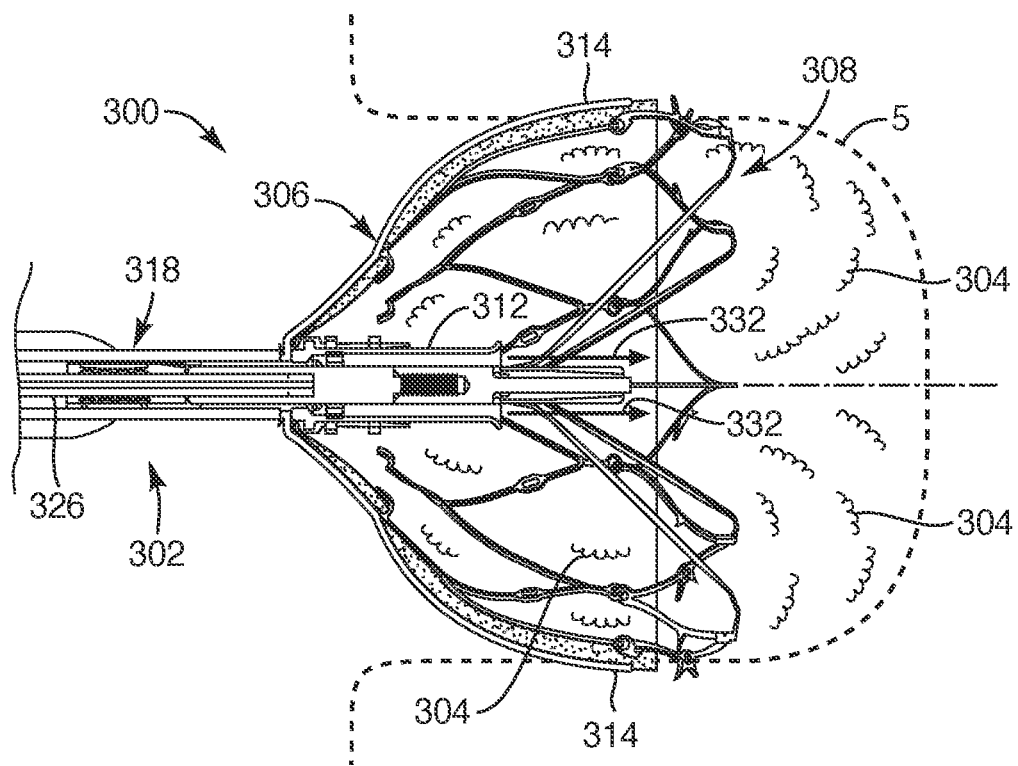
FIG. 19 is a cross-sectional view of the medical device and the distal portion of the delivery system, depicting a contrast fluid flowing from a hub of the medical device and into the left atrial appendage, according to another embodiment of the present invention.
Figure 20:
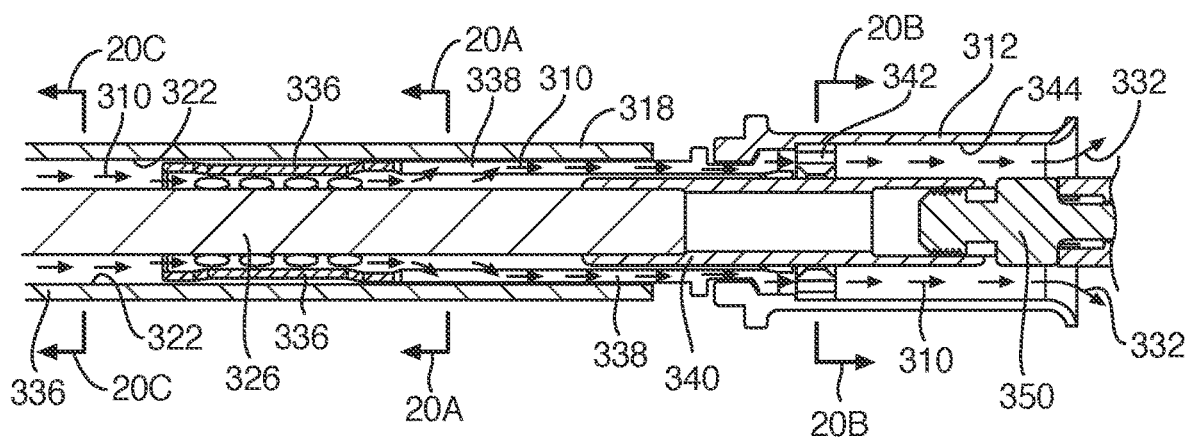
FIG. 20 is an enlarged cross-sectional view of the distal portion of the delivery system and the hub of the medical device (with the occluder portion removed for simplification purposes), depicting a flow path of the contrast fluid moving through the delivery system and hub of the medical device, according to another embodiment of the present invention.

Now with reference to FIGS. 18 through 20, another embodiment of a medical device 300 and a medical device delivery system 302 for modifying an LAA 5 of the heart that facilitates imaging of the LAA 5 with contrast fluid 304 and an imaging device (not shown) is provided. In this embodiment, the structural components and functionality of the medical device 300 and the medical device delivery system 302 may be substantially similar to any one of the embodiments previously described. For example, the medical device 300 may include an occluder portion 306 and an anchor portion 308, similar to that described above.

In this embodiment, upon the medical device 300 being positioned within the LAA 5 with the anchor portion 308 deployed and engaged with tissue of the LAA 5, the medical device delivery system 302 and the medical device 300 may include a common flow path 310 defined therethrough for injecting a contrast fluid 304 through a hub 312 of the medical device 300 and to a distal side of the medical device 300 and into the LAA 5. One important aspect of this embodiment may be that the occluder portion 306 of the medical device includes a substantially non-permeable material of, for example, a polymeric material, such as foam and/or ePTFE, described in earlier embodiments herein as the tissue growth member. In one embodiment, the ePTFE may be the material that is non-permeable. In this manner, a physician can determine whether the contrast fluid 304 is being substantially maintained within the LAA 5 on the distal side of the medical device 300 to assess whether the medical device 300 is properly positioned within the LAA 5. Also, the physician can determine whether there are gaps between an outer periphery 314 of the medical device 300 and the tissue of the LAA 5 by viewing the contrast fluid 304 dissipating from the distal side of the medical device 300, as discussed in further detail below.

In one embodiment, the occluder portion 306 of the medical device 300 may include a polymeric material, such as the before-described foam and/or ePTFE. In another embodiment, the polymeric material may include a bio-agent coated over or impregnated within the polymeric material. Such bio-agent may be configured to enhance tissue growth and endothelization over the proximal side of the occluder portion 306 of the medical device 300. In another embodiment, the polymeric material may include a coating thereon that may be an anti-thrombotic coating, such as Heprin. In still another embodiment, the occluder portion may include a biological tissue, in addition to or instead of the before-described polymeric material. Such biological tissue may be a biological sourced tissue, such as pericardial tissue and/or peritoneum tissue, or any suitable biological tissue that is biocompatible as known in the art. Further, the biological tissue may be non-permeable, strong, and thin so as to readily be moved with the occluder portion frame structure between collapsed and expanded configurations. Further, the non-permeable characteristics of the pericardial tissue may function to substantially maintain contrast fluid 304 in the LAA 5 upon the medical device being positioned in the LAA. In another embodiment, the biological tissue may be permeable or include portions with permeable characteristics and other portions with non-permeable characteristics.

With reference to FIGS. 18, 18A and 18B, the medical device delivery system 302 includes a sheath 316, a delivery catheter 318 coupled to a handle 320, and the medical device 300 coupled to a distal end of the delivery catheter 318, similar to that described and depicted relative to FIG. 4 herein (as well as other embodiments herein). The delivery catheter 318 extends between a proximal end and a distal end such that the proximal end is coupled to the handle 320 and the distal end of the delivery catheter 318 is coupled to the implantable medical device 300. Further, the delivery catheter 318 defines a lumen 322 extending along a longitudinal length of the delivery catheter 318. The handle 320 may include a fluid port 324 sized and configured to directly communicate with the lumen 322 of the delivery catheter 318. Also, the delivery catheter 318 may include an actuator shaft 326 (coupled to the handle 320 and actuatable by the actuator knob 321) extending therethrough for controlling actuation of the anchor portion 308 of the medical device 300. With this arrangement, fluid, such as contrast fluid 304, may be injected through the fluid port 324 of the handle 320 and directly through the lumen 322 of the delivery catheter 318 such that the contrast fluid 304 may advance toward the medical device 300. The contrast fluid 304 may be a radio opaque fluid or dye (or any other suitable contrast fluid) that is viewable through imaging techniques, such as fluoroscopy or any other suitable imaging technique, as known to one of ordinary skill in the art.

As in previous embodiments, the delivery catheter 318 and the medical device 300 coupled at the distal end thereof may be sized and configured to be pushed through a sheath lumen 317 defined along a length of the sheath 316. The sheath 316 may also include a sheath fluid port 328 sized and configured to inject fluid, such as contrast fluid 304, through the sheath lumen 317 and to exit from the distal end of the sheath 316. Such injection of contrast fluid 304 through the sheath lumen 317 via the sheath fluid port 328 may provide additional information to the physician relative to imaging a proximal side of the medical device 300 upon being positioned in the LAA, discussed further herein.

The fluid, such as contrast fluid 304, may be injected through the fluid port 324 of the handle 320, as well as the sheath fluid port 328 of the sheath 316, with an injection device 330. In one embodiment, the injection device 330 may be a syringe for manual injection through the fluid port 324 of the handle 320 or through the sheath fluid port 328 of the sheath 316. In another embodiment, the injection device 330 may include an injection machine that controls the pressure, amount, and/or flow rate of fluid being injected through the fluid port 324 of the handle 320 (or through the sheath fluid port 328 of the sheath 316), as known to one of ordinary skill in the art.

Now with reference to FIGS. 19 and 20, fluid, such as contrast fluid 304, may flow through the lumen 322 of the delivery catheter 318, as discussed above, and through the hub 312 (and components associated therewith) of the medical device 300, the medial device 300 being positioned in the LAA 5. As the contrast fluid 304 exits the hub 312 of the medical device 300, as depicted by arrows 332 in FIG. 19, the contrast fluid 304 mixes with the blood in the LAA 5 and is viewable via real-time imaging techniques, such as with a fluoroscopy or the like. Due to the occluder portion 306 having the substantially non-permeable material associated therewith, if the medical device 300 is properly positioned in the LAA 5, the contrast fluid 304 may be substantially maintained within the LAA 5, but for general seeping around the outer periphery 314 of the medical device 300 without an identifiable source or gap. In this manner, the physician can readily identify if the medical device is properly positioned within the LAA by viewing the contrast fluid 304 substantially maintained on a distal side of the medical device. The meaning of substantially maintaining contrast fluid 304 in the LAA means substantially containing, sustaining and/or retaining the contrast fluid in the LAA, except for general seeping along the outer periphery 314.

If there is a gap between the outer periphery 314 of the medical device 300 and the tissue of the LAA 5, the physician will readily ascertain and identify such gap due to the contrast fluid 304 moving through a localized portion from the LAA 5 such that contrast fluid is viewable in a concentrated flow or jet escaping the LAA 5 and moving proximally past the outer periphery 314 of the medical device 300. If the physician determines there is a gap, the physician can readily retract the anchor portion 308 and re-position the medical device 300 in the LAA 5 and then deploy the anchor portion 308 to engage the tissue in the LAA 5, as discussed in detail herein. The physician may then inject additional contrast fluid 304 through the hub 312 of the medical device 300 to determine if the medical device 300 is properly positioned. In addition, the physician may also inject contrast fluid 304 through the sheath 316 via the sheath fluid port 328, as previously discussed, to view a proximal side of the medical device 300 in the LAA 5, thereby, obtaining additional information relative to the position of the medical device 300 in the LAA 5. Once the physician is satisfied with the position of the medical device 300, the delivery catheter 318 may be de-coupled or detached from the medical device 300, as previously set forth herein.

Figure 20A:
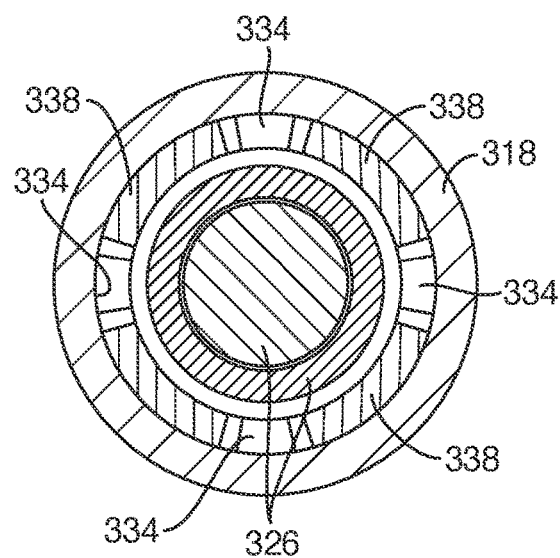
FIG. 20A is an enlarged cross-sectional view taken from region 20A of FIG. 20, depicting the flow path for the contrast fluid at a distal portion of the delivery system, according to another embodiment of the present invention.
Figure 20B:
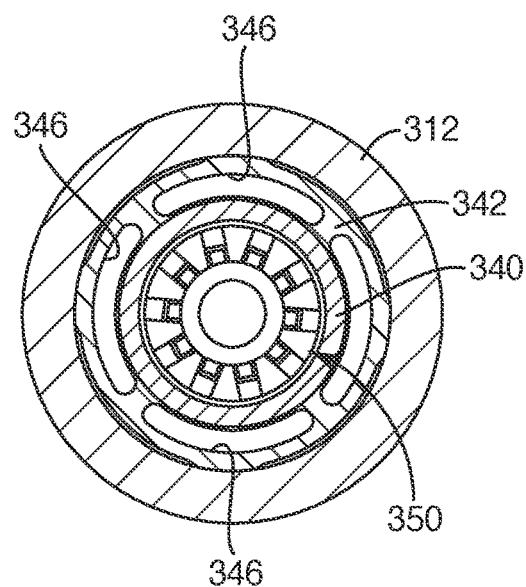
FIG. 20B is an enlarged cross-sectional view taken from region 20B of FIG. 20, depicting the flow path for the contrast fluid at the hub of the medical device, according to another embodiment of the present invention.

With respect to FIGS. 20, 20A, and 20B, the flow path (depicted by arrows 310 in FIG. 20) of the contrast fluid 304 flowing from the delivery catheter 318 and through the hub 312 will now be described. The flow path 310 extends through the lumen 322 of the delivery catheter 318 and surrounds and moves along a length of the actuator shaft 326 and the delivery catheter 318. Section 20C identified in FIG. 20 may be substantially similar to that described and depicted in FIG. 18A, depicting the delivery catheter 318 defining the lumen 322 with the actuator shaft 326 positioned therethrough. The flow path 310 continues to advance along the collet 336 and then outward into a space 334 or channel defined between the collet fingers 338 (see FIGS. 20 and 20A). The flow path 310 continues advancing between an inner distal connector 340 and the delivery catheter 318 and then between the inner distal connector 340 and the medical device 300 (only the hub 312 is shown), as depicted in FIGS. 20 and 20A. The hub 312 includes a guide ring 342 that may be embedded within the inner diameter or bore 344 defined in the hub 312 itself. Such guide ring 342 includes apertures 346 (see FIG. 20B) defined therein through which the flow path 310 extends. Such apertures 346 may include an annular space or partial annular configuration or space. In another embodiment, the inner diameter or bore may include an annular protrusion, instead of the guide ring 342, such that the bore 344 between the annular protrusion and the inner distal connector 340 may define an annular space through which the flow path 310 extends (instead of the apertures 346). Once the flow path 310 continues through the apertures 346 or annular space and past the guide ring 342 or annular protrusion in the bore 344, the flow path 310 continues advancing through the bore 344 of the hub 312 and distally over the inner distal connector 340. The inner distal connector 340 may include threads along an inner diameter thereof to couple to threads on a proximal end of the anchor hub 350. The flow path 310 continues advancing through the hub 312 until exiting the hub 312, as depicted with arrows 332, so that contrast fluid 304 can enter the LAA 5 on the distal side of the medical device 300, as shown in FIG. 19. With this arrangement, each of the handle 320, delivery catheter 318 and hub 312 of the medical device 300 includes a common, shared, or corresponding flow path 310 that facilitates contrast fluid 304 to exit a distal side of the medical device 300. As such, a physician may view the medical device 300 positioned in the LAA 5 to determine if the contrast fluid 304 is being substantially maintained within the LAA (since the occluder portion includes a non-permeable material), but for minor general seeping along the outer periphery 314 of the medical device 300 contacting the LAA 5. In this manner, the physician can obtain additional imaging information to ascertain whether the medical device 300 is properly positioned in the LAA 5.

Figure 21:
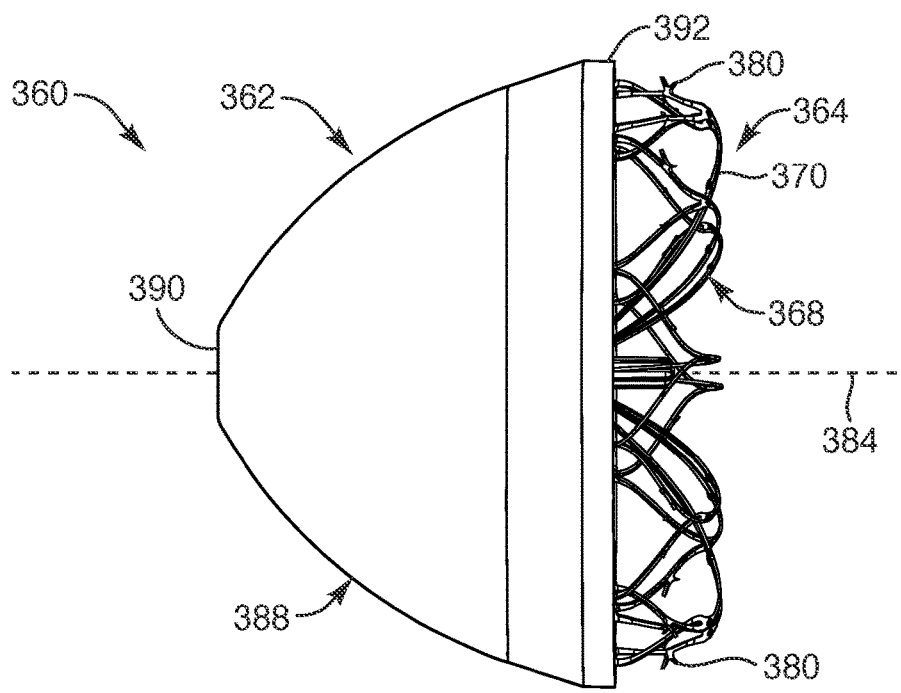
FIG. 21 is a side view of another embodiment of a medical device, according to the present invention.
Figure 22:
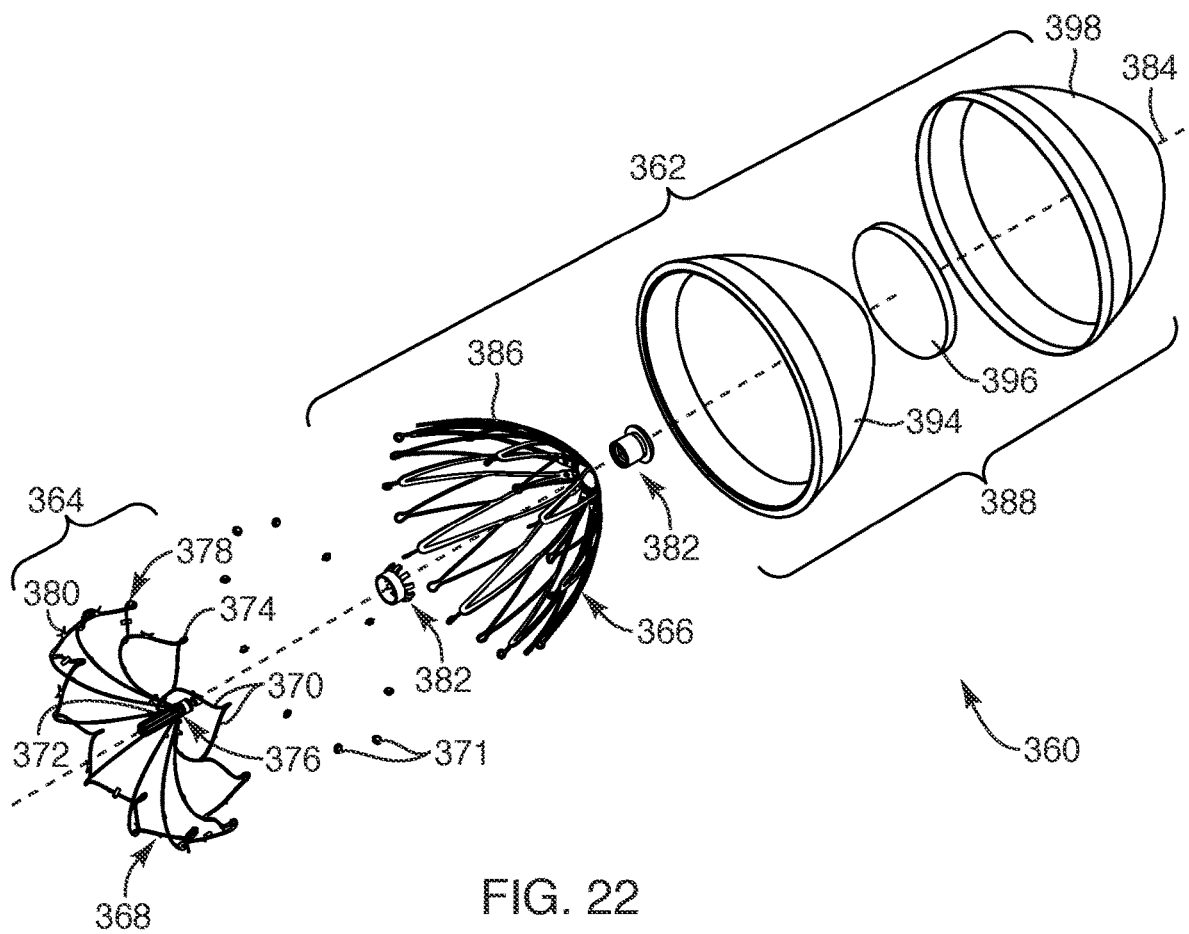
FIG. 22 is an exploded view of the medical device of FIG. 21, according to another embodiment of the present invention.

Now with reference to FIGS. 21 and 22, another embodiment of a medical device 360 for positioning and securing within the ostium of a left atrial appendage, is provided. The medical device 360 of this embodiment may be employed with the previously described delivery systems herein, for example, the medical device delivery system 302 with its sheath 316, delivery catheter 318 and handle 320, described and depicted in FIG. 18. Similar to previous embodiments, the medical device 360 may include an occluder portion 362 and an anchor portion 364, the occluder portion 362 and anchor portion 364 including a frame structure or framework. Such frame structure may define an occluder frame 366 and an anchor frame 368 pivotably coupled to each other. In this embodiment, the occluder portion 362 with its frame structure may include different and additional structural features than previous embodiments. For example, the occluder portion 362 may include additional conformability with the anatomy as well as the occluder portion 362 may hold structural characteristics that enhance its case for constricting within the sheath.

As set forth, the medical device 360 may include the anchor portion 364. Similar to previous embodiments, the anchor portion 364 may include multiple anchor frame segments 370 extending between a first end 372 and a second end 374. The first end 372 may be coupled to an anchor hub 376 or secondary hub. The second end 374 may include an anchor aperture 378 for pivotably coupling to the occluder portion 362. Such pivotable coupling or connection may be a hingable coupling that may be formed with interlocking pieces 371, similar to the interlocking pieces 94 described relative to FIG. 3B.

In addition, the anchor frame segments 370 may include tines 380 at a distal position of the second end 374 of the anchor portion 364. Further, the anchor frame segments 370 may extend distally from the second end 374 and then extend radially inward, and then extend proximally toward the first end 372 and the anchor hub 376 so that a distal most portion of the anchor portion 364 exhibits a loop type configuration or an arcuate component/configuration, similar to previous embodiments. Such distal most portion of the medical device 360 having the arcuate component or configuration so that the distal most portion of the medical device may be atraumatic to tissue within the left atrial appendage.

The occluder portion 362 may include a hub 382 or primary hub defining an axis 384 and may include occluder frame segments 386 and a tissue growth member 388. The occluder frame segments 386 may extend from a proximal end 390 to a distal end 392, the proximal end 390 coupled to the hub 382 and the distal end 392 configured to be coupled to the second end 374 of the anchor portion 368. In one embodiment, the proximal end 390 may be pivotably coupled to the hub 382, discussed in further detail herein. The occluder frame segments 386 may extend in a cup-like configuration defining an outer side surface or convex configuration and an inner side surface exhibiting a concave configuration. The outer side surface of the occluder frame segments 386 may be attached to the tissue growth member 388 also having the cup-like configuration.

The tissue growth member 388 may include one or more layers of tissue growth material layers. For example, the one or more layers may include one or more foam layers and/or one or more ePTFE layers. In one embodiment, the tissue growth member 388 may include a first layer 394, a second layer 396, and a third layer 398. The first layer 394 may be a foam material, such as polyurethane foam or any other suitable polymeric material. The first layer 394 may be attached to the outer side surface of the occluder frame segments 386 by stitching or sewing the first layer 394 to the occluder frame segments 386. In another embodiment, the first layer 394 may be adhesively attached and/or hooked to the occluder frame segments 386. The second layer 396 may be smaller in size than the first layer 394 and may be disc shaped. The second layer 396 may be a foam material, similar to the first layer 394, and may be adhesively attached to a proximal side and outer surface of the first layer 394. The third layer 398 may be an ePTFE layer or other suitable polymeric material that induces tissue growth. The third layer 398 may include multiple ePTFE layers. The third layer 398 of the tissue growth member 388 may be adhesively attached to the outer surface of the first and second layers 394, 396 or may be attached employing any other suitable affixing procedure. Further, the third layer 398 may be larger than both the first and second layers 394, 396 such that the third layer 398 may extend more distal than the first layer 394. In one embodiment, the third layer 398 may extend distal the first layer 394 and distal the occluder frame segments 386.

Figure 23:
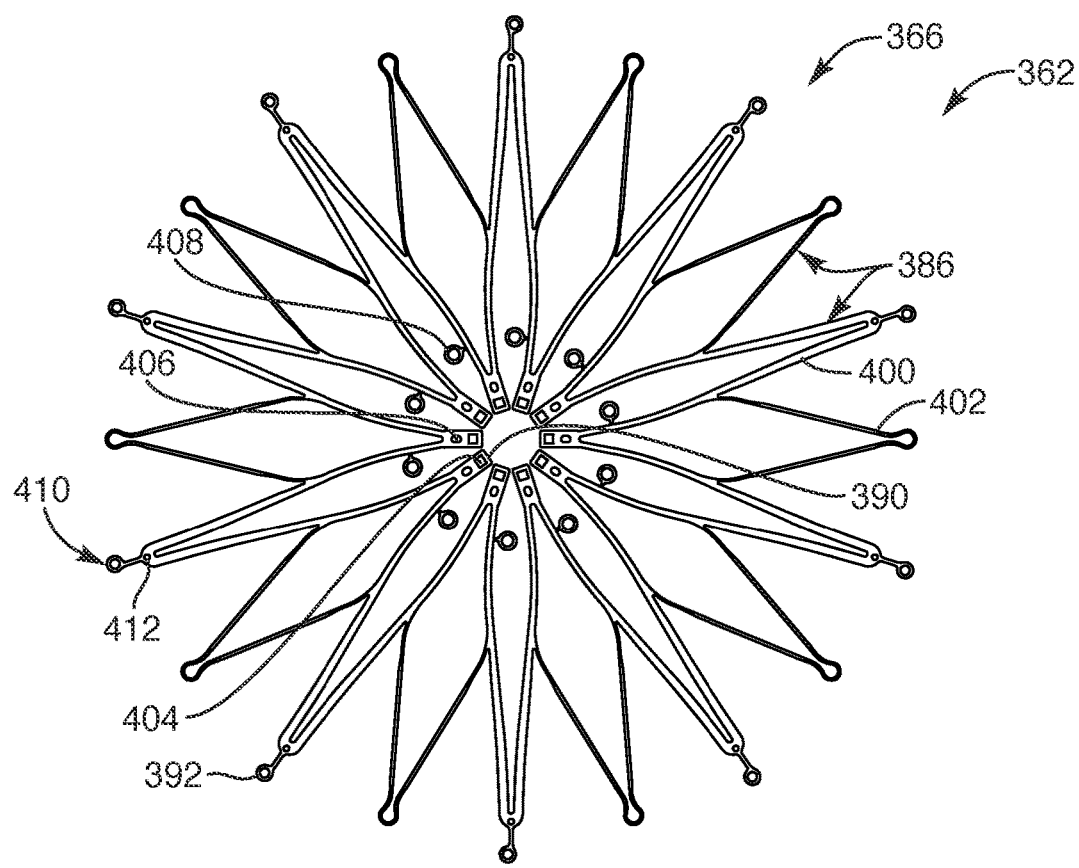
FIG. 23 is a top view of an occluder frame of an occluder portion, depicting the occluder frame as cut from a flat sheet of material, according to another embodiment of the present invention.

With reference to FIG. 23, the occluder frame 366 having occluder frame segments 386 are shown as cut from a flat sheet of material. In this depicted as-cut state, the occluder frame segments 386 may be a monolithic seamless structure exhibiting a star-like configuration with the occluder frame segments 386 extending from a central portion to an outer periphery of the star-like configuration. The proximal end 390 of each of the occluder frame segments 386 may be at the central portion and the distal end 392 of each of the occluder frame segments 386 may be at the outer periphery of the star-like configuration. The occluder frame segments 386 may include coupling frame segments 400 and intermediate frame segments 402 (or conforming or stabilizing frame segments), the intermediate frame segments 402 and coupling frame segments 400 extending to the outer periphery in an alternating manner such that the intermediate frame segments 402 extend between each of the coupling frame segments 400. The coupling frame segments 400 may be thicker than the intermediate frame segments 402. That is, the coupling frame segments 400 may include a greater width than the intermediate frame segments 402. The intermediate frame segments 402 interconnect the coupling frame segments 400 with a v-configuration and may provide additional conformability of the occluder portion 362 with the anatomy of the left atrial appendage. The intermediate frame segments 402 provide additional support and points of contact to push and maintain the tissue growth member 388 (FIG. 21) against the tissue so that the occluder portion 362 conforms and stabilizes the tissue growth member 388 against tissue in the left atrial appendage.

The coupling frame segments 400, adjacent the proximal end 390 or central portion, may include a first opening 404, a second opening 406 and a fixture holding piece 408. The first opening 404 may be sized and configured to couple to retainer fingers 430 of the hub 382 (FIG. 27), discussed in further detail herein. The second opening 406 may be sized and configured to stitch the first layer 394 of the tissue growth member 388 to the occluder frame segments 386. The fixture holding piece 408 may be sized and configured to hold the occluder frame 366 through various frame preparation processes, such as electro-polishing. Once the preparation processes are complete the fixture holding piece 408 may be removed.

Further, adjacent the distal end 392 of each of coupling frame segments 400, the coupling frame segments 400 may include an occluder aperture 410 and a third opening 412. The occluder aperture 410 may be sized and configured to couple the occluder frame segments 386 to the anchor portion 364 in a pivotable or hinged manner. The third opening 412 may be utilized as another opening for stitching the first layer 394 of the tissue growth member 388 (FIG. 22) to the occluder frame segments 386.

Figure 24:
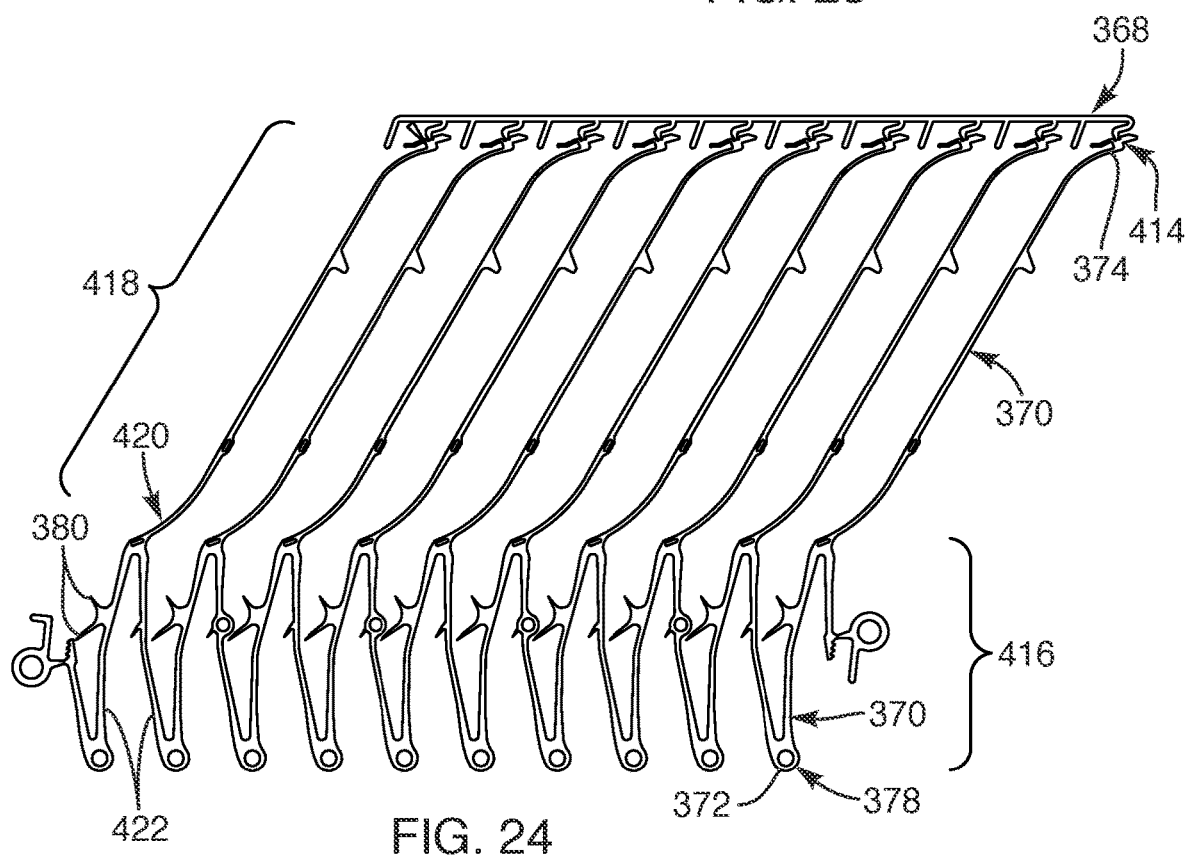
FIG. 24 is a top view of an anchor portion, depicting the anchor frame as cut from a flat sheet of material, according to another embodiment of the present invention.

Now with reference to FIG. 24, the anchor frame 368 is depicted as-cut from sheet material, similar to previous embodiments, having a monolithic seamless structure. As in the previous embodiments, the anchor frame segments 370 of the anchor frame 368 may extend between the first end 372 and the second end 374. The first end 372 or first end portion may define the anchor aperture 378 and the second end 374 or second end portion may include a hub coupling portion 414. The anchor aperture 378 may be sized and configured to couple to the occluder aperture 410 defined in the occluder frame segments 386 to facilitate a pivotable or hinge connection. The hub coupling portion 414 may be coupled to the anchor hub 376 (FIG. 22).

The anchor frame 368 may include an anchor tine portion 416 and extensions 418 extending between the first and second ends 372, 374 to define the multiple anchor frame segments 386. The extensions 418 may include a flexure portion 420 adjacently extending from the anchor tine portion 416, the extensions 418 continuing to the hub coupling portion 414 and first end 372 of the anchor frame 368. The anchor tine portion 416 may exhibit a zig-zag arrangement or strut segments 422 having multiple v-configurations coupled together. The anchor tine portion 416 may extend between the anchor apertures 378 and ends of the extensions 418. Further, the anchor tine portion 416 may include one or more tines 380 extending from the strut segments 422. In one embodiment, the strut segments 422 may include tines 380 extending proximally and distally. In another embodiment, some of the strut segments 422 may include tines 380 extending both proximally and distally with other ones of the strut segments 422 having tines 380 that only extend proximally toward the anchor aperture 378.

With respect to FIGS. 23 and 24, in one embodiment, anchor frame 368 and occluder frame 366 may be laser cut from a flat sheet of super elastic material, such as Nitinol. The anchor frame 368 and occluder frame 366 may then be positioned with fixtures and heat-set in, for example, a sand bath to set and form the anchor frame 368 and occluder frame 366 in the shape as depicted in FIG. 22. Upon the anchor frame 368 and occluder frame 366 being heat-set, the hub 382 may be secured to the proximal end 390 of the occluder frame segments 386.

With respect to FIGS. 25, 25A, 26, and 26A, the hub 382 or primary hub is provided. The hub 382 may include a hub retainer 424 and a hub portion 434. The hub retainer 424, as depicted in FIGS. 25 and 25A, may include a cylindrical portion 426 defining a retainer bore 428 extending therethrough. The cylindrical portion 426 may include retainer fingers 430 extending from one end thereof and extending and spaced evenly about a periphery of the one end of the cylindrical portion 426. The retainer fingers 430 may extend radially from the one end to a free end 432. Such retainer fingers 430 may be sized and configured to extend through the first opening 404 adjacent the proximal end 390 of the occluder frame segments 386.

With respect to FIGS. 26 and 26A, the hub portion 434 may include a somewhat cylindrical outer surface 436 and back-stop 438 in the form of a head portion, the hub portion 434 defining a hub bore 440 extending therethrough. The hub bore 440 may define the axis 384 of the medical device 360 (see also FIG. 21). Further, the hub bore 440 may define structure sized and configured to interact with the delivery catheter, such as a circumferential recess 442 defined in the hub bore 440.

With respect to FIGS. 25A, 26A and 27, the hub 382 may be assembled and coupled to the occluder frame segments 386. For example, the retainer fingers 430 may be inserted through the first opening 404 of the occluder frame segments 386. The cylindrical outer surface 436 of the hub portion 434 may then be inserted and positioned within the retainer bore 428 so that the free end 432 of the retainer fingers 430 abut the back-stop 438 of the hub portion 434, as depicted in FIG. 27, so that the occluder frame segments 386 may be secured to the retainer fingers 430. The hub retainer 424 and the hub portion 434 may be secured together via a weld or adhesive or any other suitable method, such as by welding a seam between the hub retainer 424 and the hub portion 434. As previously set forth, the retainer fingers 430 of the hub retainer 424 may extend through corresponding first openings 404 of the occluder frame segments 386 such that the occluder frame segments 386 may be moveable, to an extent, over the retainer fingers 430 so that the occluder frame segments 386 may pivot at the proximal end 390 thereof over the retainer fingers 430. With this arrangement, the occluder frame segments 386 may be pivotably coupled to the hub 382 at the proximal end 390 of the occluder frame segments 386. Further, in this manner, the occluder portion 362 may readily constrict and pivot to an occluder constricted state within the sheath 316 of the delivery system 302 and, upon the occluder portion 362 being moved out of the sheath 316, the occluder frame segments 386 may pivot so that the occluder portion 362 self-expands to a radially expanded position or occluder deployed position (see FIG. 18).

Now with reference to FIGS. 28-35, various embodiments of an anchor portion, depicting various tine geometries, sized and configured to be coupled (or operatively coupled) to any one of the occluder portion embodiments set forth herein are provided. As such, any one of the anchor portion embodiments may be employed as the anchor portion to form a medical device, such as depicted in FIGS. 1 and 21, sized and configured to implant within the left atrial appendage as described herein. Several considerations are made relative to tine geometries for a given anchor portion. The different structural characteristics of the various tine geometries depicted in the anchor portion embodiments herein may have preferable tine geometries dependent upon several factors relating to, for example, the structural characteristics and dimensions with a particular anchor portion and/or occluder portion of the medical device.

One consideration and aspect of tine geometry relates to a tine height of a given tine or tines of a given anchor portion. For example, increasing the tine height may provide increased anchoring effectiveness but may also increase the amount of potential tissue damage that may occur when the device is pulled upon with enough force to drag the tines through the tissue. Likewise, a decrease in tine height may lower the anchoring effectiveness and may decrease potential tissue damage upon pulling the device before it is detached from the delivery catheter. It has been found that a preferable tine height may be dependent upon several factors, such as tine angle and spacing between adjacent tines. In one embodiment, a preferable height of a tine may be about 0.032 inches and range between about 0.020 inches and about 0.050 inches. In addition, tines on struts that may be somewhat bowed may cause the tines to be more prominent than surrounding features of the device and, thus, may engage the tissue more reliably. Such prominence in the tines may increase the effective height of the tines and thus increase anchoring effectiveness, but may also create inconsistency in situations where the tines contact tissue at a rear wall of the left atrial appendage. In some embodiments and for consistency purposes, it may be preferable to limit bowing of the struts.

Another consideration of tine geometry relates to an angle that a given tine extends from a strut of the anchor portion. For example, minimizing an angle of the tines may improve the "grab" of the tines, but may also tend to hinder releasing the tissue upon retracting the anchor portion if re-positioning the device is desired. It has been found that an angle of the tine, relative to the strut it extends from, between about 25 degrees and about 60 degrees may be optimal for engaging tissue as well as releasing from the tissue. The tine height and spacing between adjacent tines may be factors for determining a preferred angle of the tines.

Another factor for tine geometry may include the alignment of the tines relative to the struts or axis of the device. For example, tines may be configured to align with the axis of the device. That is, tines may be formed to be non-aligned with the struts of the zig-zag pattern of an anchor portion such that the tines are substantially aligned with the axis of the medical device or such that a given tine may extend substantially within a plane defined by a given tine and the axis. The tines that may be aligned with the axis of the medical device may engage the tissue more securely, but also may cause more damage to the tissue when the device is pulled upon by the delivery catheter. On the other hand, tines aligned with struts that extend in the before-discussed zig-zag pattern, as depicted in FIGS. 2 and 22 herein, may not be aligned with the axis of the device such that a plane including the strut and the tines extending from the strut is transverse to the axis of the device. It has been found that tines aligned with the struts of the zig-zag pattern may provide sufficient grab for engaging tissue as well as provide better releasing of tissue so as to minimize any potential damage to the tissue.

Another consideration for tine geometries may include spacing and quantity of tines on a given strut of an anchor portion. For example, tines on a given strut that may be too close to another tine may lose engagement effectiveness due to load sharing. In other words, tines that are too close to another strut may result in a "bed of nails" effect. As such, adding additional tines in some cases or spacing between tines being too close may not result in higher retention forces. It is therefore desirable to have at least a predetermined distance for the spacing between adjacent tines along a given strut for the tines to effectively engage the tissue in the LAA. Dependent upon several factors, such as tine angle and tine height, a preferred spacing between adjacent tines may be in the range of between about 0.060 inches and about 0.150 inches or the range between about 0.060 inches and about 0.120 inches.

Further, the sharpness of the tine tips may be another consideration relating to tine geometry. For example, sharper tine tips may yield better tissue engagement with a lower radial force. Another consideration for tine geometries may include tine flexibility, however, due to the height of the tines being minimal, the flexibility of the tines and the struts on which they extend from does not appear to be significant relative to the compliance of the tissue. In regard to the radial force of the anchor portion against the tissue, it has been found that increased radial force provided by the anchor portion and/or the occluder portion leads to increased retention against pull-out forces. Such increased radial force relative to increased retention appears to be a somewhat linear relationship.

As can be appreciated, there are several factors that may be considered relating to tine geometry. It is desirable for the tines of the anchor portion be reliable to effectively engage the tissue without extending completely through the tissue to potentially cause perfusions as well as tine geometries that readily release from the tissue upon retracting the anchor portion from the tissue in the LAA. Various embodiments of tine geometries associated with an anchor portion will now be described.

Figure 28:
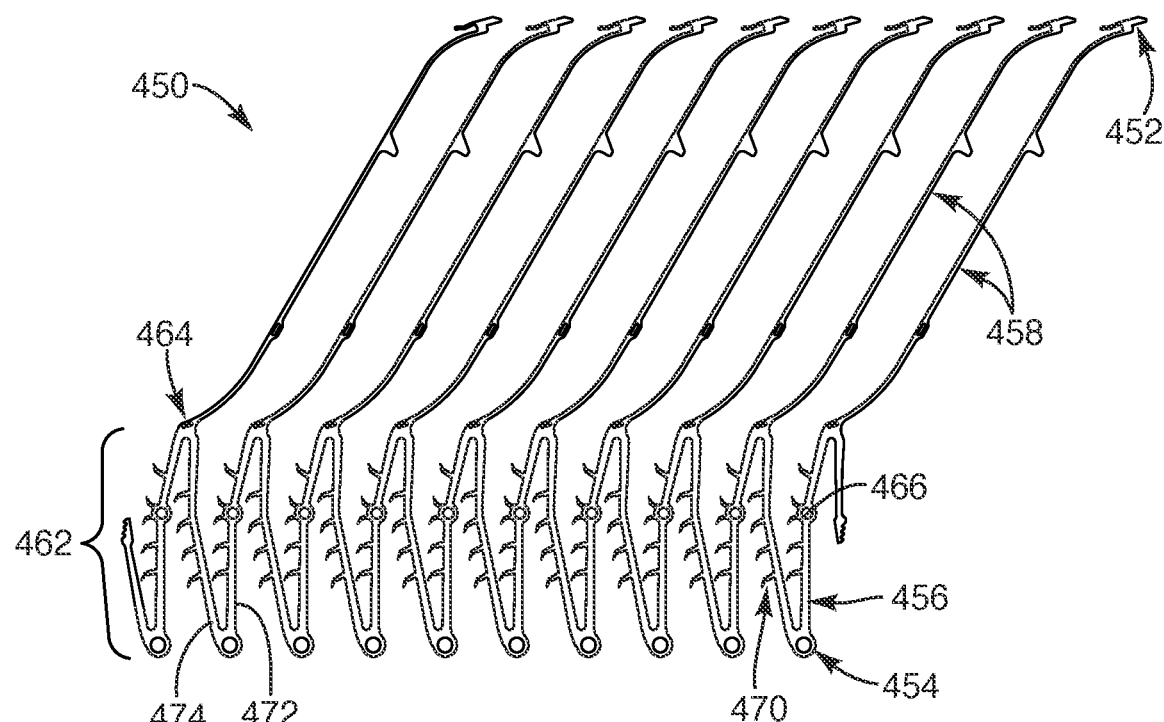
FIG. 28 is a top view of another embodiment of an anchor portion, depicting the anchor portion as cut from a flat sheet, according to the present invention.
Figure 28A:
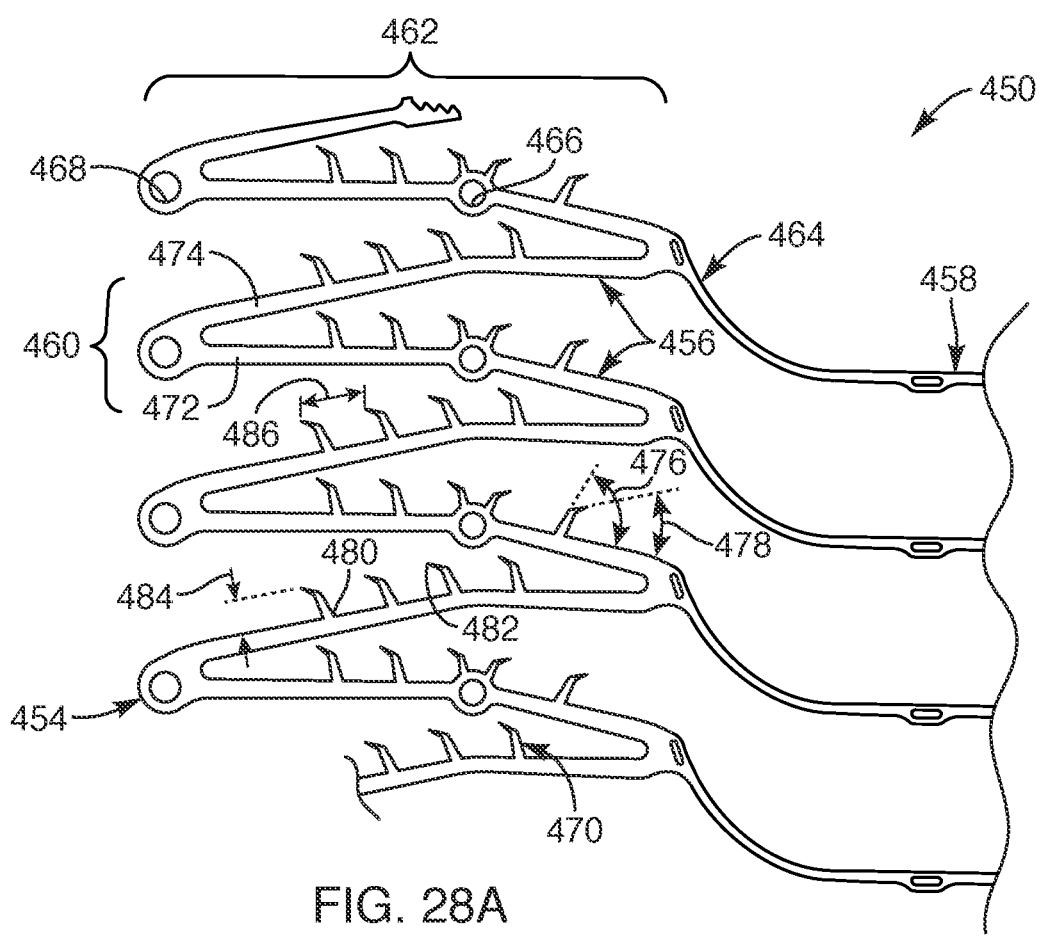
FIG. 28A is an enlarged view of a portion of the anchor portion of FIG. 28, depicting tines extending from struts of the anchor portion, according to another embodiment of the present invention.

With respect to FIGS. 28 and 28A, an anchor portion 450 may be formed from a flat sheet of metal, such as Nitinol, by for example, laser cutting, similar to that described in previous embodiments herein. Similar to previous embodiments, this embodiment of the anchor portion 450 may extend between a first end 452 and a second end 454 such that the first end 452 may couple to an anchor hub 376 (FIG. 22) and the second end 454 may couple to a distal end or end portion of an occluder portion 366 (FIG. 22). Further, similar to previous embodiments, the anchor portion 450 may include structure defining anchor struts 456 and anchor actuator arms 458. The anchor struts 456 may extend to form multiple anchor v-extensions 460 to define an anchor zig-zag portion 462. The anchor actuator arms 458 may extend from ends of the anchor v-extensions 460 to the first end 452 of the anchor portion 450. Further, the anchor actuator arms 458 may define a flexure portion 464 that may extend with a radius from the anchor v-extensions 460 and may taper along such radius. The flexure portion 464 may include structural characteristics to facilitate actuating the anchor portion 450 between a retracted position and the deployed position, as set forth in previous embodiments. Further, the anchor portion 450 may define one or more apertures 466 formed in at least some of the anchor struts 456 of the anchor v-extensions 460. For example, at the second end of the anchor portion or end of the v-extension, one of the apertures may be employed as a coupling aperture 468 or an anchor eyelet sized and configured to couple to the occluder portion similar to that depicted in FIG. 3B. Further, for example, the one or more apertures 466 may be positioned along a portion or mid-portion of one of the anchor struts 456 so as to be sized and configured to receive a marker (not shown). The one or more apertures 466 sized to receive a marker may be included along every other anchor strut along the anchor zig-zag portion 462 of the anchor portion 450.

In this embodiment, the anchor portion 450 may include anchor hooks 470 or tines extending along the anchor struts 456 of a given anchor v-extension 460. For example, in a given anchor v-extension 460 of the anchor struts 456, the anchor v-extension 460 may extend with a first strut 472 and a second strut 474. Along the first strut 472, the first strut may define one of the apertures 466 and the second strut 474 may extend continuously without an aperture. The first strut 472 may define multiple anchor hooks 470 or otherwise referenced as tines. Some of the anchor hooks 470 of the first strut 472 may be oriented to extend proximally and some of the anchor hooks 470 may be oriented to extend distally. The second strut 474 may also define multiple anchor hooks 470. Such anchor hooks 470 of the second strut 474 may be oriented to extend proximally such that no anchor hooks extend distally along the second strut 474.

In one embodiment, the anchor hooks 470 may extend relative to the anchor strut 456 at a first acute angle 476 and a second acute angle 478. For example, the anchor hooks 470 may extend from a base 480 to a mid portion to define the first acute angle 476. At the mid portion or mid-height of the anchor hooks 470, the anchor hooks 470 may transition to the second acute angle 478 to further extend toward a tip 482 or end of the anchor hooks 470, the first acute angle 476 being greater than the second acute angle 478. In this manner, the anchor hooks 470 may be oriented to extend proximally and/or distally and then be further oriented to extend more proximally and/or more distally so as to exhibit a dual angled hook. In one embodiment, the first acute angle 476 may be about 70 degrees or within the range of about 45 degrees to about 75 degrees. The second acute angle 478 may be about 25 degrees or within the range to about 20 degrees to about 60 degrees.

In one embodiment, in a given anchor v-extension 460, the first strut 472 may include three anchor hooks 470 that extend proximally and two anchor hooks 470 that extend distally. The second strut 474 may include four anchor hooks 470 that extend proximally. The aperture 466 sized for receiving a marker (not shown), as set forth above, may include one anchor hook 470 extending proximally at one side of the structure defining the aperture 466 and another anchor hook 470 extending distally at another side of the structure defining the aperture 466 such that the aperture 466 defines a transition between anchor hooks 470 extending proximally and distally. From this transition, the anchor hooks 470 extending proximally may be substantially evenly spaced relative to each other along the first strut 472. The anchor hooks 470 extending distally may include a similar spacing or include a larger spacing as the anchor hooks 470 that extend proximally. Along the second strut 474, the anchor hooks 470 that extend proximally may be substantially evenly spaced relative to each other. The spacing between anchor hooks 470 may be sized and configured such that each anchor hook 470 may effectively engage tissue without interfering with adjacently positioned anchor hooks 470. As previously set forth, spacing of adjacent hooks on a given strut that are too close may result in load sharing and may lose their individual engagement or anchoring effectiveness. For example, spacing 486 between adjacently extending hooks may be about 0.065 inches or may be in the range of about 0.06 inches to about 0.12 inches.

The anchor hooks 470 that extend proximally and distally may include a common height 484 relative to the first or second strut 472, 474, the height 484 defined from the base 480 to the tip 482. Such height 484 may be a predetermined height sized to facilitate engagement, or even aggressive engagement, of the tissue in the LAA, but a height sized to not puncture all the way through the tissue at or adjacent the ostium of the LAA. For example, the height 484 may be about 0.032 inches or within the range of about 0.020 inches and about 0.050 inches. Further, the depth or thickness 92 (FIG. 2) of each anchor hook 470 may be defined by the thickness of the flat sheet from which the anchor portion 450 is cut. As such, the tip 482 of the anchor hooks 470 may define an edge, the edge defined by the thickness of the sheet material. In one embodiment, the sheet material employed may be sized such that the tip of the anchor hooks defines a point. In this manner, the thickness of the sheet material employed for cutting the anchor portion 470 may directly correlate with whether the tip defines an edge or resembles more a point. Other factors that may be effective to reduce an edge to a point may include the manufacturing processes of abrasive blasting and/or electropolishing.

Figure 29:
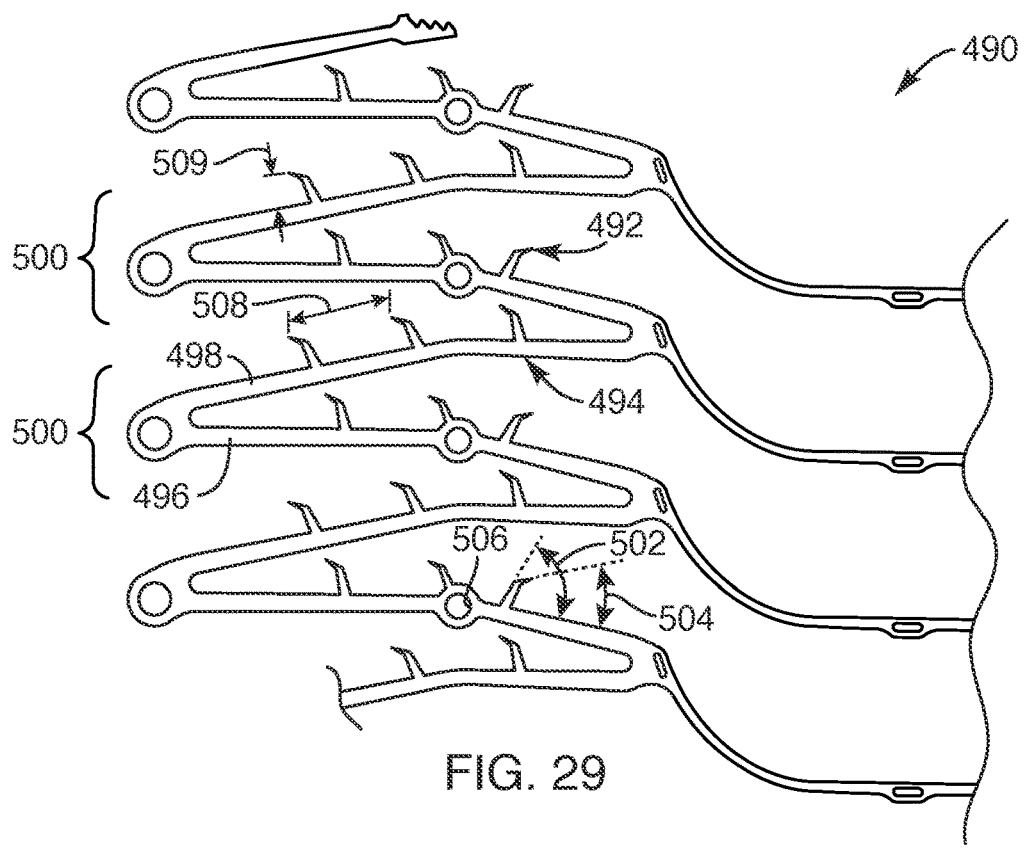
FIG. 29 is an enlarged view of another embodiment of tines extending from struts of an anchor portion, according to the present invention.

With respect to FIG. 29, another embodiment of an anchor portion 490 with anchor hooks 492 extending from anchor struts 494 of the anchor portion 490 is provided. This embodiment may be similar to the previous embodiment, except in this embodiment first and second struts 496, 498 of the anchor v-extension 500 may define less anchor hooks 492 than the previous embodiment. For example, the first strut 496 may define multiple anchor hooks 492, such as two anchor hooks that extend proximally and one anchor hook that extends distally. Further, the second strut 498 may include three anchor hooks 492 that extend proximally. The anchor hooks 492 of the second strut 498 may be evenly spaced relative to each other so as to define a spacing 508. The spacing 508 of the anchor hooks 492 that extend proximally of both the first and second struts 496, 498 may include a substantially common spacing 508 between the anchor hooks 492. For example, the spacing 508 of adjacently extending anchor hooks 492 of this embodiment may be about 0.100 inches or range between about 0.060 inches and about 0.120 inches. In addition, the anchor hooks 492 may include a height 509, the height 509 being about 0.032 inches and include similar ranges as set forth in the previous embodiment. Further, similar to the previous embodiment, each of the anchor hooks 492 may extend proximally or distally with a first acute angle 502 and a second acute angle 504 to exhibit a dual angled hook such that the first acute angle 502 may be greater than the second acute angle 504. Such first and second acute angles 502, 504 may include similar angle ranges as set forth in the previous embodiment. As in the previous embodiment, at the aperture 506 sized for a marker defined in the first strut 496, only one anchor may extend from the structure defining such aperture 506, rather than two anchor hooks as set forth in the previous embodiment.

Figure 30:
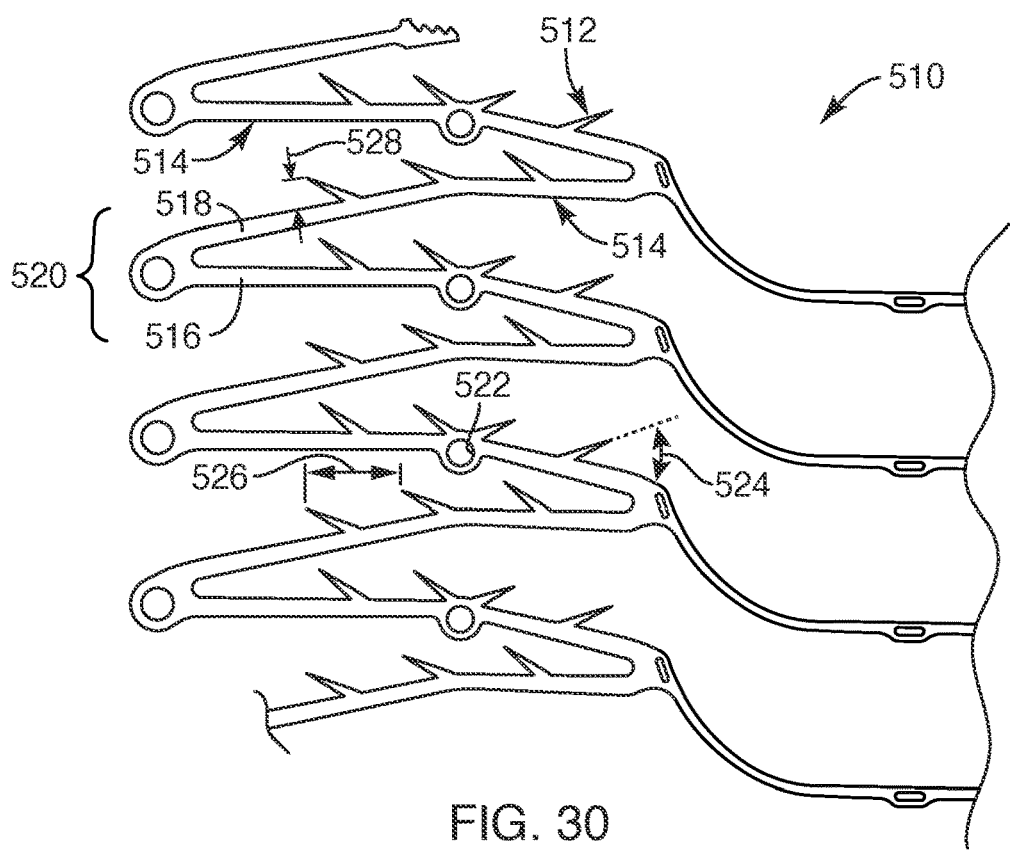
FIG. 30 is an enlarged view of another embodiment of tines extending from struts of an anchor portion, according to the present invention.

With respect to FIG. 30, another embodiment of an anchor portion 510 with anchor hooks 512 extending from anchor struts 514 of the anchor portion 510 is provided. In this embodiment, the anchor hooks 512 may extend along a first strut 516 and a second strut 518 of a given anchor v-extension 520. Along the first strut 516, the anchor hooks 512 may extend both proximally and distally. For example, the first strut 516 may include two anchor hooks 512 extending proximally and two anchor hooks 512 that extend distally. The two anchor hooks 512 extending proximally may include a spacing 526 which may be common or substantially similar to the spacing between the two anchor hooks 512 that extend distally. Such spacing 526 may be about 0.100 inches and may range between about 0.060 inches and about 0.120 inches. Further, the first strut 516 includes structure defining an aperture 522 such that one anchor hook extends proximally from the structure that defines the aperture 522 and another anchor hook extends distally from the structure that defines the aperture 522. The second strut 518 may include three anchor hooks 512 extending proximally such that each of the three anchor hooks 512 include a substantially common spacing relative to adjacently extending anchor hooks 512. Similar to other embodiments set forth herein, each of the anchor hooks 512 may define a single acute angle 524 relative to and extending from the anchor strut from which the anchor hook 512 extends from. Such single acute angle 524 of a given anchor hook 512 may be about 30 degrees and may extend in the range of about 25 degrees to about 60 degrees. Further, a height 528 of the anchor hooks 512 may be about 0.032 inches and may range between about 0.020 inches and about 0.050 inches.

Figure 31:
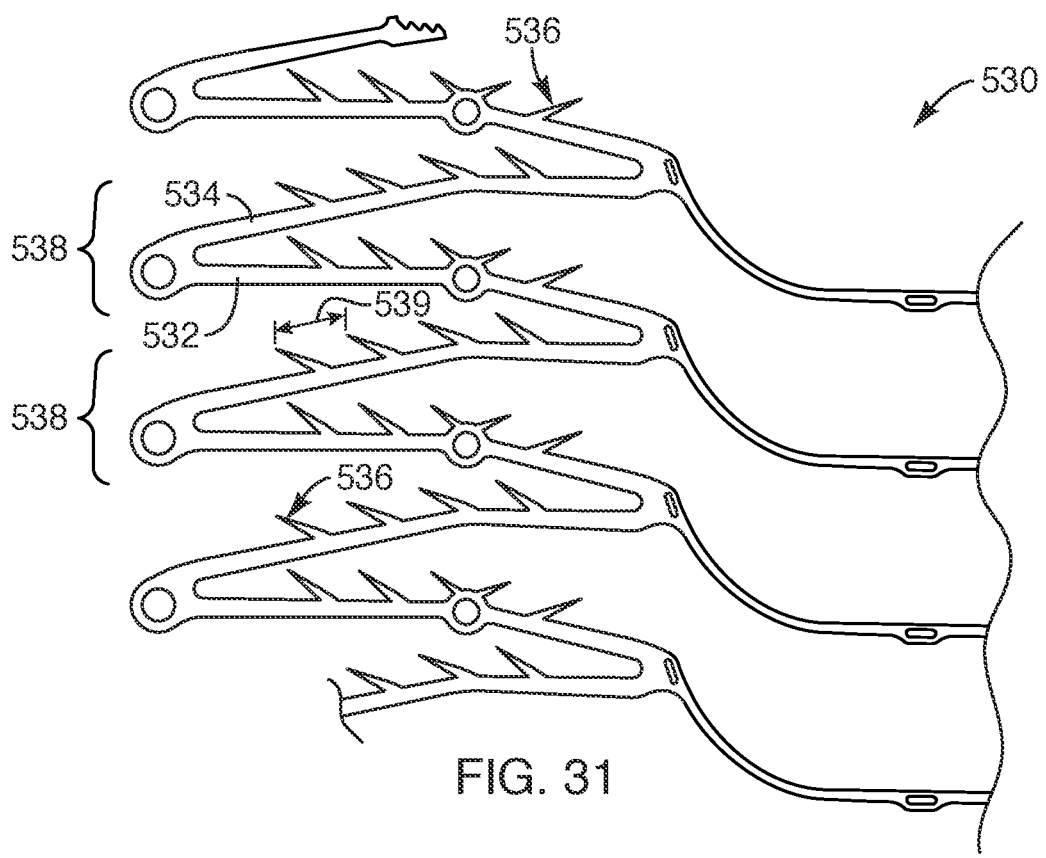
FIG. 31 is an enlarged view of another embodiment of tines extending from struts of an anchor portion, according to the present invention.

In another embodiment, as depicted in FIG. 31 and similar to the previous embodiment of FIG. 30, an anchor portion 530 with first and second struts 532, 534 may include additional anchor hooks 536 along each of the first and second struts 532, 534 of anchor v-extensions 538 of the anchor portion, the anchor hooks 536 having a similar angle and height with similar ranges as the previous embodiment. For example, the first strut 532 may include three anchor hooks 536 extending proximally and two anchor hooks 536 extending distally. The second strut 534 may include four anchor hooks 536 extending proximally without any anchor hooks that extend distally. Further, a spacing 539 between proximally extending anchor hooks 536 may be common or substantially similar with the spacing between distally extending anchor hooks 536. For example, the spacing 539 between adjacent anchor hooks 536 that extend in common directions may be about 0.073 inches or range between about 0.060 inches and about 0.120 inches.

Figure 32:
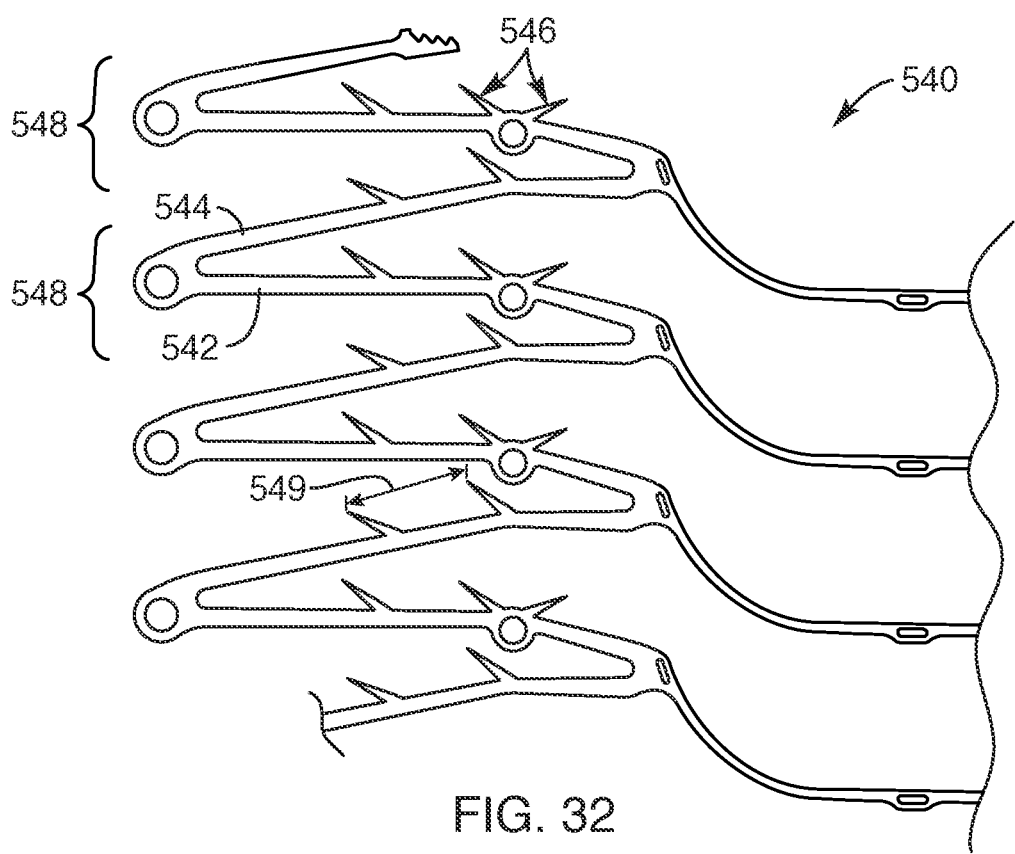
FIG. 32 is an enlarged view of another embodiment of tines extending from struts of an anchor portion, according to the present invention.

Further, in another embodiment, as depicted in FIG. 32 and similar to the embodiment of FIG. 30, an anchor portion 540 with first and second struts 542, 544 may include less anchor hooks 546 extending from anchor v-extensions 548 of the anchor portion 540. For example, the first strut 542 may include three anchor hooks 546, two anchor hooks extending proximally and one anchor hook extending distally. The second strut 544 may include two anchor hooks 546 extending proximally without any anchor hooks extending distally. Further, the anchor hooks 546 may define a height and angle similar to the previous embodiment with similar ranges, but a spacing 549 defined between the anchor hooks 546 may be different than the previous embodiments. For example, the spacing 549 between proximally extending anchor hooks 546 may be about 0.120 inches or between about 0.100 inches and about 0.150 inches.

Figure 33:
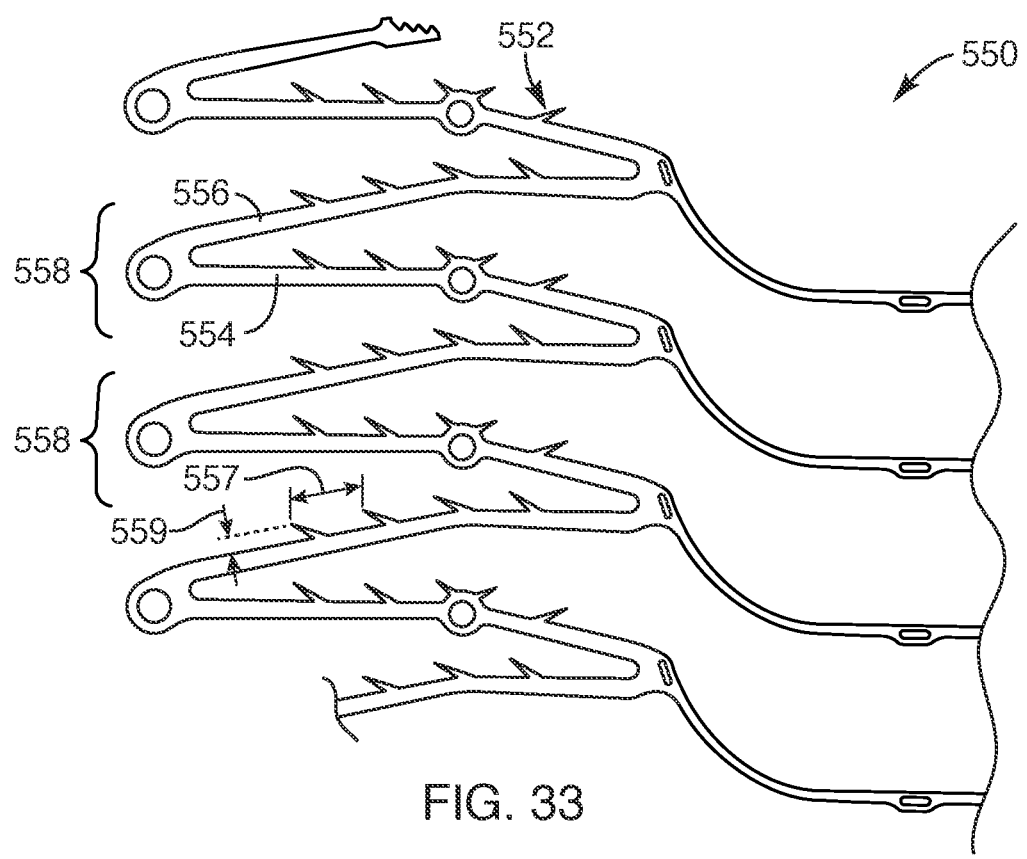
FIG. 33 is an enlarged view of another embodiment of tines extending from struts of an anchor portion, according to the present invention.

In still another embodiment, as depicted in FIG. 33, an anchor portion 550 with anchor hooks 552 extending from first and second struts 554, 556 of anchor v-extensions 558 of the anchor portion 550 may be smaller in height than that depicted in previous anchor hook embodiments. For example, the anchor hooks 552 may define a height 559 of about 0.020 inches and a range of about 0.015 inches to about 0.030 inches. Further, a spacing 557 between commonly extending adjacent anchor hooks 552 may be about 0.073 inches and range between about 0.060 inches and about 0.120 inches. The anchor hooks, similar to previous embodiments, may define an acute angle of about 30 degrees or be in the range of about 25 degrees and about 60 degrees.

Figure 34:
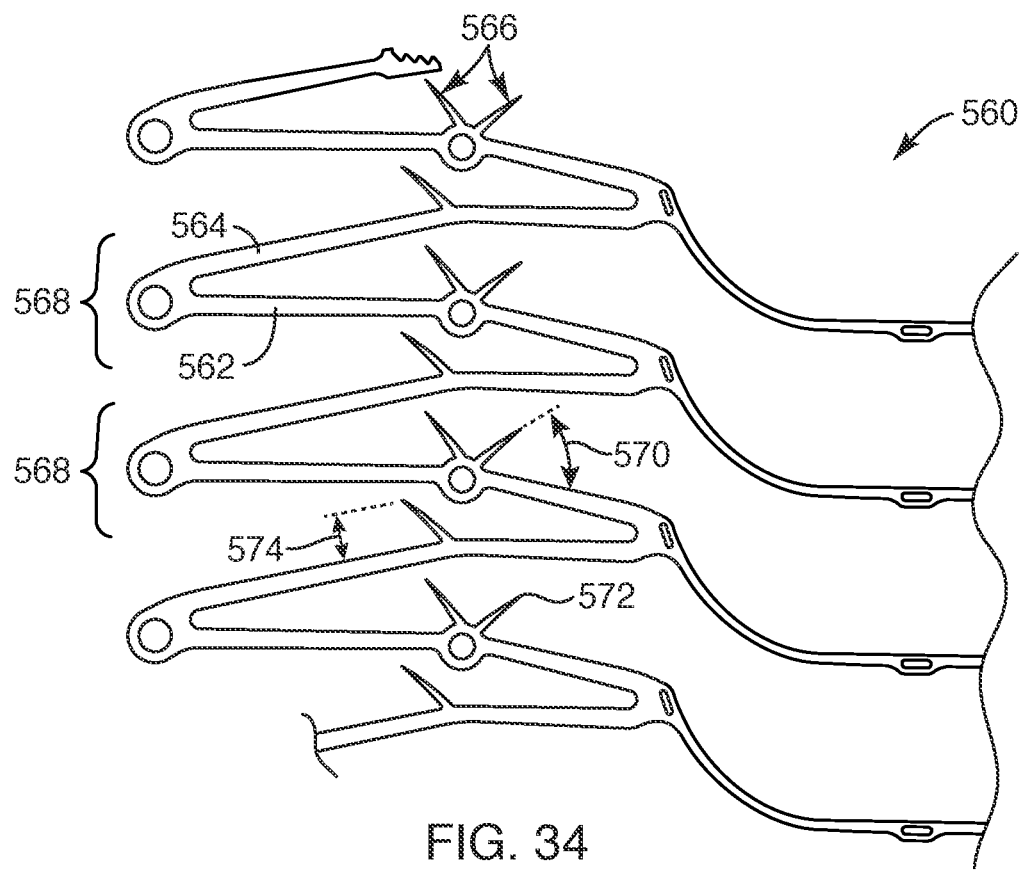
FIG. 34 is an enlarged view of another embodiment of tines extending from struts of an anchor portion, according to the present invention.

With respect to FIG. 34, in another embodiment, an anchor portion 560 may include first and second struts 562, 564 with minimal anchor hooks 566 extending from anchor v-extensions 568 of the anchor portion 560. For example, the first strut 562 may include a single anchor hook 566 extending proximally and a single anchor hook 566 extending distally. The second strut 564 may include a single anchor hook 566 extending proximally therefrom. Further, the anchor hooks 566 may extend with an acute angle 570. The acute angle 570 may be about 45 degrees or in the range of about 25 degrees to about 60 degrees. The anchor hooks 566 may extend to a point 572 or an edge at a free end thereof to define a height 574 relative to the corresponding first strut 562 or the second strut 564. For example, the height 574 of the anchor hooks 566 may be about 0.050 inches. In comparison to previous embodiments, the height 574 and angle 570 of the anchor hooks 566 may be more prominent to anchor hooks of previous embodiments, but may also include a fewer number of anchor hooks 566. In another embodiment, the height may be about 0.032 inches and range between about 0.020 inches and about 0.060 inches.

Figure 35:
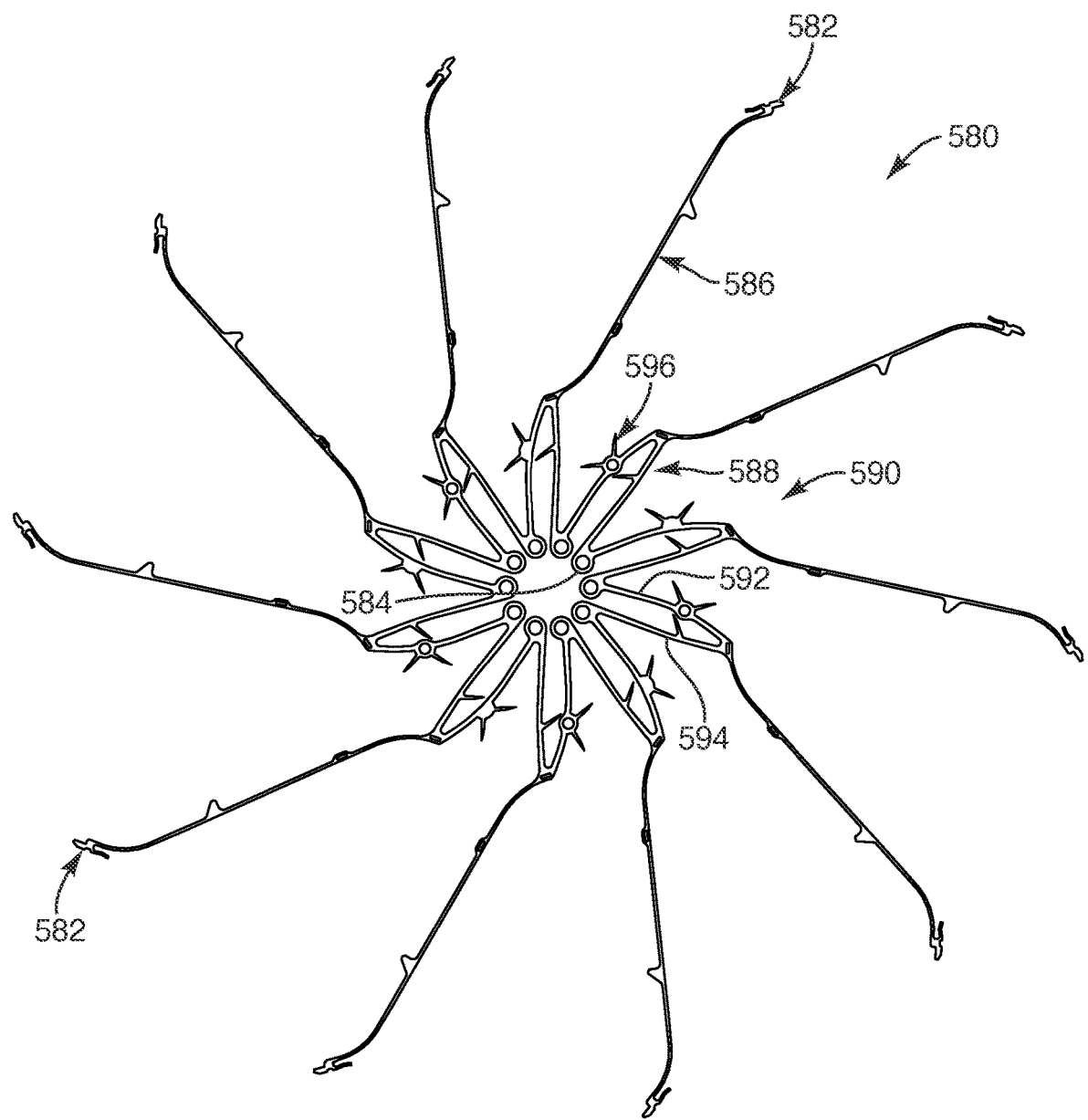
FIG. 35 is a top view of another embodiment of an anchor portion, depicting the anchor portion extending in a radial pattern, according to the present invention.

With respect to FIG. 35, another embodiment of an anchor portion 580 is provided. In this embodiment, the anchor portion 580 may be cut from a flat sheet of, for example, Nitinol in a radial arrangement or radial pattern, similar to the occluder portion 366 depicted in FIG. 23. The anchor portion being cut in the radial arrangement may be heat-set to a formed shape similar to the anchor portions of previous embodiments, depicted for example in FIGS. 2 and 22. Upon being heat-set and formed as desired, the anchor portion 580 may extend between a first end 582 and a second end 584. The first end 582 may couple to an anchor hub 376 (FIG. 22) and the second end 584 may couple to a distal end or end portion of an occluder portion 366 (FIG. 22), similar to previous embodiments. The anchor portion 580 may define anchor actuator arms 586 extending from ends of anchor v-extensions 588, the anchor v-extensions 588 continuously extending to define an anchor zig-zag portion 590. Each of the anchor v-extensions 588 may define a first strut 592 and a second strut 594 extending to exhibit a v-configuration. As in previous embodiments, the first and second struts 592, 594 may include anchor hooks 596 or tines extending therefrom. In this embodiment, the first strut 592 may include two anchor hooks 596 and the second strut 594 may include one anchor hook 596, similar to the previous embodiment depicted in FIG. 34. Such first and second struts 592, 594 may include additional anchor hooks 596 or less or any one of the anchor hook variations and structural characteristics of the tine geometries as set forth in any one of the anchor portion embodiments described herein. In other words, any one of the anchor portion embodiments described herein may be cut from a flat sheet in a radial arrangement or radial pattern, similar to that set forth in FIG. 35.

Now with reference to FIGS. 36 and 37, another embodiment of a medical device 600, similar to that described and depicted relative to FIGS. 21 and 22, except in this embodiment the occluder portion may include alternate occluder materials. As in previous embodiments, the medical device 600 of this embodiment may include an anchor portion 602 and an occluder portion 604. The anchor portion 602 may be formed from any one of the anchor portion embodiments cut from, for example, a flat sheet as set forth herein to a radially extending position, as depicted in FIG. 36, through a heat-setting process as known to one of ordinary skill in the art. Further, as in previous embodiments, a first end 606 of the anchor portion 602 may be coupled to an anchor hub 610 and a second end 608 of the anchor portion 602 may be hingeably or pivotably coupled to a distal end 612 of the occluder portion 604 with a proximal end 614 of the occluder portion 604 being coupled to a hub 616 with a first part 618 and a second part 620. With this arrangement, the anchor portion 602 may be movable between retracted and deployed positions with the anchor hub 610 being moveable along an axis 622 between respective proximal and distal positions while the occluder portion is in an expanded position, as described herein.

In this embodiment, the occluder portion 604 may include an occluder frame portion 624 and a tissue growth member 626. The tissue growth member 626 may also be referenced as an occluder material portion or a polymeric material portion. The occluder frame portion 624 may also be formed from any one of the occluder frame embodiments cut from a flat sheet of, for example, Nitinol, as set forth herein to a radially extending position, as depicted in FIG. 36, through a heat-setting process. In another embodiment, the occluder frame portion and/or the anchor portion may be cut from tubular stock, rather than from a flat sheet, and then may be formed into the radially extending positions, as depicted in FIG. 36.

With reference to FIGS. 36 and 37A, in one embodiment, the tissue growth member 626 may include multiple layers and portions. For example, the tissue growth member 626 may include an inner portion 628 and an outer portion 630 with a middle portion 632 positioned therebetween. Such tissue growth member 626 may include similar structural characteristics to that described relative to FIG. 22, such as, being impermeable or impervious so as to not allow blood to flow through the tissue growth member. In one embodiment, the inner portion 628 may be positioned so that an inner surface 634 of the inner portion 628 extends over and directly contacts an outer surface 636 of the occluder frame portion 624 with at least one layer of a polymeric material, such as a woven or non-woven material. With this arrangement, the inner portion 628 may be adhesively attached and/or stitched with filaments to the outer surface 636 of struts 638 of the occluder frame portion 624. Further, in this embodiment, the inner portion 628 may be formed with one or more layers of a polymeric material. The polymeric material may include one or more filaments that may be a knitted, weaved, or braided fabric or combinations thereof so as to provide a regular or substantially consistent pattern to form, for example, a mesh material. In another embodiment, the polymeric material may include one or more filaments formed in a random or arbitrary pattern. In another embodiment, the polymeric material may be made from any suitable medical grade polymeric material, such as polyester, polypropylene, or polyethylene, or any other medical grade polymeric material, or the like.

In another embodiment, the inner portion 628 may be a non-woven fabric. The non-woven fabric may be formed of polymeric filaments. For example, the non-woven fabric may be formed with random fibers that may be adhered together with various processes, such as heat pressing or with solvents as known by one of ordinary skill in the art, or any other suitable process for forming a non-woven fabric.

The middle portion 632 may be sized and configured to be positioned symmetrically along the axis 622 and over a central portion of the inner portion 628 and adjacent the hub 616 of the occluder frame portion 624. The middle portion 632 of the tissue growth member 626 may serve as a reinforcement layer. Such middle portion 632 may be desirable due to the increased stresses and tension resulting from pulling and constricting the medical device 600 within the sheath 102 of the medical device delivery system 100 (FIG. 4), the stresses over the medical device 600 being optimal adjacent the hub 61 of the occluder portion 604. The middle portion 632 may be disc shaped and may extend with less surface area than the inner and outer portions 628, 630 of the tissue growth member 626. The middle portion 632 may be a polymeric material, such as a woven or non-woven fabric material described herein or any other suitable polymeric material that may serve as a reinforcement layer. As such, the middle portion 632 may be formed of a similar or the same material as the inner portion 628. Further, the middle portion 632 may be adhesively attached to an outer surface of the inner portion 628 or stitched thereto with filaments.

The outer portion 630 of the tissue growth member 626 may be positioned over the outer surface or proximal side of the middle portion 632 and inner portion 628. The outer portion 630 may be formed with successive layering of polymeric materials each of which may be adhesively attached over the other. As in previous embodiments, the outer portion 630 of the tissue growth member 626 may be formed of multiple polymeric layers, such as ePTFE, defining, for example, a first layer 640, a second layer 642, and a third layer 644. In another embodiment, additional or less successive layering may be employed to form the outer portion 630. It should be noted that the tensile strength of some polymeric materials, such as ePTFE, may be strongest in a first direction and weakest in a direction ninety degrees out-of-phase or orthogonal relative to the first direction. As such, the successive layering of adjacent layers of the outer portion 630 may be transverse or out-of-phase to each other relative to their respective strongest direction of tensile strength. In this manner, the multiple layers of the outer portion 630 may be successively or consecutively attached to each other and formed to bolster the strength of the outer portion 630.

With respect to FIG. 37A, in another embodiment, the tissue growth member 626 may include a hydrophilic coating 652, represented by a dashed line. The hydrophilic coating 652 may be sized and configured to promote wettability of the tissue growth member 626 for purposes of imaging the device as well as act as a lubricant to minimize friction between the tissue growth member and the inner surface of the sheath 102 (see FIG. 4) as the device is delivered and advanced through the sheath 102, as described herein. Such hydrophilic coating 652 may be coated over the exposed portions of the tissue growth member 626 or may be coated over the outer surface of the outer portion 630 of the tissue growth member 626. The hydrophilic coating 652 may sprayed over portions of the tissue growth member 626 or the tissue growth member 626 may be dipped into a hydrophilic solution such that the hydrophilic solution may be integrated within the crevices of the tissue growth member 626 as well as cover the outer surfaces of the tissue growth member 626. The hydrophilic coating 652 of the tissue growth member may be any suitable medical grade hydrophilic coating material, as known to one of ordinary skill in the art.

With respect to FIGS. 36 and 37, the outer portion 630 may define a distal end portion 646 that extends further distally then a distal end 648 of the inner portion 628 of the tissue growth member 626. As such, the distal end portion 646 of the outer portion 630 may extend radially in the form of a ring without contacting the inner portion 628 of the tissue growth member 626. In another embodiment, the outer portion 630 and the inner portion 628 may extend distally a substantially equal amount. In still another embodiment, the inner portion 628 may define a distal end portion that extends further distally beyond a distal end of the outer portion, similar to that depicted in FIG. 1A.

Upon the medical device 600 being implanted in the LAA, the inner portion 628 of the tissue growth member 626 may face and be exposed to the LAA and the outer portion 630 of the tissue growth member 626 may face and be exposed to the left atrium of the heart. As set forth, the inner portion 628 may be formed of a polymeric material, such as a woven or non-woven fabric or the like. The woven or non-woven fabric may include structural characteristics configured to aggressively promote and enhance tissue growth within and over the polymeric layer. The outer portion 630, also being formed of a polymeric material such as ePTFE, may include structural characteristics to promote the formation of a smooth endothelization layer over the proximal side or outer surface of the tissue growth member 626. In this manner, the medical device 600 may be implanted to permanently occlude the LAA.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes incorporating any portion of one embodiment with another embodiment, all modifications, equivalents, and alternatives falling within the spirit and scope of the invention as defined by the following appended claims.

What is claimed is:

1. A method for occluding a left atrial appendage of a heart, the method comprising:
  positioning a framework within the left atrial appendage such that the framework extends to define a proximal side and a distal side with an axis, the proximal side of the framework extends radially outward and distally from a primary hub, the distal side of the framework extends radially inward to a distal end of the framework and extends radially inward and proximally to a secondary hub such that the secondary hub is positioned proximal the distal end of the framework; and
  permanently implanting the framework in the left atrial appendage.

2. The method according to claim 1, wherein the positioning comprises securing the framework to tissue within the left atrial appendage with anchoring tines extending from anchor frame segments of the framework.

3. The method according to claim 1, wherein the positioning comprises pivoting anchor frame segments of the framework between a retracted position and a deployed position.

4. The method according to claim 1, wherein the positioning comprises positioning the framework with a polymeric member along the proximal side of the framework.

5. The method according to claim 1, wherein the positioning comprises moving anchor frame segments of the framework between a non-deployed position and a deployed position.

6. The method according to claim 1, wherein the positioning comprises moving anchor frame segments of the framework between a retracted position and a deployed position by moving the secondary hub along the axis.

7. The method according to claim 1, further comprising advancing the framework from a distal end of a sheath such that the framework at least partially self-expands.

8. The method according to claim 1, wherein the positioning comprises positioning the framework with a tissue growth member along the proximal side of the framework, the tissue growth member having a hydrophilic coating associated therewith.

9. A method for occluding a left atrial appendage of a heart, the method comprising:
  positioning a framework within the left atrial appendage such that the framework extends to define a proximal side and a distal side with an axis, the proximal side of the framework extends radially outward and distally from a primary hub, the distal side of the framework extends radially inward to a distal end of the framework and extends to a secondary hub such that the secondary hub is positioned proximal the distal end of the framework; and
  permanently implanting the framework in the left atrial appendage.

10. The method according to claim 9, wherein the positioning comprises securing the framework to tissue within the left atrial appendage with anchoring tines extending from anchor frame segments of the framework.

11. The method according to claim 9, wherein the positioning comprises pivoting anchor frame segments of the framework between a retracted position and a deployed position.

12. The method according to claim 9, wherein the positioning comprises positioning the framework with a polymeric member along the proximal side of the framework.

13. The method according to claim 9, wherein the positioning comprises moving anchor frame segments of the framework between a non-deployed position and a deployed position.

14. The method according to claim 9, wherein the positioning comprises moving anchor frame segments of the framework between a retracted position and a deployed position by moving the secondary hub along the axis.

15. The method according to claim 9, further comprising advancing the framework from a distal end of a sheath such that the framework at least partially self-expands.

16. The method according to claim 9, wherein the positioning comprises positioning the framework with a tissue growth member along the proximal side of the framework, the tissue growth member having a hydrophilic coating associated therewith.

17. The method according to claim 9, wherein the positioning comprises positioning the framework with the framework extending in the secondary hub on a secondary hub distal side.

18. The method according to claim 9, wherein the positioning comprises positioning the framework with the framework extending proximally into the secondary hub.

19. The method according to claim 9, wherein the positioning comprises positioning the framework with the framework extending radially inward and proximally to the secondary hub.

20. The method according to claim 1, wherein the positioning comprises positioning the framework with the framework extending in the secondary hub on a secondary hub distal side.

* * * * *